United States Patent

Yoon et al.

(10) Patent No.: US 6,831,079 B1
(45) Date of Patent: Dec. 14, 2004

(54) VASOPRESSIN AGONIST FORMULATION AND PROCESS

(75) Inventors: Joseph K. Yoon, Palisade Park, NJ (US); Richard W Saunders, Palisades, NY (US); Mahdi Fawzi, Morristown, NJ (US)

(73) Assignee: American Cyanamid Company, Madison, NJ (US)

( * ) Notice: Subject to any disclaimer, the term of this patent is extended or adjusted under 35 U.S.C. 154(b) by 401 days.

(21) Appl. No.: 09/669,204

(22) Filed: Sep. 25, 2000

Related U.S. Application Data

(60) Provisional application No. 60/228,814, filed on Sep. 27, 1999, now abandoned.

(51) Int. Cl.[7] .................. A61K 31/55; A61K 47/32; A61K 9/64
(52) U.S. Cl. ................ 514/220; 514/937; 424/452; 424/455
(58) Field of Search ................. 514/220, 937; 424/452, 455

(56) References Cited

U.S. PATENT DOCUMENTS

| | | | |
|---|---|---|---|
| 4,578,391 A | | 3/1986 | Kawata et al. |
| 4,620,974 A | | 11/1986 | Hersh et al. |
| 4,744,988 A | | 5/1988 | Brox |
| 4,954,346 A | * | 9/1990 | Sparta ............... 424/456 |
| 5,071,642 A | * | 12/1991 | Lahr et al. ........... 424/474 |
| 5,641,512 A | | 6/1997 | Cimiluca |
| 6,352,718 B1 | * | 3/2002 | Yoon et al. .......... 424/456 |
| 6,420,358 B1 | * | 7/2002 | Ellis-Grosse et al. ..... 514/220 |
| 6,437,006 B1 | * | 8/2002 | Yoon et al. ........... 514/772.5 |

FOREIGN PATENT DOCUMENTS

| | | |
|---|---|---|
| EP | 0815854 | 1/1998 |
| WO | 9519579 | 7/1995 |
| WO | 9640071 | 12/1996 |
| WO | 9641622 | 12/1996 |
| WO | WO 99/06409 | * 2/1999 |

OTHER PUBLICATIONS

Shah et al., Bull. Tech/Gattefosse Rep., 1996, 89, 27–38.

* cited by examiner

*Primary Examiner*—Zohreh Fay
*Assistant Examiner*—Brian-Yong Kwon
(74) *Attorney, Agent, or Firm*—Joseph M. Mazzarese

(57) ABSTRACT

This invention provides novel formulations for vasopressin agonist compounds, or a pharmaceutically acceptable salt thereof, having the general structure:

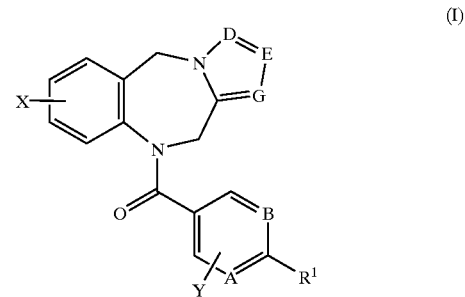

and processes for making them, the formulations comprising from about 1% to about 20% of active ingredient, from about 1% to about 18% of a surfactant component, from about 50% to about 80% of a component of one or more polyethylene glycols, from about 1% to about 20% of a component of one or more sucrose fatty acid esters and/or polyvinylpyrrolidone and, optionally, one or more preservatives or antioxidants.

19 Claims, No Drawings

VASOPRESSIN AGONIST FORMULATION AND PROCESS

This application claims the benefit of U.S. Provisional Application No. 60/228,814, which was converted from U.S. patent application Ser. No. 09/406,165, filed Sep. 27, 1999 now abandoned, pursuant to a petition filed under 37 C.F.R. 1.53(c)(2)(i).

This applications concerns new formulations for a class of tricyclic vasopressin agonist compounds, and pharmaceutically acceptable salts thereof, as well as processes for manufacturing the formulations. The invention particularly relates to orally administered formulations of these compounds.

Background of the Invention

The art describes many methods of producing liquid or semi-solid encapsulated pharmaceutical formulations. In Bull. Tech./Gattefosse Rep. (1996), 89, 27–38, authors Shah et al. describe hard gelatin capsule technology, particularly for use in enhancing the bioavailability of poorly soluble or poorly absorbed drugs.

U.S. Pat. No. 4,620,974 (Hersh et al.) teaches a hard gelatin capsule comprising a telescoping two-piece cap with a lubricant comprising a polyethylene glycol of a molecular weight between about 200 and about 900 present in admixture with the composition at a concentration of from about 0.5 to about 25 weight percent.

WO 96/40071 (Lamberti) discloses methods and devices for producing minimal volume capsules. WO 96/41622 (Tanner et al.) teaches suspensions suitable for encapsulation in gelatin capsules, particularly including a solid phase of solid particles and a liquid phase capable of suspending the solid phase.

U.S. Pat. No. 5,641,512 (Cimiluca) teaches soft gelatin encapsulated analgesics in which the shell contains a xanthine derivative, such as caffeine.

U.S. Pat. No. 4,578,391 (Kawata et al.) describes oily compositions for antitumor agents comprising at least one sparingly oil soluble or water-soluble antitumor drug, at least one fat or oil, and at least one solubilizing adjuvant in an oily vehicle, selected from crown ether, lecithin, polyethylene glycol, propylene glycol, vitamin E, polyoxyehtylene alkylether, and sucrose esters of fatty acids.

EP 0 815 854 A1 discloses a substantially translucent, semi-solid fill material for a soft gelatin capsule, the semi-solid material being sufficiently viscous that it cannot be expelled from the capsule with a syringe at room temperature.

U.S. Pat. No. 4,744,988 (Brox) teaches soft gelatin capsules comprising a shell of gelatin, a softener and a filling of a polyethylene glycol and a low polyhydric alcohol and at least one active substance, characterized in that the shell contains 4 to 40 percent sorbital or sorbitanes, at least half of the weight of polyethylene glycol used is a polyethylene glycol having a mean molecular weight of 600, and the capsule filling comprises up to 20% by weight of glycerol and/or 1,2-propylene glycol.

WO 95/19579 (Dhabhar) teaches a process for solubilizing difficulty soluble pharmaceutical agents in a mixture of polyethylene glycol and propylene glycol by using a polyvinylpyrrolidone with a specific viscosity average molecular weight of from about 5,000 to about 25,000.

SUMMARY OF THE INVENTION

This invention provides orally administerable formulations for tricyclic vasopressin agonist compounds, or the pharmaceutically acceptable salts thereof, singularly or collectively optionally referred to herein as "active ingredient", which have the structure:

(I)

wherein:

A, B, E, G are, independently, CH or nitrogen;

D is, independently, C—W or nitrogen;

$R^1$ is alkanoyl of 2 to 7 carbon atoms, a group selected from CN, COOH, $CONH_2$,

———H,      ———$R_9$, or a moiety selected from the group:

(a)

(b)

(c)

(d)

(e)

(f)

(g)

-continued

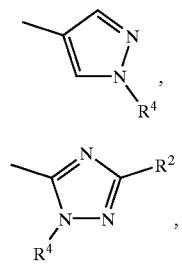
(h)

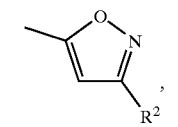
(i)

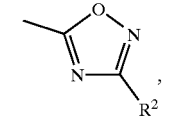
(j)

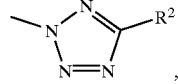
(k)

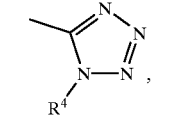
(l)

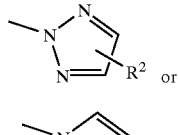
(m)

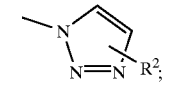
(n)

or (o)

R², R³ and R⁵ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

R⁴ is hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, or an acyl substituent selected from the group consisting of alkanoyl of 2 to 7 carbon atoms, alkenoyl of 3 to 7 carbon atoms, cycloalkanoyl of 3 to 7 carbon atoms, aroyl, or arylalkanoyl;

and Y are, independently, hydrogen, straight chain alkyl of 1 to 6 carbon atoms, branched chain alkyl of 3 to 7 carbon atoms, cycloalkyl of 3 to 7 carbon atoms, perfluoroalkyl of 1 to 6 carbons, alkoxyalkyl of 2 to 7 carbon atoms, halogen (including chlorine, bromine, fluorine, and iodine), alkoxy of 1 to 6 carbons, hydroxy, $CF_3$, or perfluoroalkyl of 2 to 6 carbons;

W is hydrogen, halogen (preferably chloro, bromo or iodo), alkyl, alkoxyalkyl of 2 to 7 carbons, hydroxyalkyl of 1 to 6 carbons, or $CH_2NR^6R^7$;

R⁶ and R⁷ are, independently, hydrogen, straight chain alkyl of 1 to 6 carbon atoms, branched chain alkyl of 3 to 7 carbon atoms; or, taken together with the nitrogen atom of $CH_2NR^6R^7$, R⁶ and R⁷ form a five or six membered ring optionally containing one or more additional heteroatoms such as, but not limited to, those of the group:

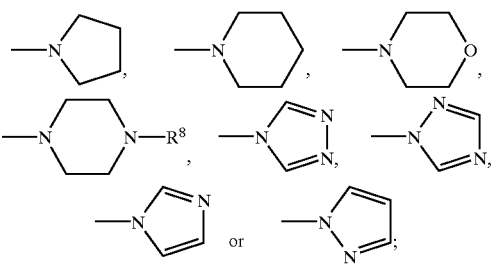

R⁸ is a straight chain alkyl of 1 to 6 carbon atoms
R⁹ is independently hydrogen, trimethylsilyl or a straight chain alkyl of 1 to 6 carbon atoms;

or a pharmaceutically acceptable salt, ester or prodrug form thereof.

Among the more preferred active ingredient compounds of the formulations of this invention are those of the formula:

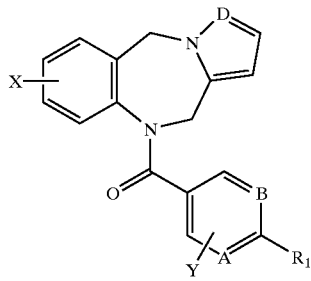

wherein:

A and B are, independently, CH or nitrogen;

D is C—W or nitrogen;

R¹ is alkanoyl of 2 to 7 carbon atoms or a group selected from

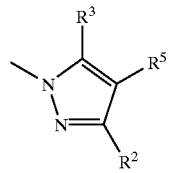
(a)

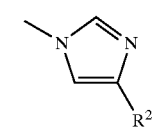
(b)

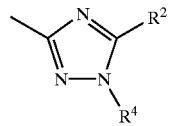
(e)

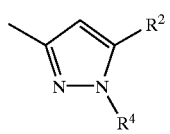
(f)

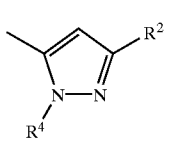
(g)

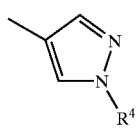
(h)

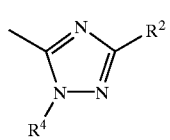
(i)

or

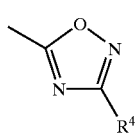
(k)

$R^2$, $R^3$ and $R^5$ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

$R^4$, X, Y, W, $R^6$, $R^7$ and $R^8$ are as defined above;

or a pharmaceutically acceptable salt thereof.

For the compounds defined above and referred to herein, unless otherwise noted, aroyl groups include, for example, benzoyl, naphthoyl which can be substituted independently with one or more substituents from the group of hydrogen, halogen, cyano, straight chain alkyl of 1 to 6 carbon atoms, branched chain alkyl of 3 to 7 carbon atoms, alkoxy of 1 to 6 carbons, $CF_3$, or phenyl.

Heteroaroyl groups herein refer to a carbonyl (radical ) directly bonded to a carbon atom of a five membered heterocyclic ring having one or two heteroatoms selected from nitrogen, oxygen, sulfur, for example 2-thienoyl. The heterocyclic ring of the heteroaroyl groups may also include, but are not limited to, groups in which the aryl portion is a furan, pyrrole, 2H-pyrrole, imidazole, pyrazole, isothiazole, isoxazole, thiophene, pyrazoline, imidazolidine or pyrazolidine group. The heteroaryl groups herein can be substituted independently with one or more substituents from the group of hydrogen, halogen, cyano, straight chain alkyl of 1 to 6 carbon atoms, or branched chain alkyl of 3 to 7 carbon atoms.

The arylalkanoyl groups herein refer to a carbonyl group or radical directly bonded to an alkyl group of 1 to 6 carbon atoms which is terminally substituted by an aryl group, for example, phenylacetic acid. The aryl group can be substituted independently with one or more substituents from the group of hydrogen, halogen, cyano, straight chain alkyl of 1 to 6 carbon atoms, branched chain alkyl of 3 to 7 carbon atoms, alkoxy of 1 to 6 carbons, $CF_3$, or phenyl or substituted phenyl where the substituents are selected from halogen, cyano, straight chain alkyl of 1 to 6 carbon atoms, branched chain alkyl of 3 to 7 carbon atoms, alkoxy of 1 to 6 carbons, $CF_3$.

The halogens referred to herein may be selected from fluorine, chlorine, bromine or iodine, unless otherwise specified.

It is understood by those practicing the art that the definition of the compounds of formula (I), when $R^1$, $R^2$, $R^3$, $R^4$, $R^5$, $R^6$, $R^7$, X, or Y contain symmetric carbons, encompass all possible stereoisomers and mixtures thereof which possess the activity discussed below. In particular, it encompasses any optical isomers and diastereomers; as well as the racemic and resolved, enantiomerically pure R and S stereoisomers; as well as other mixtures of the R and S stereoisomers and pharmaceutically acceptable salts thereof, which possess the indicated activity. Optical isomers may be obtained in pure form by standard separation techniques. It is also understood that the definition of $R^1$, $R^2$, $R^3$, $R^4$, $R^5$, $R^6$, $R^7$, X, or Y of the compounds of formula (I), encompasses all possible regioisomers, and mixtures thereof which possess the activity discussed below. Such regioisomers may be obtained pure by standard separation methods known to those skilled in the art.

Also among the preferred groups of active ingredients in the formulations of this invention are those in the subgroups:

a) compounds having the general formula:

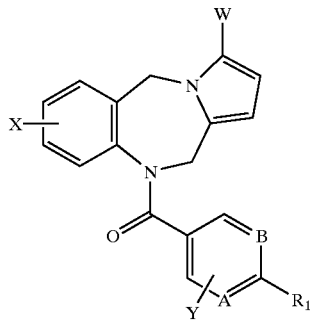

wherein A, B, W, $R^1$, $R^2$, $R^3$, $R^4$, $R^5$, $R^6$, $R^7$, $R^8$, $R^9$, X, and Y are as defined above;

b) compounds having the general formula:

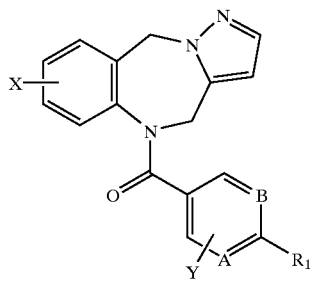

wherein A, B, $R^1$, $R^2$, $R^3$, $R^4$, $R^5$, $R^9$, X, and Y, are as defined above; and c) compounds having the general formula:

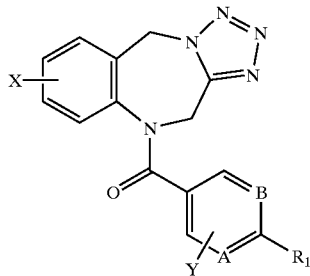

wherein A, B, $R^1$, $R^2$, $R^3$, $R^4$, $R^5$, $R^9$, X, and Y, are as defined above.

It is understood that subgroups a)–c), above, further include subgroups wherein:

A and B are, independently, CH or nitrogen;

$R^1$ is alkanoyl of 2 to 7 carbon atoms or a group selected from

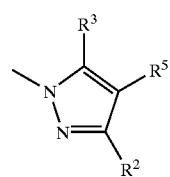 (a)

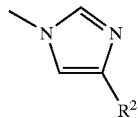 (b)

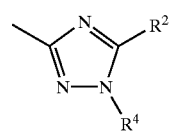 (e)

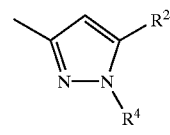 (f)

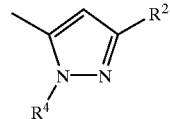 (g)

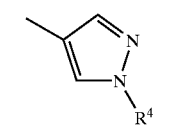 (h)

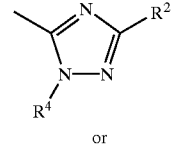 (i)

or

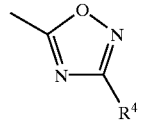 (k)

$R^2$, $R^3$ and $R^5$ are, independently, hydrogen, straight chain alkyl of 1 to 6 carbon atoms, branched chain alkyl of 3 to 7 carbon atoms, cycloalkyl of 3 to 7 carbon atom s, or perfluoroalkyl of 1 to 6 carbons; and $R^4$, X, Y, W, $R^6$, $R^7$ and $R^8$ are as defined above;

or a pharmaceutically acceptable salt thereof.

Particularly preferred among the compounds of group a), above, are those in which W is H, A and B are each CH, and $R^1$ is the group of alkanoyl of 2 to 7 carbon atoms or a group selected from the moieties (a), (b), (e), (f), (g), (h), (i) or (k), listed above.

The pharmaceutically acceptable salts include those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids.

Among the most preferred formulations of this invention are those described herein having as the active ingredient [2-Chloro-4-(3-methyl-pyrazol-1-yl)-phenyl-(5H, 11H)-pyrrolo[2,1-c][1,4]benzodiazepin-10-yl)-methanone, or pharmaceutically acceptable salts thereof, having the structure:

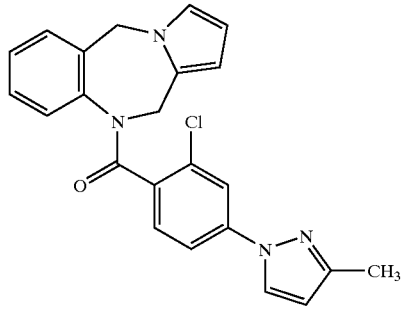

The formulations of this invention are useful in methods for treating in humans or other mammals diseases, conditions or disorders in which vasopressin agonist activity is desired. These methods of treatment include those for diseases, conditions or disorders which make it desirable to release factor VIII and von Willebrand factor into the circulatory system, release tissue-type plasminogen activator (t-PA) in the blood circulation, or affect the renal conservation of water and urine concentration. Such methods of treatment include, but are not limited to, treatments for diabetes insipidus, nocturnal enuresis, nocturia, urinary incontinence, or bleeding and coagulation disorders in humans or other mammals, including hemophilia.

The methods herein for which these formulations are used include facilitation in humans or other mammals of temporary delay of urination, which may also be described as controlling or treating the inability to temporarily delay urination, whenever desirable. This method is understood to include treatments facilitating the temporary delay of urination which are separate from and not included in the treatment of the conditions known as nocturnal enuresis and nocturia.

In order to obtain consistency of administration, it is preferred that a composition of the invention is in the form of a unit dose. Suitable unit dose forms preferably include tablets or capsules, though one skilled in the art will understand semi-solids or gels of this invention are also readily made and useful. Such unit dose forms may contain from 0.1 to 1000 mg of a compound of the invention and preferably from 2 to 50 mg. Still further preferred unit dosage forms contain 1 to 25 mg, more preferably from 1 to 10 mg, of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with other conventional carriers or excipients such as fillers, disintegrating agents, binders, lubricants, flavoring agents and the like.

The formulations of this invention comprise (by % w/w):
a) from about 1% to about 20% of active ingredient, or a pharmaceutically acceptable salt thereof, preferably from about 5% to about 16% of this active ingredient;
b) from about 1% to about 15% of a surfactant component, preferably from about 5% to about 10% of the surfactant component;
c) from about 50% to about 80% of a component of one or more olyethylene glycols (PEG), preferably from about 55% to about 70% of one or more olyethylene glycols; and
d) from about 1% to about 20%, preferably from about 5% to about 15% and more preferably between about 8% and about 12%, of a component of:
  i) one or more sucrose fatty acid esters; or
  ii) a polyvinylpyrrolidone (PVP) with a K value between about 15 and 90, preferably with a K value of from about 17 as defined in USP/NF; or
  iii) a combination of one or more sucrose fatty acid esters and a PVP, as defined above.

The polyethylene glycol component may be comprised of one or more PEG polymers, preferably commercially available PEG polymers between PEG 200 and PEG 4,000, i.e. those PEG polymers having an average molecular weight between about 190 and about 4800. More preferred are PEG polymers between average molecular weights of from about 190 to about 3450, most preferably between about 400 and 1540. Among the preferred PEG polymers are PEG 400, having an average molecular weight between about 380 and about 420, and PEG 1,000, having an average molecular weight between about 950 and about 1050. The ratio of high and low molecular weight PEG species within the PEG component is preferably from about 2.5:1 to about 1:2.5, more preferably about 1:1. As an example, a preferred blend of PEG polymers within this invention would include a 1:1 blend of PEG 400 and PEG 1000. It may be preferable to choose a mixture of PEG components which will have a melting point at or near the physiological temperature of the mammal to receive the formulation. Mixtures of final components which have a viscosity range of from about 140 to about 1500 centipoise at 37° C. may be preferred, more preferably a range of from 300 to about 800 centipoise at 37° C.

The surfactants that may be used with the present formulations include, but not limited to, polysorbate 20 (polyoxyethylene 20 sorbitan monolaurate), Polysorbate 60, Polysorbate 40, polysorbate 80, Span 80 Sorbitan Oleate, a product of ICI Americas, Wilmington, Del., polysorbate 81, polysorbate 85, polysorbate 120, bile acids and salts defined by Martindale The Extra Pharmacopoeia Thirtieth Edition on page 1341–1342 such as Sodium taurocholates, Sodium deoxytaurocholates, Chenodeoxycholic acid, and ursodeoxycholic acid, and pluronic or poloxamers such as Pluronic F68, Pluronic L44, Pluronic L101, or combinations of one or more of the above. Polysorbate 80, by itself or in combination with one or more other surfactants, is preferred for use with this invention.

The sucrose fatty acid esters useful with this invention include those commercially available and art recognized esters useful for orally administered pharmaceutical compositions, including monoesters, diesters and triesters of sucrose, or mixtures or blends thereof. Specific examples of esters useful with this invention are sucrose monolaurate, sucrose monomyristate, sucrose monopalminate, sucrose monostearate, sucrose distearate, sucrose tristearate, sucrose trimyristate, and sucrose tripalmitate, or combinations thereof.

In addition to these components, other enhancing or protective antioxidants or preservatives may be added to the compositions of this invention, which may account for up to about 4% by weight of the formulation. Examples may include ascorbyl palmitate, benzyl alcohol, butylated hydroxyanisole (BHA), butylated hydroxytoluene (BHT), etc. Examples of these components in the present formulations would include BHA at a concentration from about 0.3% to about 2.5% (% w/w) and BHT at a concentration from about 0.005% to about 0.15% (% w/w), preferably with a mixture of BHA and BHT within these ranges.

A formulation of this invention utilizing one or more of these antioxidants or preservatives comprises:
a) from about 1% to about 20% of active ingredient, or a pharmaceutically acceptable salt thereof, preferably from about 5% to about 16% of this active ingredient;
b) from about 1% to about 18% of a surfactant component, preferably from about 5% to about 15% of the surfactant component, more preferably from about 8 to about 12% of the surfactant component;
c) from about 50% to about 80% of a component of one or more polyethylene glycols (PEG), preferably from about 55% to about 70% of one or more polyethylene glycols;
d) from about 1% to about 20%, preferably about 5% to about 15%, of one or more sucrose fatty acid esters or polyvinylpyrrolidone (PVP) with a K value between about 15 and 90, preferably with a K value of from about 17 as defined in USP/NF; and
e) from about 0.1% to about 4% of one or more preservatives or antioxidants, for example from about 0.3% to about 2.5% (% w/w) BHA and/or from about 0.005% to about 0.15% (% w/w) BHT.

One preferred embodiment of this invention provides a pharmaceutical formulation comprising:
a) from about 5% to about 16% of active ingredient;
b) from about 5% to about 10% of a surfactant component;
c) a component of from about 55% to about 70% of one or more polyethylene glycols;
d) from about 5% to about 15% of polyvinylpyrrolidone (PVP) with a K value between about 15 and 90, preferably with a K value of from about 17 as defined in USP/NF; and
e) from about 0.3% to about 2.5% (% w/w) BHA and from about 0.005% to about 0.15% (% w/w) BHT.

Preferably, the formulations of this invention are enclosed in a sealed enclosure after manufacture, such as soft or hard gelatin capsules. The formulations of this invention may be created as a liquid or semi-liquid formulation and introduced into a capsule. Similarly, using an acceptable range of components and/or temperatures, the formulation may be made as a gel or solid prior to encapsulation.

DETAILED DESCRIPTION OF THE INVENTION

The active compounds useful in the formulations of the present invention may be prepared according to one of the general processes outlined below.

As shown in Scheme I, a tricyclic benzodiazepine of formula (1) is treated with an appropriately substituted acetylaroyl (heteroaroyl) halide, preferably an aroyl (heteroaroyl) chloride of formula (2) in the presence of a base such as pyridine or a trialkylamine such as triethylamine, in an aprotic organic solvent such as dichloromethane or tetrahydrofuran at temperatures from −40° C. to 50° C. to yield the acylated derivative of formula (3). Treatment of (3) with a dialkylamide dialkyl acetal of formula (4) in an aprotic organic solvent such as dichloromethane at temperatures ranging from 0° C. to the reflux temperature of the solvent yields the enone of formula (5) according to the procedure of Lin et al., *J. Het. Chem.*, 14, 345 (1977). Treatment of (5) with hydroxylamine or a substituted hydrazine of formula (6) in acetic acid at temperatures ranging from ambient to the reflux temperature of the solvent yields the target compounds of formula (I) wherein A, B, D, E, G, X, Y, $R^2$ and $R^4$ are as defined above, and $R^1$ is an heterocyclic moiety selected from the (f), (g), or (j) group of heterocycles defined above.

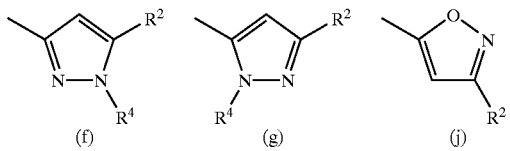

The preferred substituted acetylaroyl (heteroaroyl) chlorides of formula (2) of Scheme I are conveniently prepared by treating the corresponding carboxylic acids with thionyl chloride at temperatures ranging from ambient to the reflux temperature of the solvent, or with oxalyl chloride in an aprotic solvent such as dichloromethane or tetrahydrofuran in the presence of a catalytic amount of dimethylformamide at temperatures ranging from 0° C. to 40° C.

The preferred dialkylamide dialkylacetals are either available commercially, or are known in the literature, or can be conveniently prepared according to procedures analogous to those in the literature. Kantlehner, W. *Chem. Ber.* 105, 1340 (1972).

The preferred tricyclic benzodiazepines of formula (1) are a 10,11-dihydro-5H-pyrrolo[2,1-c][1,4]benzodiazepine (Albright et al., U.S. Pat. No. 5,536,718, issued Jul. 16, 1996), a 10,11-dihydro-5H-pyrazole[5,1-c][1,4]benzodiazepine, Cecchi, L. et. al., *J. Het. Chem.*, 20, 871 (1983). and 10,11-dihydro-5H-tetrazole[5,1-c][1,4]benzodiazepine, Klaubert, D. H., *J. Het. Chem.*, 22, 333 (1985).

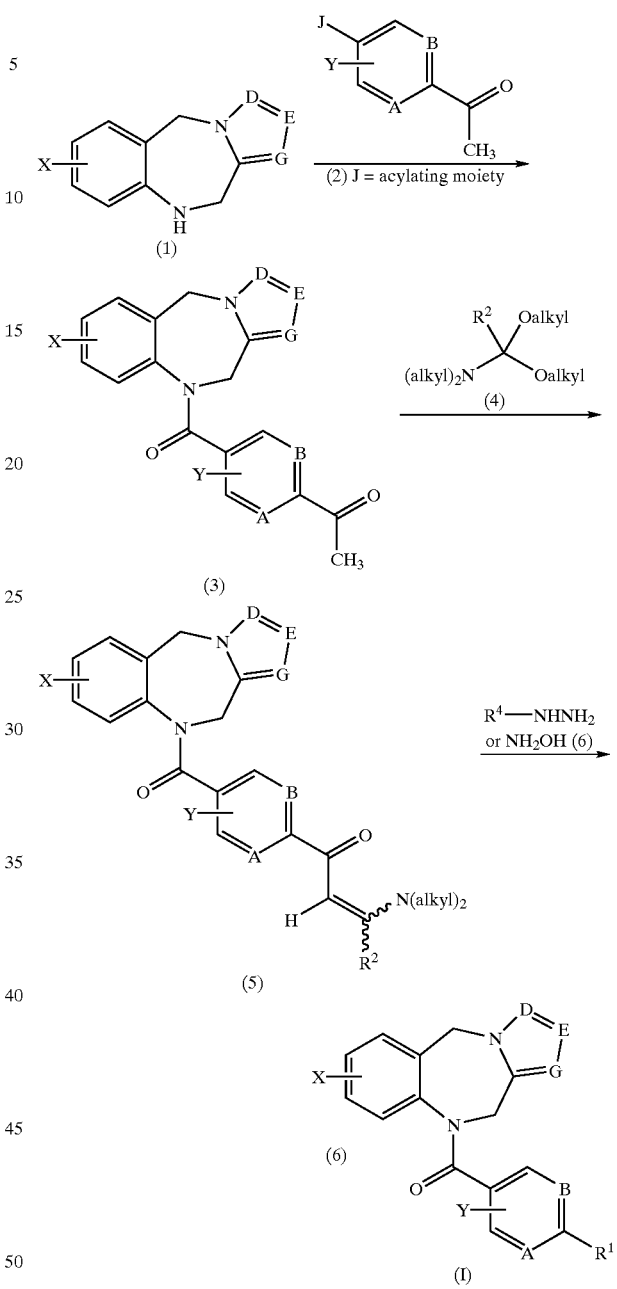

An alternate process for the preparation of intermediates of formula (3) is illustrated in the following Scheme II.

SCHEME II

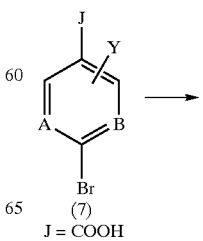

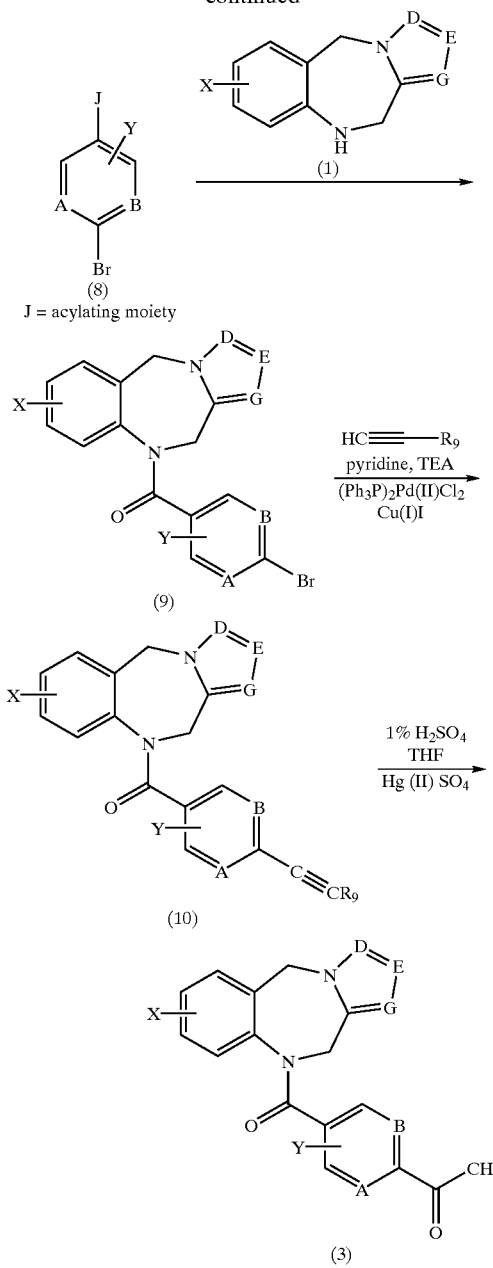

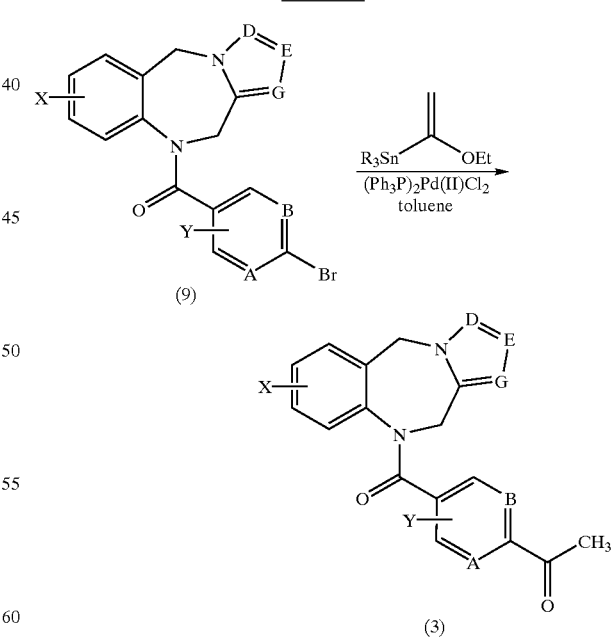

Scheme III hydrated by treatment with 1% sulfuric acid in an aprotic organic solvent such as tetrahydrofuran saturated with mercury (II) sulfate at ambient temperature essentially according to the procedure of Reed et al., *J. Org. Chem.*, 52, 3491 (1987) to provide the desired acyl compound of formula (3) wherein A, B, D, E, G, X, and Y, are as defined above and $R^9$ is hydrogen or a straight chain alkyl of 1 to 6 carbon atoms. Alternatively, compound 9 where $R^9$ is trimethyl is treated with tetrabutylbutylammonium fluoride in an ether solvent such as tetrahydrofuran to afford compound (10) where $R^9$ is hydrogen.

The preferred acylating agents of formula (8) of Scheme II are conveniently prepared by treating an appropriately substituted aryl (heteroaryl) carboxylic acid of formula (7) with thionyl chloride at temperatures ranging from ambient to the reflux temperature of the solvent, or with oxalyl chloride in an aprotic organic solvent such as dichloromethane or tetrahydrofuran in the presence of a catalytic amount of dimethylformamide at temperatures ranging from 0° C. to 40° C.

The protected acetylene intermediates of Scheme II are either available commercially, or are known in the art, or can be readily prepared by procedures analogous to those in the art.

As shown in Scheme III, the intermediate acetyl compounds (3) of Scheme I can be prepared also by the Stille coupling of a bromo aryl (heteroaryl) compound of formula (9) of Scheme II with a (α-ethoxyvinyl)trialkyltin, preferably a (α-ethoxyvinyl)tributylltin, in the presence of a catalytic amount of bis(triphenylphosphine) palladium(II) chloride in an aprotic organic solvent such as toluene at temperatures ranging from ambient to the reflux temperature of the solvent, essentially according to the procedure of Kosugi et al., *Bull. Chem. Soc. Jpn.*, 60, 767 (1987).

Thus, a tricyclic benzodiazepine of formula (1) is treated with an appropriately substituted bromo aroyl (heteroaroyl) halide, preferably an aroyl (heteroaroyl) chloride of formula (8) in the presence of an organic base such as pyridine or a trialkylamine such as triethylamine in an aprotic organic solvent such as dichloromethane or tetrahydrofuran at temperatures from −40° C. to 50° C. to yield the acylated intermediate of formula (9). The intermediate (9) is subsequently coupled with a mono substituted terminal acetylene such as trimethylsilyl or a straight chain alkyl of 1 to 6 carbon atoms, in the presence of pyridine and a catalyst such as bis(triphenylphosphine) palladium (II) chloride and copper (I) iodide in an organic base such as triethylamine as the solvent, in a sealed pressure tube at temperatures ranging from ambient to 100° C. essentially according to the procedure of Martinez et al., *J. Med. Chem.*, 35, 620 (1992). The resulting acetylene intermediate of formula (10) is then The preparation of the acetyl compound (3) can also be accomplished via a palladium-catalyzed arylation of a vinyl alkyl ether such as vinyl butylether, with the aryl halide intermediate of formula (9) according to the procedure of Cabri et al., *Tetrahedron Lett.*, 32, 1753 (1991).

The (a-alkoxyvinyl)trialkyltin intermediates of Scheme III are either available commercially, or are known in the art, or can be readily prepared by procedures analogous to those in the art.

In the case where $R^4$ in Scheme I is hydrogen, the heterocyclic nitrogen can be alkylated or acylated according to the reactions outlined in Scheme IV.

ambient to yield compound (I) wherein A, B, D, E, G, X, Y and $R^2$ are as defined above, and $R^4$ is an alkyl or acyl moiety. The alkylation or acylation of a compound of formula (I, $R^4$ is H) leads to a mixture of regioisomers wherein $R^2$ is hydrogen and $R^1$ is an heterocyclic moiety selected either from the (f) or (g) group of heterocycles defined above and illustrated below, respectively.

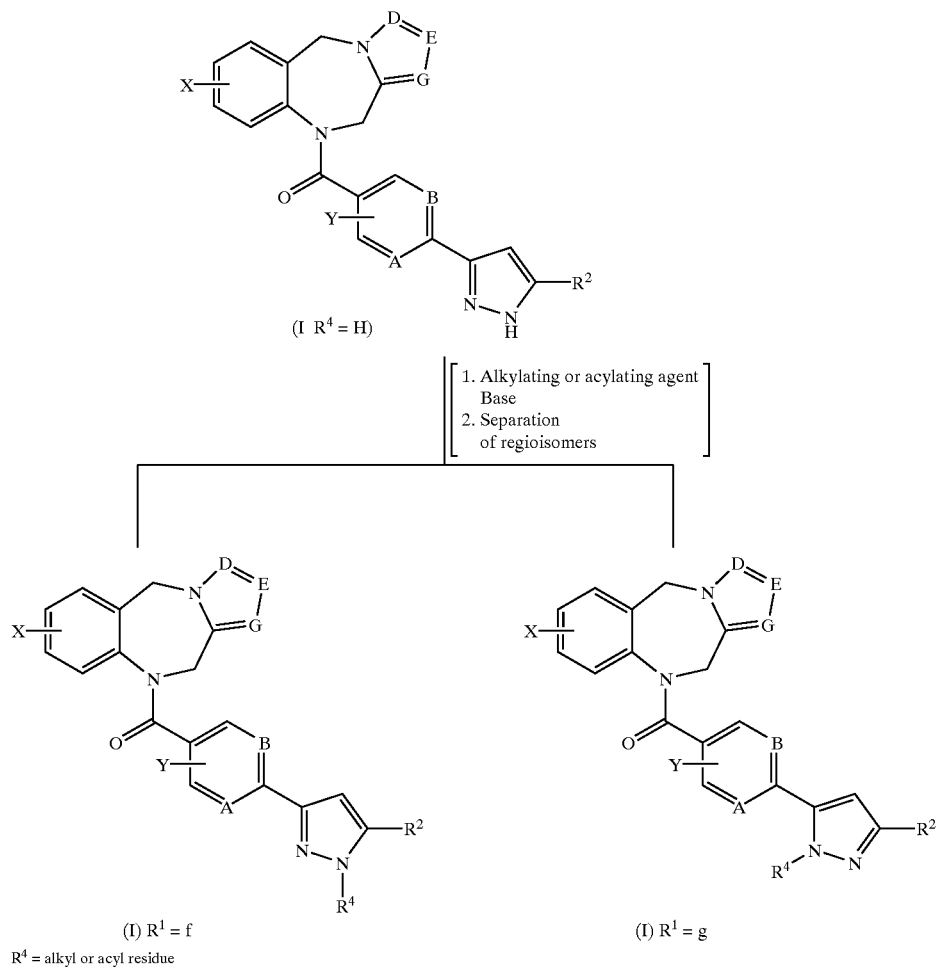

Thus, the pyrazole compound of formula (I, $R^4$ is H) is alkylated by treatment with a strong base such as sodium or potassium hydride and an alkylating agent such as an alkyl halide, preferably an alkyl chloride (bromide or iodide) in an aprotic organic solvent such as dimethylformamide or tetrahydrofuran at temperatures ranging from 0° C. to 80° C. to yield compound (I, $R^1$=(f) or (g)) wherein A, B, D, E, G, X, Y, and $R^2$ are as defined above, and $R^4$ is an alkyl or acyl moiety. Alternatively, compound (I) is acylated by treatment with a carboxylic acid halide, preferably a chloride, or a carboxylic acid anhydride in the presence of an amine base such as pyridine or a trialkylamine, preferably triethylamine, in an aprotic organic solvent such as dichloromethane or tetrahydrofuran with no additional solvent when pyridine is used as the base, at temperatures ranging from −40° C. to The compounds of general formula (I) of Scheme I wherein A and B are carbon, $R^2$ is H, and $R^1$ is an heterocyclic moiety selected from the (g) group of heterocycles defined above, can be prepared according to the general process outlined in Scheme V.

SCHEME V

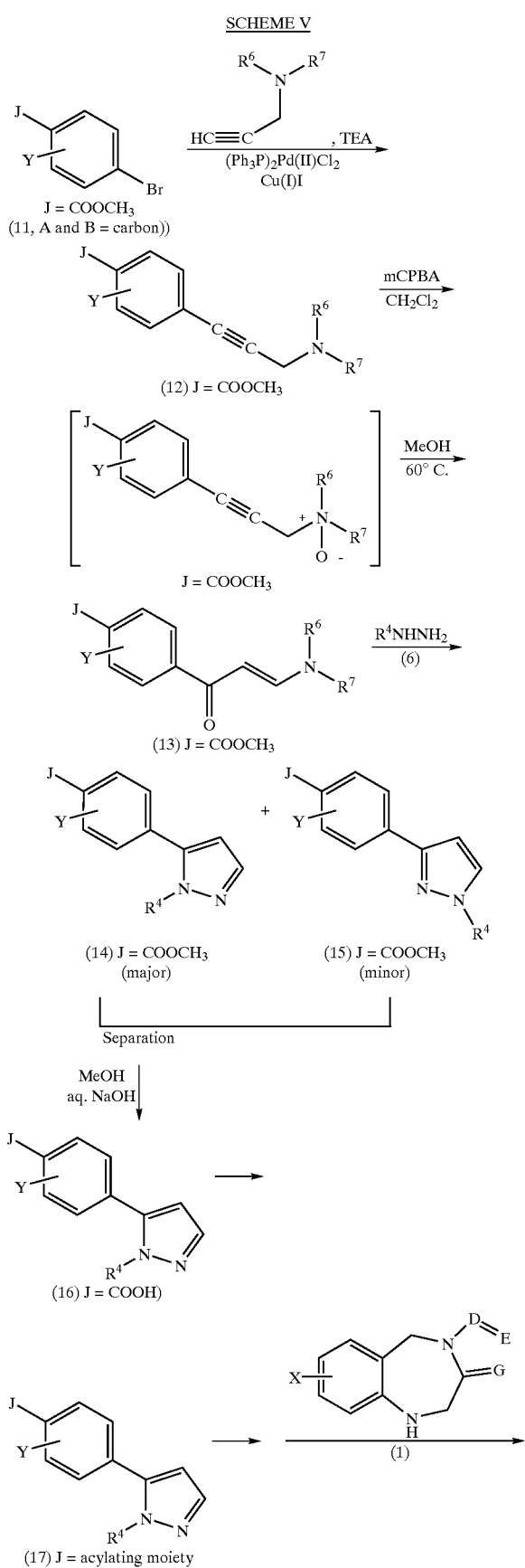

-continued (I)

Thus, an appropriately substituted haloaryl (heteroaryl) carboxylic acid ester, preferably a bromo (or iodo) methylester of formula (11) is coupled with a dialkylamino propyne, preferably 1-dimethylamino propyne, in the presence of a catalyst such as bis(triphenylphosphine) palladium (II) chloride and copper(I) iodide in an organic base such as triethylamine as the solvent and at temperatures ranging from ambient to 80° C. essentially according to the procedures of Alami et al., *Tetrahedron Lett.* 34, 6403 (1993), and of Sanogashira et al., *Tetrahedron Lett.*, 4467 (1975) to provide the substituted acetylene intermediate of general formula (12). The intermediate (12) is subsequently converted into its N-oxide by treatment with an oxidizing agent using any of a number of standard oxidative procedures (Albini, A., *Synthesis*, 263 (1993) or with dioxirane reagents (Murray, R. W., *Chem. Rev.*, 1187 (1989), in an aprotic organic solvent such as dichloromethane at temperatures below ambient. The intermediate N-oxide is not isolated but is rearranged in situ to an enone of general formula (13) by treatment with, preferably with heating, a hydroxylic solvent, including any solvent or combination of solvents composed of or containing water, any $C_1$–$C_8$ straight chain or branched chain alkyl alcohol, ethylene glycol, polyethylene glycol, 1,2-propylene diol, polypropylene glycol, glycerol, 2-methoxyethanol, 2-ethoxyethanol, 2,2,2-trifluoroethanol, benzyl alcohol, phenol, or any equivalent solvent that contains one or more free hydroxyl (—OH) substituent(s) that is known to those skilled in the art.

Solvent systems containing one or more cosolvents, along with one or more solvents may also be used for this process of rearranging the N-oxide to the desired enaminone. The cosolvents referred to herein may be defined as a diluent of the main solvent(s) and can be selected from: hydrocarbons such as pentane, hexane or heptane; aromatic hydrocarbon such as benzene, toluene or xylene; ethers such as diethyl ether, tetrahydrofuran, dioxane or dimethoxy ethane; chlorinated hydrocarbons such as dichloromethane, chloroform, dichloroethane, or tetrachloroethane; or other common solvents such as ethyl acetate, N,N-dimethylformamide, N,N-dimethylacetamide, acetonitrile, dimethylsulfoxide, acetone, or the like.

The conversion of the amine N-oxide into an enaminone may be accomplished by introducing the amine N-oxide into a suitable hydroxylic solvent, preferably with stirring, at or between about room or ambient temperature and about the reflux temperature of the solvent. In other instances the introduction of the amine N-oxide to a hydroxylic solvent, preferably with stirring, may be accomplished in the presence of an acceptable catalyst, such as a palladium(II) catalyst or a copper (I) catalyst, at or between room temperature and the reflux temperature of the solvent.

This procedure provides a novel synthesis of enaminone compounds from propargylic amines or their N-oxides in hydroxylic solvents, which influence the ultimate outcome of the reaction. This new method of enaminone synthesis provides a convenient alternative to existing methods and further extends the range of starting materials that can be converted into enaminone products.

Although the precise mechanism by which a propargylic amine N-oxide is converted into an enaminone product has not been rigorously determined, it likely resembles two known processes; the thermal [2,3]-sigmatropic rearrangement of propargylic amine N-oxides (Craig, et. al., *Tetrahedron Lett.*, 4025, 1979; Hallstrom, et. al., *Tetrahedron Lett.*, 667, 1980; Khuthier, A-H, et. al., *J. Chem. Soc. Chem. Commun.*, 9, 1979) and the conversion of certain isoxazoles into enaminones (Liguori, et. al., *Tetrahedron*, 44, 1255, 1988).

Treatment of (13) with a substituted hydrazine (6) in acetic acid at temperatures ranging from ambient to reflux leads to a mixture of regioisomeric compounds of general formulas (14) and (15) in a variable ratio. The major isomer of formula (14) is separated by means of chromatography and/or crystallization and subsequently hydrolyzed to the desired carboxylic acid of formula (16).

The intermediate (16) is then converted into an acylating species, preferably an acid chloride (bromide or iodide) or a mixed anhydride of formula (17) by procedures analogous to those described hereinbefore. The acylating agent (17) is then used to acylate a tricyclic benzodiazepine of formula (1) by any of the procedures described hereinbefore to yield the desired compound of formula (I), wherein A, B are CH and D, E, G, X, Y, and $R^4$ are as defined above, $R^2$ is hydrogen and $R^1$ is a heterocyclic moiety selected from the (g) group of heterocycles illustrated below.

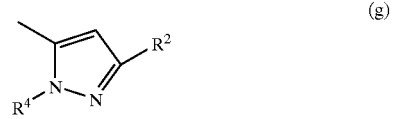

Likewise, treatment of (13) with an unsubstituted hydrazine (6, $R^4$ is H) in acetic acid at temperatures ranging from ambient to the reflux temperature of the solvent yields the intermediate pyrazole ester of formula (18). In this case the heterocyclic nitrogen can be alkylated or acylated as shown in Scheme VI to provide compounds of formula (I) wherein $R^2$ is hydrogen, and $R^1$ is an heterocyclic moiety selected from the (f) group of heterocycles defined above.

SCHEME VI

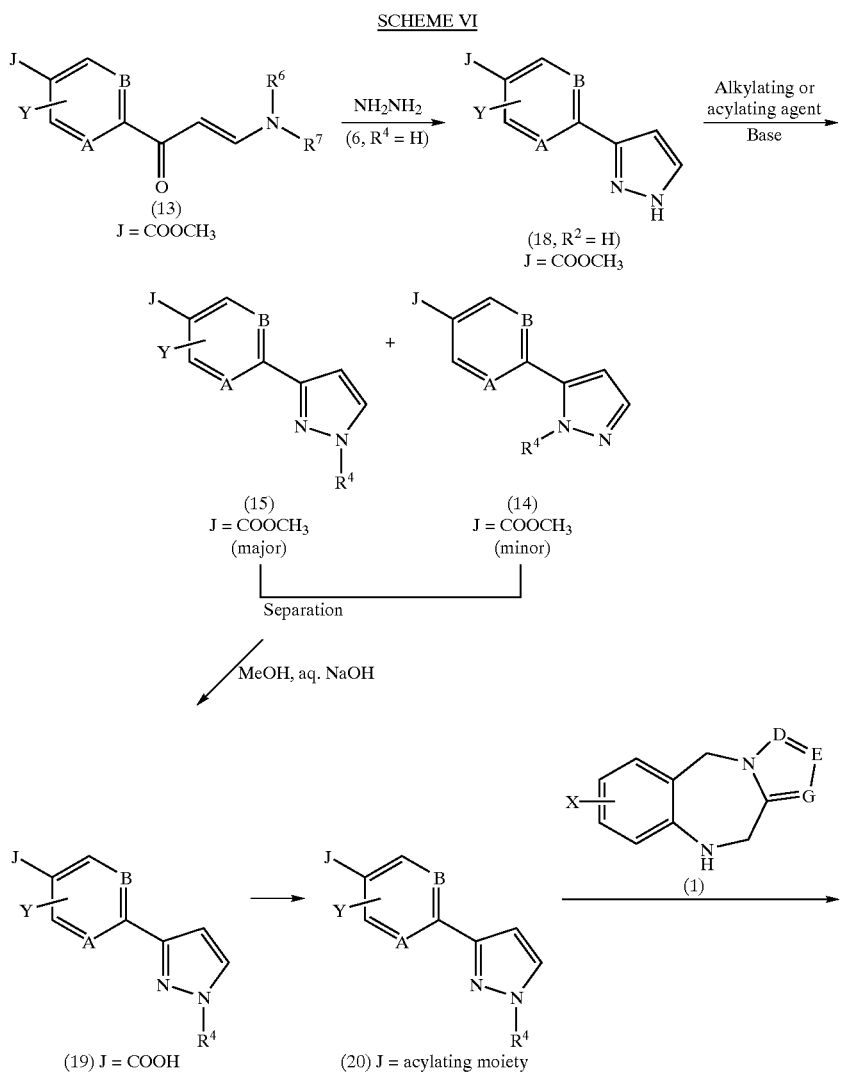

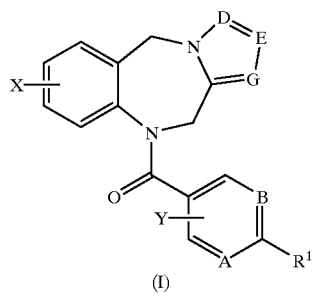

Thus, the intermediate ester of formula (18) is alkylated by treatment with a strong base such as sodium or potassium hydride and an alkylating agent such as an alkyl halide, preferably an alkyl chloride (bromide or iodide), in an aprotic solvent such as dimethylformamide or tetrahydrofuran at temperatures ranging from 0° C. to 80° C. to yield a mixture of regioisomers of formulas (14) and (15) in a variable ratio. The major regioisomer of formula (15) is separated by chromatography and/or crystallization and subsequently hydrolyzed to the desired carboxylic acid of formula (19), which is then converted into an acylating agent, preferably an acyl chloride or a mixed anhydride by procedures analogous to those described hereinbefore. The acylating species of formula (20) is then used to acylate a tricyclic benzodiazepine of formula (1) to yield the desired compound of formula (I), wherein A, B, D, E, G, X, Y, and $R^4$ are as defined above, $R^2$ is hydrogen, and $R^1$ is a heterocyclic moiety selected from the (f) group of heterocycles defined above.

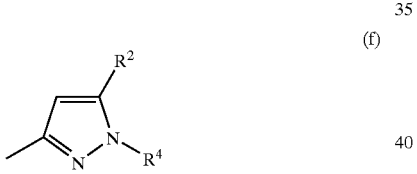

(f)

Compounds of general formula (I) wherein $R^1$ is an heterocyclic moiety selected from the (h) group of $R^1$ heterocycles defined above, can be prepared as outlined in Scheme VII.

SCHEME VII

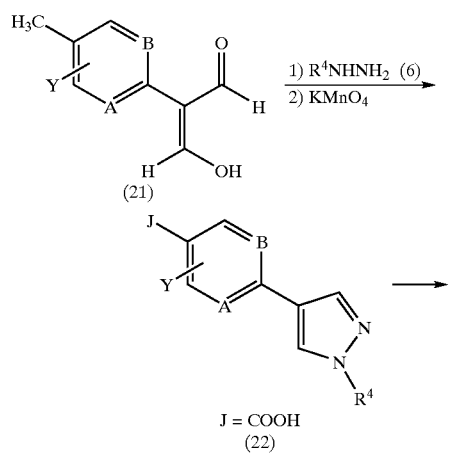

An appropriately substituted malondialdehyde of formula (21) is treated first with a hydrazine in acetic acid at temperatures ranging from ambient to the reflux temperature of the solvent and the intermediate pyrazole is then oxidized with potassium permanganate in a basic aqueous solution at temperatures ranging from ambient to the reflux temperature of the solvent to yield a carboxylic acid intermediate of formula (22). The acid (22) is converted into an acylating agent, preferably an acid chloride (bromide or iodide) or a mixed anhydride by procedures analogous to those described hereinbefore. The acylating agent of formula (23) is finally reacted with a tricyclic benzodiazepine of formula (1) to yield compounds of general formula (I) wherein A, B, D, E, G, X, Y, and $R^4$ are as defined above, and $R^1$ is a heterocyclic moiety selected from the (h) group of heterocycles defined above.

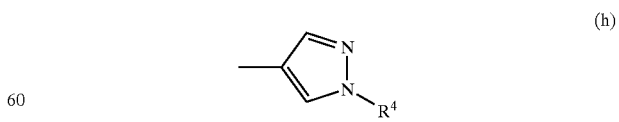

(h)

In the case where $R^4$ in Scheme VII is hydrogen, the heterocyclic nitrogen can be alkylated or acylated according to the procedures outlined hereinbefore.

The preferred malondialdehydes of formula (21) and the hydrazines of Scheme VII are either available commercially, or are known in the art, or can be readily prepared by procedures analogous to those in the literature for known compounds, such as those of Knorr et al., *J. Org. Chem.*, 49, 1288 (1984) and Coppola et al., *J. Het. Chem.*, 11, 51 (1974).

An alternative preparation of the intermediate carboxylic acids of formula (22) of Scheme VII wherein Y is as defined above and $R^4$ is other than hydrogen, is outlined in Scheme VIII.

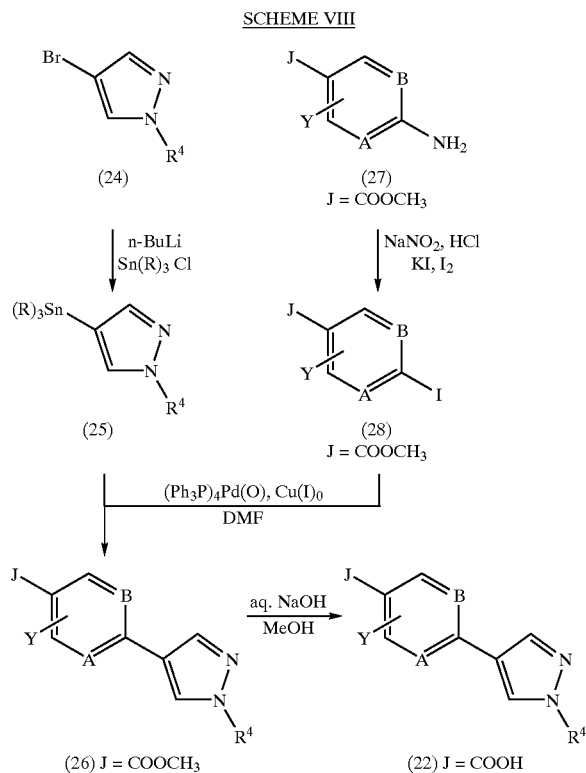

The organotin reagent of formula (25) is reacted in a Stille coupling reaction with an appropriately substituted aryl (heteroaryl) halide, preferably a bromide or iodide of formula (28) in the presence of a catalyst such as tetrakis (triphenylphosphine)palladium (0) and copper (I) iodide in an organic aprotic solvent such as dimethylformamide at temperatures ranging from ambient to 150° C., essentially according to procedures analogous to those found in Farina et al., *J. Org. Chem.*, 59, 5905 (1994). Basic hydrolysis of the resulting ester of formula (26) with sodium or lithium hydroxide in aqueous alcohol or tetrahydrofuran at temperatures ranging from ambient to the reflux temperature of the solvent yields the desired carboxylic acids of formula (22).

In turn, the organotin reagents of formula (25) wherein the R groups are preferably alkyl groups, are conveniently prepared by metallation of a 4-bromo N-alkylpyrazole of formula (24) with a trialkyltin halide, preferably a tributyltin chloride (or bromide) in the presence of a metallating agent such as an alkyllithium such as n-butyl lithium, sec-butyl lithium, or tert-butyllithium in an aprotic organic solvent such as diethylether at temperatures ranging from −40° C. to ambient according to procedures analogous to those found in Martina et al., *Synthesis*, 8, 613 (1991).

The preferred N-alkyl substituted 4-bromo pyrazoles of formula (24) are conveniently prepared from 4-bromo pyrazole by alkylation with an alkyl halide, preferably an alkyl chloride (bromide or iodide) in the presence of a strong base such as lithium, sodium or potassium hydride in an aprotic organic solvent such as dimethylformamide or tetrahydrofuran at temperatures ranging from 0° C. to 80° C. Alternatively, alkylation of 4-bromopyrazole can be carried out with an alkylating agent mentioned above, and a strong alkaline base such as lithium, sodium or potassium hydroxide in the presence of a phase transfer catalyst (Jones, R. A. Aldrichimica ACTA, 9(3), 35, 1976) such as benzyldimethyltetradecylammonium chloride, or benzyltrimethylammonium chloride.

The preferred aryl (heteroaryl) iodides of formula (28) are conveniently prepared by diazotization of the corresponding substituted anilines of formula (27) followed by reaction of the corresponding diazonium salt with iodine and potassium iodide in aqueous acidic medium essentially according to the procedures of Street et al., *J. Med. Chem.*, 36, 1529 (1993) and of Coffen et al., *J. Org. Chem.*, 49, 296 (1984).

An alternative preparation of compounds of general formula (I) is outlined in Scheme IX.

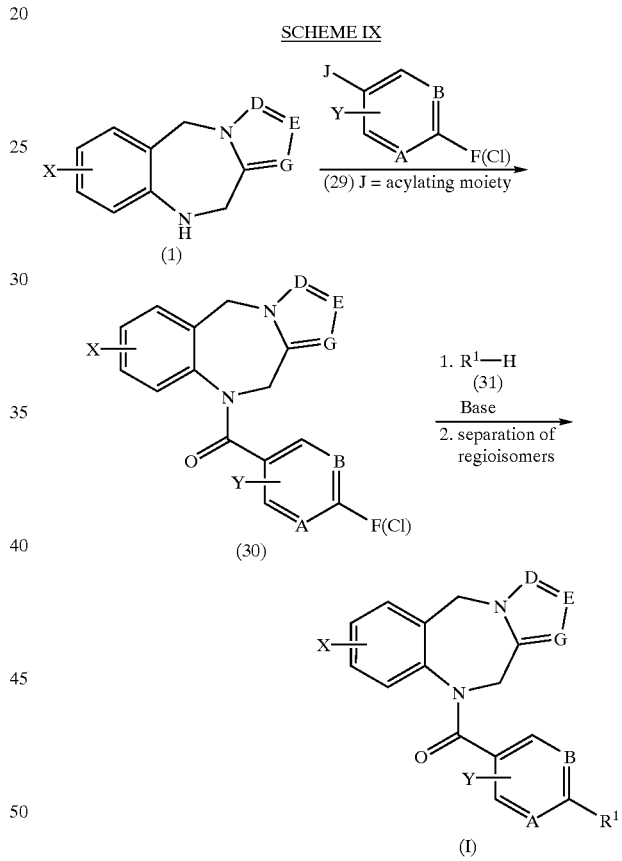

A tricyclic benzodiazepine of formula (1) is treated with an appropriately substituted haloaroyl (heteroaroyl) halide, preferably a fluoro aroyl or a fluoro (or chloro) heteroaroyl chloride of formula (29), in the presence of a base such as triethylamine or diisopropylethylamine in an aprotic organic solvent such as dichloromethane or tetrahydrofuran at temperatures from −40° C. to the reflux temperature of the solvent to yield the acylated derivative (30).

Alternatively, the acylating species can be a mixed anhydride of the carboxylic acid described above, such as that prepared by reaction 2,4,6-trichlorobenzoyl chloride in a solvent such as dichloromethane according to the procedure of Inanaga et al., *Bull. Chem. Soc. Jpn*, 52, 1989 (1979). Treatment of said mixed anhydride of general formula (29)

with the tricyclic benzodiazepine of formula (1) in a solvent such as dichloromethane and in the presence of an organic base such as 4-dimethylaminopyridine at temperatures ranging from 0° C. to the reflux temperature of the solvent, yields the intermediate acylated derivative (30) of Scheme IX.

A compound of formula (30) is then treated with the lithium, sodium or potassium salt of an appropriately substituted heterocycle of formula (31) in a polar aprotic organic solvent such as dimethylformamide or tetrahydrofuran at temperatures ranging from ambient to the reflux temperature of the solvent to yield a compound of general formula (I), wherein A, B, D, E, G, X, Y, $R^2$, $R^3$, and $R^5$ are as defined above, and $R^1$ is a heterocyclic moiety selected from the group consisting of (a), (b), (c), (d), (l), (n) or (o) defined above.

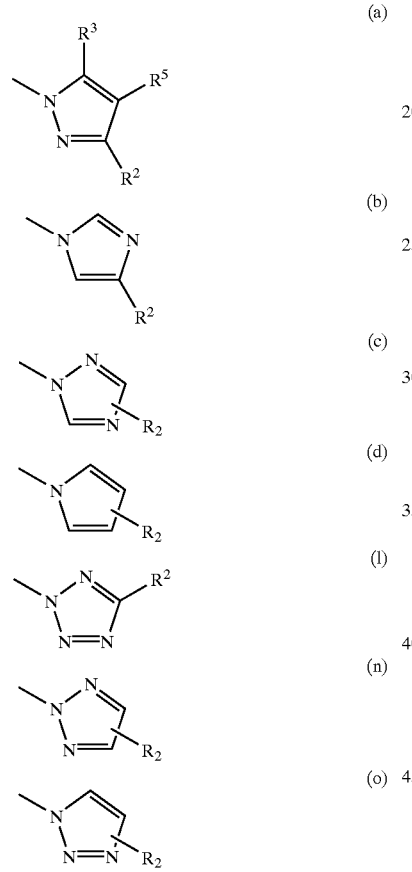

The condensation of the intermediate of formula (30) with the intermediate salt of formula (31) leads to a variable ratio of regioisomers of general formula (I) which are separated by means of chromatography and/or crystallization.

The preferred substituted fluoro aroyl and fluoro (or chloro) heteroaroyl chlorides of formula (29) are either available commercially, or are known in the art, or can be readily prepared by procedures analogous to those in the literature for the known compounds.

The lithium, sodium or potassium salts of the heterocycles of formula (31) are prepared by treatment of said heterocycle with a strong base such as lithium hydride, sodium hydride, potassium hydride or a metal alkoxide at temperatures ranging from −40° C. to ambient in an aprotic organic solvent such as dimethylformamide or tetrahydrofuran.

Alternatively, the compounds of general formula (I) described in Scheme IX can be prepared according to the process outlined in Scheme X.

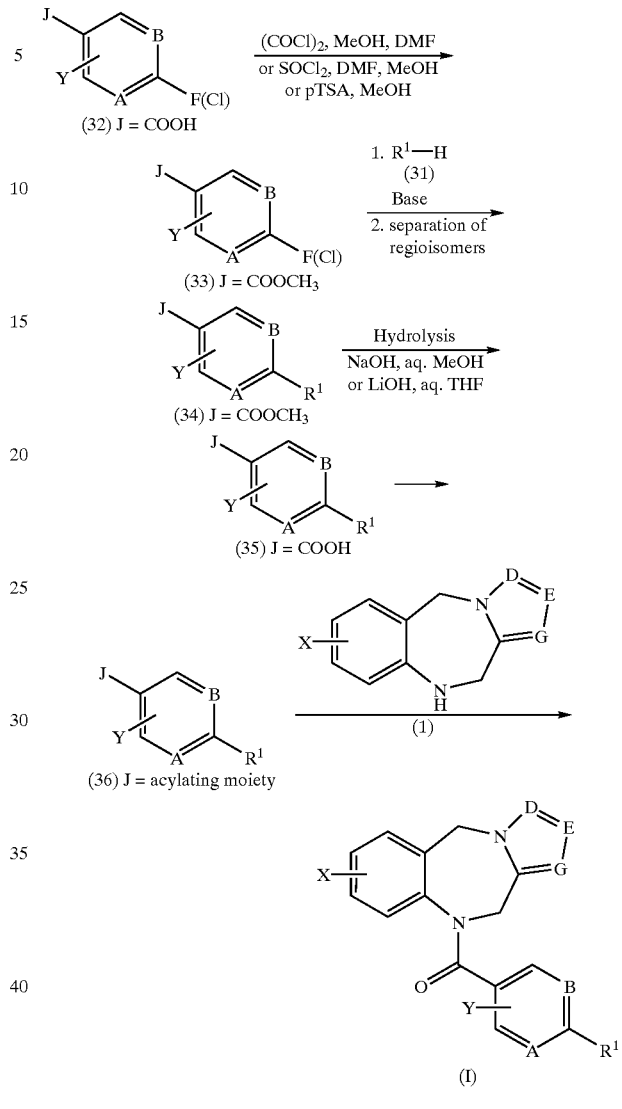

Thus, an appropriately substituted fluoroaryl or fluoro (or chloro)heteroaryl carboxylic acid of formula (32) is esterified using methods known in the art such as treatment with oxalyl chloride (or thionyl chloride) in an alcohol solvent such as methanol, in the presence of a catalytic amount of dimethylformamide; or by condensation with methanol in the presence of an acid catalyst such as para-toluenesulfonic acid at temperatures ranging from ambient to reflux.

The resulting ester of formula (33) is reacted with the lithium, sodium or potassium salt of an appropriately substituted heterocycle of formula (31) in a polar aprotic organic solvent such as dimethylformamide at temperatures ranging from ambient to 150° C., to yield an intermediate ester of formula (34). The condensation of (33) with (31) leads to a variable ratio of regioisomers of formula (34) which are separated by means of chromatography and/or crystallization.

Subsequent hydrolysis of the intermediate ester of formula (34) with an aqueous base such as lithium, sodium or lithium hydroxide in methanol or tetrahydrofuran affords the carboxylic acid of formula (35).

The intermediate carboxylic acid (35) is then converted into an acylating agent preferably an acid chloride or a mixed anhydride of general formula (36) using any of the procedures described hereinbefore.

Subsequent reaction of the tricyclic benzodiazepine of formula (1) with the intermediate acylating agent of formula (36) according to any of the procedures described hereinbefore yields the desired compounds of formula (I) of Scheme IX.

Alternatively, the substituted carboxylic acids of formula (35) described in Scheme X can be prepared according to the process outlined in Scheme XI.

SCHEME XI

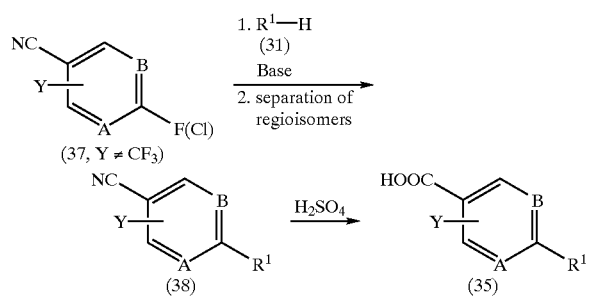

Thus, a fluoro aryl or fluoro (chloro)heteroaryl nitrile of formula (37) is reacted with the lithium, sodium or potassium salt of a substituted heterocycle of formula (31) in an apolar aprotic solvent such as dimethylformamide at temperatures ranging from ambient to 150° C., to yield an intermediate of general formula (38). The reaction of (37) with (31) leads to a variable ratio of regioisomers of formula (38) which are separated by means of chromatography and/or crystallization. Hydrolysis of the intermediate nitriles of formula (38, Y≠CF₃) is preferentially carried out with an inorganic acid such as sulfuric acid at temperatures ranging from ambient to 60° C.

Alternatively, hydrolysis of the nitrile (38) can be carried out by heating in ethanol in the presence of a strong alkaline base such as sodium hydroxide with or without a phase transfer catalyst (Jones, R. A. Aldrichimica Acta, 9(3), 35, 1976,) such as benzyldimethyltetradecyl ammonium chloride.

The resulting carboxylic acids of formula (35) are then converted into the desired compounds of formula (I) of Scheme IX by procedures analogous to those described hereinbefore.

Alternatively, the substituted carboxylic acids of formula (35) of Scheme X can be prepared according to the process outlined in Scheme XII by sequential treatment of a nitrile of formula (38) wherein A and B are CH and where R¹ is not alkanoyl of 2 to 7 carbons, alkynyl, (b) or (d), with basic hydrogen peroxide in dimethylsulfoxide essentially according to the procedure of Katritzky et al., *Synthesis*, 949 (1989), followed by hydrolysis of the resulting amide of formula (38) preferably by treatment with dilute sulfuric acid and sodium nitrite according to the procedure of Hanes et al., *Tetrahedron*, 51, 7403 (1995).

SCHEME XII

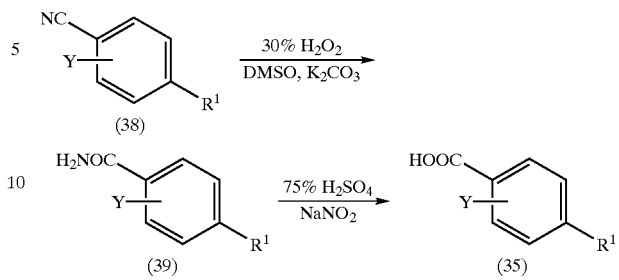

Where R¹ is not (b) or (d)

A preferred process for the preparation of the intermediate substituted carboxylic acids of formula (35) of Scheme X wherein R¹ is a heterocyclic moiety selected from the (a) group of R¹ heterocycles defined above, is outlined in Scheme XIII.

SCHEME XIII

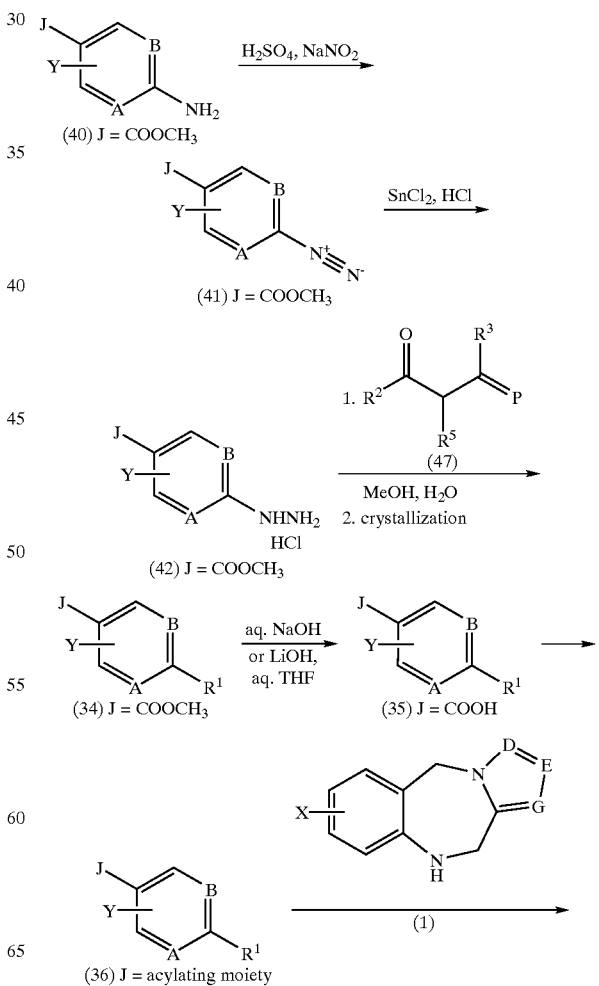

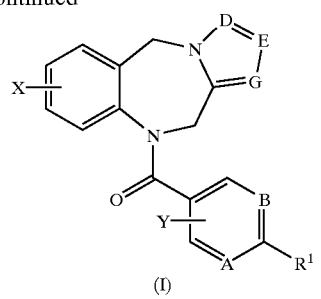

(I)

Diazotization of an appropriately substituted aniline of formula (40) followed by reduction of the resulting diazonium salt of formula (41) with tin (II) chloride in concentrated hydrochloric acid according to the procedure of Street et al., *J. Med. Chem.*, 36, 1529 (1993) provides the intermediate hydrazine hydrochloride salt of formula (42). Subsequent condensation of (42) with an aldehyde derivative of formula (47), wherein $R^2$ is as defined above, $R^3$ and $R^5$ is H, and P is dialkylacetal) such as acetylacetaldehyde dimethyl acetal, or a ketone of formula (47), wherein $R^2$, $R^3$ and $R^5$ are as defined above, and P is =O or (O-alkyl)$_2$ in a solvent such as aqueous methanol at temperatures ranging from ambient to 100° C. provides after crystallization, the desired intermediate ester of formula (34, $R^1$ is (a) and $R^5$ is H), which is then converted to the compound of formula (I) as outlined in Scheme X above.

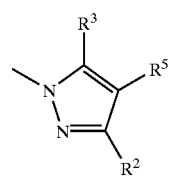

(a)

When Y is OCH$_3$ the compounds of general formula (I) of Scheme I can be conveniently demethylated as outlined in Scheme XIV.

SCHEME XIV

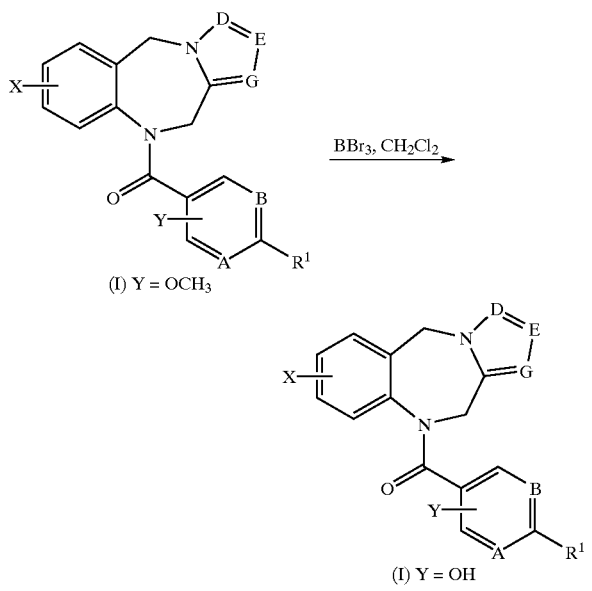

Thus, the reaction of compound (I) wherein Y is OCH$_3$ with boron tribromide in an organic solvent, such as dichloromethane, yields the corresponding phenol of formula (I) wherein Y is OH, and A, B, D, E, G, X, $R^2$ and $R^3$ are as defined above and $R^1$ is an heterocyclic moiety selected from the group (a) of heterocycles defined above and illustrated below.

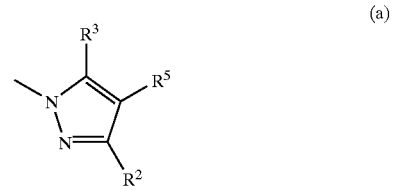

(a)

Compounds in which $R^1$ contains three heteroatoms are prepared according to Scheme XV.

SCHEME XV

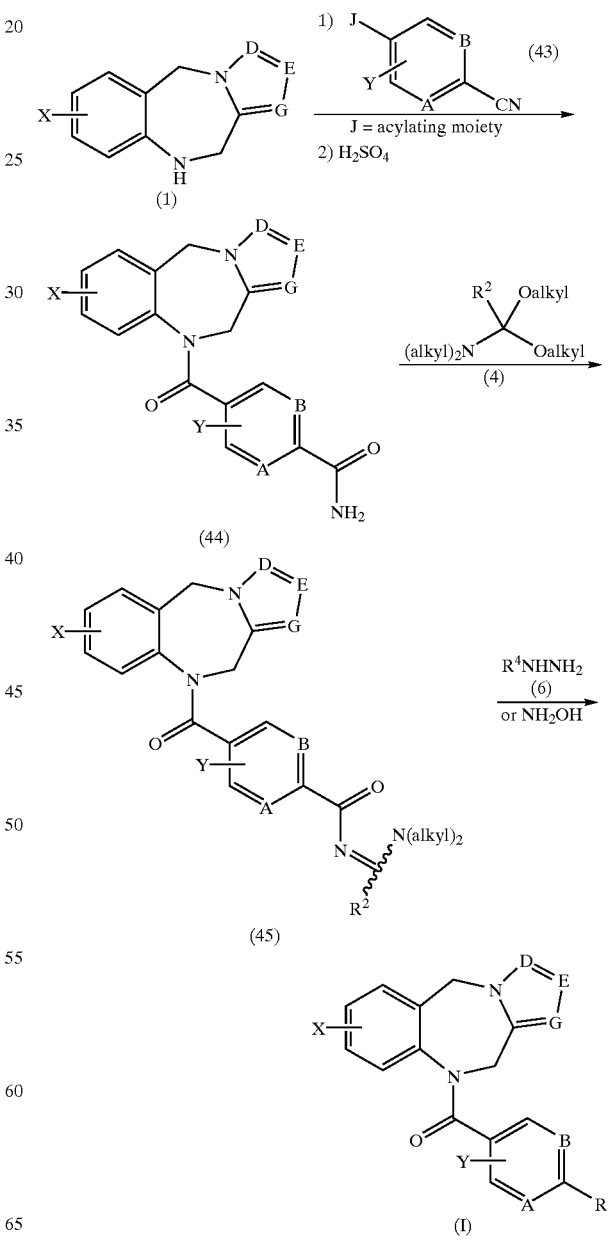

Thus, a tricyclic benzodiazepine of formula (1) is treated with an appropriately substituted cyano aroyl (heteroaroyl) halide, preferably an aroyl (heteroaroyl) chloride of formula (43) in the presence of a base in an aprotic organic solvent such as dichloromethane or tetrahydrofuran at temperatures ranging from −40° C. to 80° C. to yield an intermediate nitrile of formula (46, Scheme XVI) which in turn, is hydrolyzed to an amide intermediate of general formula (44) with an inorganic acid such as sulfuric acid at ambient temperature to 50° C. Treatment of the amide (44) with a dialkyl amide dialkyl acetal of formula (4) in an aprotic organic solvent such as dichloromethane or tetrahydrofuran at temperatures ranging from 0° C. to 80° C. yields the intermediate of formula (45). Treatment of (45) with hydroxylamine or a hydrazine of formula (6) in acetic acid at temperatures ranging from ambient to reflux yields the desired target compounds of formula (I) wherein A, B, D, E, G, X, Y, $R^2$ and $R^4$ are as defined above, and $R^1$ is an heterocyclic moiety selected from the (e), (i) and (k) group of heterocycles defined above.

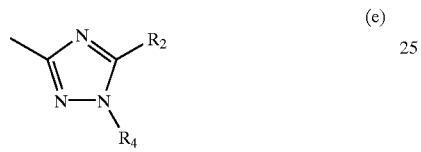
(e)

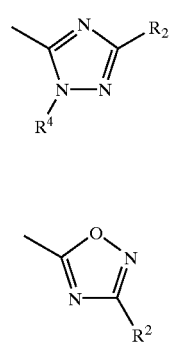
(i)

(k)

Another preferred process for the preparation of the intermediate amide of formula (44), see Scheme XV, wherein A and B are CH and D is not CH is outlined in Scheme XVI and consists of treating a nitrile of formula (46) with basic hydrogen peroxide in dimethylsulfoxide essentially according to the procedure of Katritzky et al., *Synthesis*, 949 (1989).

SCHEME XVI

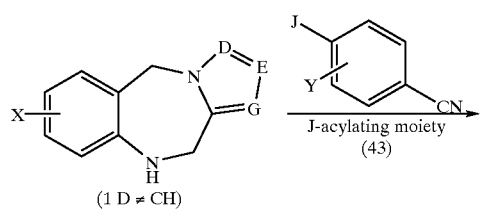

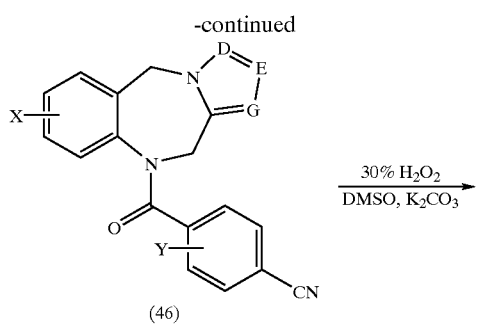

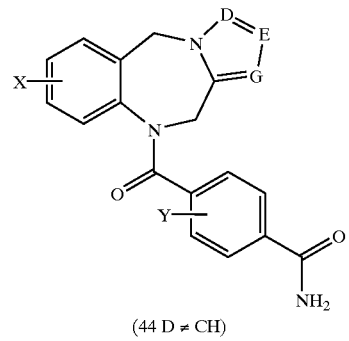
(44 D ≠ CH)

The preferred process to prepare compounds of general formula (I) in which $R^1$ contains four heteroatoms and $R^4$ is hydrogen is outlined in Scheme XVII.

SCHEME XVII

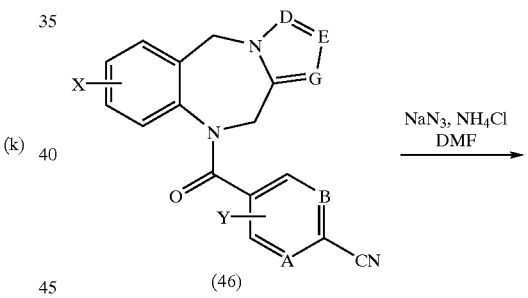

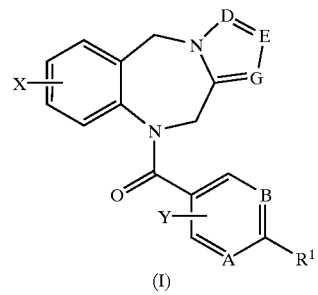
(I)

Treatment of the nitrile intermediate of formula (46) of Scheme XVI with sodium azide and ammonium chloride in an aprotic organic solvent such as dimethylformamide at temperatures ranging from ambient to the reflux temperature of the solvent yields the desired compounds of formula (I) wherein A, B, D, E, G, X, and Y, are as defined above, $R^4$ is hydrogen and $R^1$ is an heterocyclic moiety selected from the group (m) of heterocycles defined above.

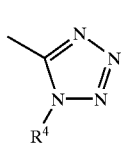

(m)

The compounds of general formula (I) wherein D is CW and W is hydrogen, can undergo Mannich condensation as shown in Scheme XVIII.

SCHEME XVIII

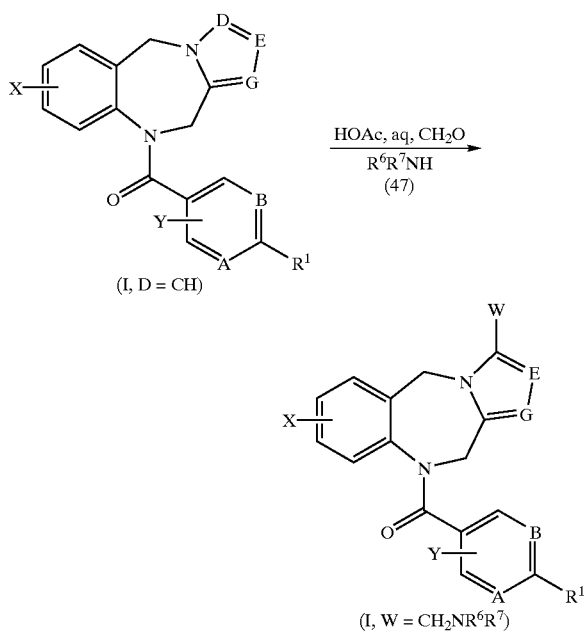

Thus, reaction of compounds of formula (I, D is CH) with either aqueous formaldehyde or paraformaldehyde, a substituted amine of formula (47), and glacial acetic acid in an alcohol solvent such as methanol at temperatures ranging from ambient to reflux yields the corresponding Mannich bases of general formula (I), wherein A, B, E, G, X, Y, $R^2$, $R^3$, $R^5$, $R^6$ and $R^7$ are as defined above; D is CW; W is a dialkylaminoalkyl residue preferably a dimethylaminomethyl residue, and $R^1$ is an heterocyclic moiety selected from the (a), (c), (e), (f), (g), (h), (i), (j), (k), (l), (m), (n) and (o) group of heterocycles defined above.

Likewise, the compounds of general formula (I) wherein D is CH can undergo halogenation as shown in Scheme XIX.

SCHEME XIX

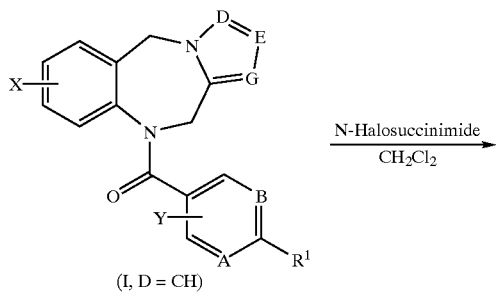

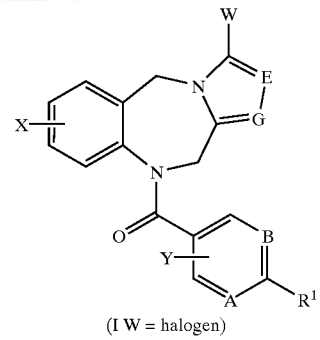

(I W = halogen)

Thus, reaction of (I, D is CH) with a N-halosuccinimide such as N-chloro (bromo or iodo)succinimide in a polar aprotic organic solvent such as dichloromethane at temperatures ranging from −80° C. to ambient yields the corresponding halogenated derivatives of general formula (I), wherein A, B, E, G, X, $R^2$, $R^3$ and $R^5$ are as defined above, D is CW, W is a halogen such as chlorine (bromine or iodine), and $R^1$ is an heterocyclic moiety selected from the (a), (c), (e), (f), (g), (h), (i), (j), (k), (l), (m), (n) and (o) group of heterocycles defined above.

The subject compounds of the present invention were tested for biological activity according to the following procedures.

Vasopressin $V_2$ Agonist Effects of Test Compounds in Normal Conscious Water-loaded Rats Male or female normotensive Sprague-Dawley rats (Charles River Laboratories, Inc., Kingston, N.Y.) of 350–500 g body weight were supplied with standard rodent diet (Purina Rodent Lab. Chow 5001) and water ad libitum. On the day of test, rats were placed individually into metabolic cages equipped with devices to separate the feces from the urine and containers for collection of urine. Test compound or reference agent was given at an oral dose of 10 mg/kg in a volume of 10 ml/kg. The vehicle used was 20% dimethylsulfoxide (DMSO) in 2.5% preboiled corn starch. Thirty minutes after dosing the test compound, rats were gavaged with water at 30 ml/kg into the stomach using a feeding needle. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Mass., 02062) or an Advanced CRYOMATIC Osmometer, Model 3C.2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used.

Vasopressin $V_2$ Agonist Effects of Test Compounds in Normal Conscious Homozygous Brattleboro Rats with Central Diabetes Insipidus Male or female homozygous Brattleboro rats (Harlan Sprague Dawley, Inc., Indianapolis, Ind.) of 250–350 g body weight were supplied with standard rodent diet (Purina Rodent Lab. Chow 5001) and water ad libitum. On the day of test, rats were placed individually into metabolic cages equipped with devices to separate the feces from the urine and containers for collection of urine. Test compound or reference agent was given at an oral dose of 1 to 10 mg/kg in a volume of 10 ml/kg. The vehicle used was 20% dimethylsulfoxide (DMSO) in 2.5% preboiled corn starch. During the test, rats were provided with water ad libitum. Urine was collected for six hours after dosing of the test compound. At the end of six hours, urine volume was measured. Urinary osmolality was determined using a Fiske One-Ten Osmometer (Fiske Associates, Norwood, Mass., 02062) or an Advanced CRYOMATIC Osmometer, Model 3C2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. This animal model was mainly used for evaluation of potency and duration of action of the active compounds. The results of this study are shown in Table I.

| Example # | Urine Volume (% decrease)[a] | Osmolality (% Increase)[b] | Rat Type[c] |
| --- | --- | --- | --- |
| 2 | 80% (1 mg/kg) | 306% (1 mg/kg) | CD |
| 3 | 58% | 240% | CD |
| 4 | 57% | 225% | CD |
| 5 | 56% | 231% | CD |
| 6 | 58% | 270% | CD |
| 7 | 13% | 137% | CD |
| 9A | 70% | 325% | CD |
| 9B | 21% | 168% | CD |
| 11 | 70% | 285% | CD |
| 12 | 69% | 330% | CD |
| 13 | 50% | 229% | CD |
| 14 | 86% | 406% | CD |
| 15 | 47% | 38% | CD |
| 16 | 88% | 400% | CD |
| 18 | 52% | 214% | CD |
| 20 | 25% (1 mg/kg) | 152% (1 mg/kg) | CD |
| 21 | 49% | 181% | CD |
| 22 | 80% | 322% | CD |
| 24 | 47% | 159% | CD |
| 25 | 87% | 979% | CD |
| 26 | 54% | 279% | CD |
| 27 | 76% | 183% | CD |
| 28 | 75% | 37% | CD |
| 29 | 66% | 305% | CD |
| 30 | 81% | 334% | BB |
| 31 | 72% | 298% | CD |
| 32 | 77% | 373% | CD |
| 33 | 68% | 362% | CD |
| 34 | 76% | 407% | BB |
| 35 | 63% | 308% | CD |
| 36 | 66% | 164% | BB |
| 37 | 71% | 370% | CD |
| 38 | 66% | 256% | BB |
| 39 | 69% | 253% | CD |
| 40 | 46% | 183% | CD |
| 41 | 69% | 240% | CD |
| 49 | 74% | 221% | BB |
| 50 | 53% | 223% | CD |
| 51 | 72% |  | CD |
| 52 | 66% | 261% | CD |
| 55 | 80% | 164% | CD |
| 57 | 77% | 288% | CD |
| 58 | 49% | 324% | CD |
| 59 | 80% | 607% | CD |
| 60 | 54% | 165% | CD |
| 61 | 59% | 245% | CD |
| 62 | 22% | 150% | CD |
| 63 | 27% | 214% | CD |
| 64 | 79% | 349% | CD |
| 71 | 84% | 264% | CD |
| 77 | 13% | 90% | CD |
| 78 | 21% | 115% | CD |
| 79 | 38% | 123% | CD |
| 81 | 82% | 490% | CD |
| 83 | 85% | 442% | CD |
| 84 | 56% | 291% | CD |
| 85 | 76% | 436% | CD |
| 86 | 5% | 86% | CD |
| 87 | 71% | 214% | CD |
| 88 | 68% | 226% | CD |
| 90 | 61% | 413% | CD |
| 91 | 22% | 69% | CD |
| 92 | 69% | 454% | CD |
| 95 | 68% | 300% | CD |
| 97 | 3% | 106% | CD |
| 99 | 43% | 205% | CD |
| 100 | 24% | 248% | CD |
| 101 | 76% | 376% | CD |
| 107 | 31% | 125% | CD |
| 108 | 30% | 145% | CD |
| 109 | 21% | 95% | CD |
| 115 | 66% | 229% | CD |
| 116 | 66% | 256% | CD |
| 117 | 68% | 311% | CD |
| 120A | 66% | 269% | CD |
| 120B | 67% | 272% | CD |
| 121 | 22% | 155% | CD |
| 123 | 88% | 663% | CD |

[a]Percent decrease in urine volume vs. control at 10 mg per kg, unless otherwise stated.
[b]Change in osmolality as percent of control at 10 mg/kg, unless otherwise stated.
[c]Rat model used: Sprague-Dawley (CD) or Brattleboro (BB).

The following examples are presented to illustrate rather than limit the scope of the invention.

EXAMPLE 1

(4-Fluoro-2-trifluoromethyl-phenyl)-(5H,11H-pyrrolo[2,1-c][1,4]benzodiazepin-10-yl)-methanone Oxalyl chloride (2.0 g) was added to a suspension of 4-fluoro-2-trifluoromethylbenzoic acid (2.0 g) in dichloromethane (25 ml). Two drops of dimethylformamide were added and the mixture was stirred for 18 hours at room temperature. The resultant solution was evaporated to dryness to give the crude acid chloride. This was redissolved in dichloromethane and filtered. Evaporation of this material gave a liquid which was then redissolved in hexane, filtered, and evaporated to yield the acid chloride as a pale yellow viscous liquid, which was used without further purification.

The acid chloride (2.26 g) in dichloromethane (25 ml) was added portionwise to a mixture of 10,11-dihydro-5H-pyrrolo[2,1-c][1,4]benzodiazepine (1.66 g), dichloromethane (10 ml), and diisopropylethylamine (1.30 g), cooled in an ice bath. After remaining at room temperature for 18 hours, the reaction mixture was washed with water and saturated aqueous sodium bicarbonate. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield 2.57 g of the title compound, m.p. 154–155° C.

EXAMPLE 2

[4-(3-Methyl-pyrazol-1-yl)-2-trifluoromethyl-phenyl](5H,11H-pyrrolo[2,1-c]-[1,4]benzodiazepin-10-yl)-methanone 60% Sodium hydride in oil (0.15 g) was washed with hexane and dry dimethylformamide (25 ml) was added, followed by 3-methylpyrazole (0.25 g). After hydrogen evolution ceased, (4-fluoro-2-trifluoromethyl-phenyl)(5H, 11H-pyrrolo[2,1-c][1,4]benzodiaxepin-10-yl)-methanone (1.0 g) was added. The reaction mixture was heated in a sand bath at 110° C. for 15 hours. The reaction mixture was poured onto ice and saturated saline solution was added. The precipitate was collected by filtration. The crude reaction product was dissolved in dichloromethane and filtered through a short column of hydrous sodium magnesium silicate and further eluted with several additional volumes of dichloromethane. The combined organic phase was concentrated on a hot plate with the gradual addition of hexane. After cooling, the crystals were collected by filtration to yield 0.77 g of a crude product. Further purification by additional filtration through a short column of hydrous sodium magnesium silicate, followed by the addition of hexane, yielded the title compound as a crystalline solid (0.66 g), m.p. 194–195° C.

EXAMPLE 3

[4-(4-Methyl-pyrazol-1-yl)-2-trifluoromethyl-phenyl]-(5H,11H-pyrrolo[2,1-c][1,4]benzodiazepin-10-yl)-methanone In the manner of Example 2, employing (4-fluoro-2-trifluoromethyl-phenyl)(5H,11H-pyrrolo[2,1-c][1,4]benzodiazepin-10-yl)-methanone (0.8 g), 60% sodium hydride in oil (0.15 g), 4-methylpyrazole (0.20 g) and dimethylformamide (25 ml), the product (0.47 g) was obtained as a colorless amorphous solid, MS, m/z: 437.3 $(M+H)^+$, 873.2 $(2M+H)^+$.

EXAMPLE 4

(4-Pyrazol-1-yl-2-trifluoromethyl-phenyl)-(5H,11H-pyrrolo[2,1-c][1,4]benzodiazepin-10-yl)-methanone In the manner of Example 2, employing (4-fluoro-2-trifluoromethyl-phenyl)-(5H,11H-pyrrolo[2,1-c][1,4]benzodiazepin-10-yl)-methanone (1.0 g), 60% sodium hydride in oil (0.20 g), pyrazole (0.25 g) and dimethylformamide (35 ml). The product (0.62 g) was obtained as a colorless amorphous solid, MS, m/z: 423.2 $(M+H)^+$, 445.2 $(M+Na)^+$, 845.3 $(2M+H)^+$.

EXAMPLE 5

[4-(3-Cyclopropyl-pyrazol-1-yl)-2-trifluoromethy-phenyl]-(5H,11H-pyrrolo[2,1-c][1,4]benzodiazepin-10-yl)-methanone In the manner of Example 2, employing (4-fluoro-2-trifluoromethyl-phenyl)-(5H,11H-pyrrolo[2,1-c][1,4]benzodiazepin-10-yl)-methanone (1.42 g), 60% sodium hydride in oil (0.20 g), 3-cyclopropylpyrazole (0.43 g) and dimethylformamide (50 ml), the product (1.22 g) was obtained as a crystalline solid, m.p. 163–164° C.

EXAMPLE 6

[4-(4-Methyl-imidazol-1-yl)-2-trifluoromethyl-phenyl]-(5H,11H-pyrrolo[2,1-c][1,4]benzodiazepin-10-yl)-methanone In the manner of Example 2, employing (4-fluoro-2-trifluoromethyl-phenyl)-(5H,11H-pyrrolo[2,1-c][1,4]benzodiazepin-10-yl)-methanone (1.0 g), 60% sodium hydride in oil (0.20 g), 4-methylimidazole (0.25 g) and dimethylformamide (25 ml), the title compound (0.66 g) was obtained as an amorphous solid. MS, m/z: 437.2 $(M+H)^+$, 873.2 $(2M+H)^+$.

EXAMPLE 7

(5H,11H-Pyrrolo[2,1-c][1,4]benzodiazepin-10-yl)-(4-[1,2,4]triazol-1-yl-2-trifluoromethylphenyl)-methanone In the manner of Example 2, employing (4-fluoro-2-trifluoromethyl-phenyl)-(5H,11H-pyrrolo[2,1-c][1,4]benzodiazepin-10-yl)-methanone (1.0 g), 60% sodium hydride in oil (0.20 g), 1,2,4-triazole (0.20 g), and dimethylformamide (25 ml), the title compound (0.36 g) was obtained as a colorless amorphous solid, MS, m/z: 424.2 (M+H)+, 847.3 (2M+H)+.

EXAMPLE 8

(2-Chloro-4-fluorophenyl)-(5H,11H-pyrrolo[2,1-c][1,4]benzodiazepin-10-yl)-methanone Oxalyl chloride (2.60 g) was added to a suspension of 2-chloro-4-fluorobenzoic acid (3.44 g) in dichloromethane (50 ml). Two drops of dimethylformamide were added and the mixture was stirred for 18 hours at room temperature. The resultant solution was evaporated to give the crude 2-chloro-4-fluorobenzoyl chloride as a viscous oil (3.72 g).

The crude 2-chloro-4-fluorobenzoyl chloride (3.68 g) in dichloromethane (25 ml) was added portionwise to a stirred, ice cooled solution of 10,11-dihydro-5H-pyrrolo[2,1-c][1,4]benzodiazepine (2.76 g), diisopropylethylamine (2.47 g) and dichloromethane (50 ml). After 18 hours at room temperature, the reaction mixture was washed with water and saturated aqueous sodium bicarbonate. The dichloromethane solution was dried with anhydrous sodium sulfate and filtered through a short column of hydrous magnesium silicate and further eluted with several volumes of dichloromethane. The combined organic phase was concentrated on a hot plate with the gradual addition of hexane until crystallization occurred. After cooling, the crystals were collected by filtration to yield the title compound (3.85 g), m.p. 110–112° C.

EXAMPLE 9

[2-Chloro-4-(3-methyl-pyrazol-1-yl)-phenyl]-(5H,11H)-pyrrolo[2,1-c][1,4]benzodiazepin-10-yl)-methanone (Isomer A) and [2-Chloro-4-(5-methyl-pyrazol-1-yl)-phenyl]-(5H,11H)-pyrrolo[2,1-c][1,4]benzodiazepin-10-yl)-methanone (Isomer B)

Method 1: To 60% sodium hydride in oil (0.3 g, degreased with hexane) in dimethylformamide (25 ml) was added 3-methylpyrazole (0.55 g). When the hydrogen evolution subsided, (2-chloro-4-fluorophenyl)-(5H,11H-pyrrolo[2,1-c][1,4]benzodiazepin-10-yl)-methanone (1.70 g) was added. The reaction mixture was heated for 18 hours in a sand bath (internal temperature 125° C.). The reaction mixture was then poured onto ice and further diluted with a saturated saline solution. The precipitated solid was recovered by filtration. The crude product was dissolved in dichloromethane, dried over anhydrous sodium sulfate, and then filtered through a short column of hydrous sodium magnesium silicate and further eluted with several volumes of dichloromethane. The combined eluate was refluxed on a hot plate with the gradual addition of hexane until an opaque solution was observed. On cooling an amorphous solid was obtained. On subjecting this material to a second column of hydrous sodium magnesium silicate and evaporation of the solvent in vacuo gave a mixture of regioisomers 9A and 9B in approximately a 9:1 ratio as an amorphous glass (1.11 g), MS, m/z: 403.2 (M+H)+.

Method 2: To a pre-cooled, stirred suspension of hexane-washed 60% sodium hydride (3.00 g) in dry dimethylformamide (250 ml) was added dropwise under nitrogen 3-methylpyrazole (5.50 g) at 0° C. The mixture was warmed to room temperature. After gas evolution ceased, 2-chloro-4-fluorophenyl)-(5H,11H-pyrrolo[2,1-c][1,4] benzodiazepin-10-yl)-methanone (17.0 g) was added as a solid, and the mixture heated to 130° C. for one hour. The reaction mixture was poured into ice water, a precipitate collected by filtration, and air-dried. The precipitate was dissolved in dichloromethane, dried over anhydrous sodium sulfate, and filtered through a short column of silica gel, eluting with ethyl acetate. The combined filtrate was evaporated in vacuo to a residual foam (18.5 g). Purification and separation of regioisomers by low pressure column chromatography on silica gel eluting with a gradient mixture of ethyl acetate-hexane (10:90 to 25:75), yielded two purified regioisomers:

Isomer A, [2-chloro-4-(3-methyl-pyrazol-1-yl)-phenyl]-(5H,11H)-pyrrolo[2,1-c][1,4]benzodiazepin-10-yl)-methanone (13.5 g), as a colorless amorphous solid; MS (EI), m/z: 402 (M)+. A sample (0.5 g) was crystallized from diethyl ether, followed by recrystallization from ethanol to yield regioisomer A (0.275 g) as a colorless, crystalline solid, m.p. 141–143° C.;

Isomer B, [2-chloro-4-(5-methyl-pyrazol-1-yl)-phenyl]-(5H,11H)-pyrrolo[2,1-c][1,4]benzodiazepin-10-yl)-methanone (1.93 g) as a colorless amorphous solid. A sample was crystallized from diethyl ether, followed by recrystallization from methanol to yield regioisomer B as colorless, needles (1.4 g), m.p. 160–163° C.; MS (EI), m/z: 402 (M)+, MS (+FAB), m/z: 403 (M+H)+.

EXAMPLE 10

[2-Chloro-4-(3-methyl-pyrazol-1-yl)-phenyl]-(5H, 11H)-pyrrolo[2,1-c][1,4]benzodiazepin-10-yl)-methanone Step a) 2-Chloro-4-(3-methylpyrazol-1-yl)benzonitrile: To a cooled (0° C.) suspension of sodium hydride (60% in oil; 2.0 g) in dimethylformamide (50 ml) was added 3-methylpyrazole (3.39 g) in portions. After hydrogen gas evolution ceased, 2-chloro-4-fluorobenzonitrile (5.17 g) was added and the mixture was stirred at room temperature for 18 hours. The mixture was poured onto ice, diluted with brine, and the resulting precipitate was collected by filtration. The crude product was dissolved in dichloromethane, filtered through a column of anhydrous sodium magnesium silicate, and crystallized by the addition of hexane. Recrystallization from ethanol gave 4.42 g of product, m.p. 148–150° C.

Step b) 2-Chloro-4-(3-methylpyrazol-1-yl)benzamide: A suspension of 2-chloro-4-(3-methylpyrazol-1-yl) benzonitrile (4.35 g) from step a in dimethyl sulfoxide (20 ml) containing potassium carbonate (0.40 g) was cooled in an ice bath. Hydrogen peroxide (30%, 2.4 ml) was added and the mixture was warmed to room temperature over 1 hour. The resultant precipitate was recovered by filtration and recrystallized from ethanol to yield 2.44 g of product as fine needles, m.p. 159–160° C.; MS, m/z: 235.9 (M+H)+.

Step c) 2-Chloro-4-(3-methylpyrazol-1-yl)benzoic Acid: A solution of 2-chloro-4-(3-methylpyrazol-1-yl)benzamide (1.09 g) from step b in aqueous 75% sulfuric acid (25 ml) was cooled in an ice bath and sodium nitrite (1.73 g) was added. The mixture was warmed to room temperature over 1 h and poured onto ice. The precipitate was collected by filtration and used directly in the next reaction.

Step d) [2-Chloro-4-(3-methyl-pyrazol-1-yl)-phenyl]-(5H-10,11-dihydro-pyrrolo[2,1-c][1,4]benzodiazepin-10-yl)-methanone: A mixture of 2-chloro-4-(3-methylpyrazol-1-yl)benzoic acid (0.69 g), dichloromethane (25 ml) from step c, oxalyl chloride (1.0 g), and 1 drop of dimethylformamide was stirred at room temperature for 18 hour. The mixture was concentrated, taken up in dichloromethane (25 ml), and added to a mixture of 10,11-dihydro-5H-pyrrolo[2,1-c][1,4]-benzodiazepine (0.51 g) in dichloromethane (25 ml) containing diisopropylethylamine (0.76 g). The mixture was stirred at room temperature for 18 h and washed with saturated aqueous sodium bicarbonate solution. The organic layer was dried over anhydrous sodium sulfate and filtered through a short column of anhydrous sodium magnesium silicate. The solution was concentrated and the resultant material was crystallized from diethyl ether to give 0.67 g of product, m.p. 137–138° C.; MS, m/z: 403.2 (M+H)+, 805.8 (2M+H)+.

EXAMPLE 11

[2-Chloro-4-(4-methyl-pyrazol-1-yl)-phenyl-(5H, 11H-pyrrolo[2,1-c][1,4]benzodiazepin-10-yl)-methanone In the manner of Example 9's Method 1, employing (2-chloro-4-fluorophenyl)-(5H,11H-pyrrolo[2,1-c][1,4] benzodiazepin-10-yl)-methanone (1.0 g), 60% sodium hydride in oil (0.3 g, degreased with hexane), 4-methylpyrazole (0.48 g) and dimethylformamide (25 ml), the title compound (0.74 g) was obtained as an amorphous solid, MS, m/z: 403.2 (M+H)+, 425.2 (M+Na)+, 805.3 (2M+H)+.

EXAMPLE 12

[2-Chloro-4-(4-methyl-imidazol-1-yl)-phenyl]-(5H, 11H-pyrrolo[2,1-c][1,4]benzodiazepin-10-yl)-methanone In the manner of Example 9's Method 1, employing (2-chloro-4-fluorophenyl)-(5H,11H-pyrrolo[2,1-c][1,4] benzodiazepin-10-yl)-methanone (1.0 g), 60% sodium hydride in oil (0.3 g, degreased with hexane), 4-methylimidazole (0.48 g), and dimethylformamide (25 ml), the title compound (0.38 g) was obtained as an amorphous solid, MS, m/z: 403.3 (M+H)+.

EXAMPLE 13

[2-Chloro-4-(3-trifluoromethyl-pyrazol-1-yl)-phenyl]-(5H,11H-pyrrolo[2,1-c][1,4]benzodiazepin-10-yl)-methanone In the manner of Example 9's Method 1, employing (2-chloro-4-fluorophenyl)-(5H,11H-pyrrolo[2,1-c][1,4] benzodiazepin-10-yl)-methanone (0.8 g), 60% sodium hydride in oil (0.25 g, degreased with hexane), 3-trifluoromethylpyrazole (0.61 g) and dimethylformamide (25 ml), the title compound was obtained as an amorphous solid, MS, m/z: 457.2 (M+H)+.

EXAMPLE 14

[2-Chloro-4-(1,2,4-triazol-1-yl)-phenyl]-(5H,11H-pyrrolo[2,1-c][1,4]benzodiazepin-10-yl)-methanone In the manner of Example 9's Method 1, employing (2-chloro-4-fluorophenyl)-(5H,11H-pyrrolo[2,1-c][1,4]

benzodiazepin-10-yl)-methanone (1.7 g), 60% sodium hydride in oil (0.5 g, degreased with hexane), 1,2,4-triazole (0.70 g) and dimethylformamide (50 ml), the title compound (0.51 g) was obtained as an amorphous solid, MS, m/z: 390.3 (M+H)+, 779.3 (2M+H)+.

EXAMPLE 15

(2-Chloro-4-pyrrol-1-yl-phenyl)-(5H,11H-pyrrolo[2,1-c][1,4]benzodiazepin-10-yl)-methanone In the manner of Example 9's Method 1, employing (2-chloro-4-fluorophenyl)-(5H,11H-pyrrolo[2,1-c][1,4] benzodiazepin-10-yl)-methanone (1.7 g), 60% sodium hydride in oil (0.3 g, degreased with hexane), pyrrole (0.42 g) and dimethylformamide (25 ml), the title compound (0.60 g) was obtained as an amorphous solid, MS, m/z: 388.2 (M+H)+.

EXAMPLE 16

(2-Chloro-4-pyrazol-1-yl-phenyl)(5H,11H-Pyrrolo[2,1-c][1,4]benzodiazepin-10-yl)-methanone In the manner of Example 9's Method 1, employing (2-chloro-4-fluorophenyl)-(5H, 11H-pyrrolo[2,1-c][1,4] benzodiazepin-10-yl)-methanone (1.0 g), 60% sodium hydride in oil (0.2 g, degreased with hexane), pyrazole (0.20 g) and dimethylformamide (25 ml), the title compound was obtained as an amorphous solid, MS, m/z: 389.2 (M+H)+, 777.1 (2M+H)+.

EXAMPLE 17

[2-Chloro-4-(1H-imidazol-1-yl)-phenyl)-(5H,11H-pyrrolo[2,1-c][1,4]benzodiazepin-10-yl)-methanone In the manner of Example 9's Method 1, employing (2-chloro-4-fluorophenyl)-(5H,11H-pyrrolo[2,1-c][1,4] benzodiazepin-10-yl)-methanone (2.0 g), 60% sodium hydride in oil (0.50 g, degreased with hexane), imidazole (0.50 g) and dimethylformamide (25 ml), the title compound (0.57 g) was obtained as a tan amorphous solid, MS, m/z: 389 (M+H)+.

EXAMPLE 18

[2-Chloro-4-(3-methylpyrazol-1-yl)-phenyl]-(3-methyl-5H,11H-pyrrolo[2,1-c][1,4]benzodiazepin-10-yl)-methanone Step a) 1-(5H,11H-Pyrrolo[2, 1-c][1,4]benzodiazepin-10-yl)-2,2,2-trifluoro-ethanone: To an ice cooled solution of 10,11-dihydro-5H-pyrrolo[2,1-c][1,4]-benzodiazepine (5.62 g) and diisopropylethylamine (4.0 g) in dichloromethane (75 ml) was added dropwise trifluoroacetic anhydride (7.0 g) in dichloromethane. The mixture was stirred at room temperature for 18 hours, and washed with water and saturated aqueous sodium bicarbonate. The organic phase was dried over anhydrous sodium sulfate and filtered through a short column of anhydrous sodium magnesium silicate. The combined organic phase was concentrated on a hot plate with the gradual addition of hexane until crystallization occurred. After cooling, the crystals were collected by filtration to yield 7.70 g of product as fine needles, m.p. 134–135° C., MS m/z: 281 (M+H)+.

Step b) 1-(3-Dimethylaminomethyl-5H,11H-pyrrolo[2,1-c][1,4]benzo-diazepin-10-yl)-2,2,2-trifluoroethanone. A mixture of 1-(5H,11H-pyrrolo[2,1-c][1,4]benzodiazepin-10-yl)-2,2,2-trifluoroetharione (2.80 g), ) from step a), bis-dimethylaminomethane (2.04 g), paraformaldehyde (2.70 g) and acetic acid (1.20 g) in a mixture of tetrahydrofuran (50 ml) and methanol (50 ml) and was stirred at room temperature for 18 hours. The mixture was concentrated in vacuo, water was added, and the aqueous mixture was extracted with dichloromethane. The combined extracts were dried over anhydrous sodium sulfate and filtered through a short column of anhydrous sodium magnesium silicate. The solution was concentrated in vacuo and the residue was crystallized from hexane to yield 2.05 g of the product as a colorless solid m.p. 109–110° C., MS m/z: 338.3 (M+H)+.

Step c) Trimethyl-(10-trifluoroacetyl-10,11-dihydro-5H-pyrrolo[2,1-c][1,4]benzodiazepin-3-yl-methyl)-ammonium iodide: A mixture of 1-(3-dimethylaminomethyl-5H,11H-pyrrolo[2,1-c][1,4]benzodiazepin-10-yl)-2,2,2-trifluoroethanone (1.83 g) from step b) and iodomethane (1.0 g) in dichloromethane (20 ml) was stirred at room temperature for 18 hours. Diethyl ether was added and the resulting precipitate was collected by filtration to give 2.54 g of product as a colorless solid, m.p. 140–155° C. (dec).

Step d) 10,11-Dihydro-3-methyl-5H-pyrrolo[2,1-c][1,4] benzodiazepine: Sodium borohydride (2.6 g) was added in two portions to a refluxing mixture of trimethyl-(10-trifluoroacetyl-10,11-dihydro-5H-pyrrolo[2,1-c][1,4] benzodiazepin-3-yl-methyl)-ammonium iodide (2.60 g) from step c) in ethanol. After 4 hours, the mixture was concentrated in vacuo. Water was added to the residue and the mixture was extracted with dichloromethane. The combined extracts were dried over anhydrous sodium sulfate and filtered through a short column of anhydrous sodium magnesium silicate. The solution was concentrated in vacuo and the residue was crystallized from hexane to yield 1.14 g of product, m.p. 150–151° C., MS m/z: 199.1 (M+H)+.

Step e) [2-Chloro-4-(3-methylpyrazol-1-yl)-phenyl]-(3-methyl-5H, 11H-pyrrolo[2,1-c][1,4]-benzodiazepin-10-yl)-methanone: A mixture of 2-chloro-4-(3-methylpyrazol-1-yl)-benzoic acid (0.18 g) from step d), oxalyl chloride (0.18 g) and one drop of dimethylformamide in dichloromethane (10 ml), was stirred at room temperature for 18 hours. The mixture was concentrated in vacuo, and the residue was redissolved in dichloromethane and reconcentrated in vacuo to yield 2-chloro-4-(3-methyl-pyrazol-1-yl)-benzoyl chloride. A slurry of the acid chloride in dichloromethane (25 ml) was added dropwise to a solution of 10,11-dihydro-3-methyl-5H-pyrrolo[2,1-c][1,4]benzodiazepine (0.12 g) and diisopropylethylamine (0.10 g) in dichloromethane (25 ml). The mixture was stirred at room temperature for 18 h, and washed with water and saturated aqueous sodium bicarbonate. The organic phase was dried over anhydrous sodium sulfate and filtered through a short column of anhydrous sodium magnesium silicate. The solution was concentrated in vacuo and triturated with diethyl ether to yield 0.115 g of product as colorless crystals, m.p. 178–180° C., MS m/z: 417.3 (M+H)+, 833.3 (2M+H)+.

EXAMPLE 19

(2-Chloro-4-trifluoromethyl-pyrimidin-5-yl)-(5H, 11H-pyrrolo[2,1-c][1,4]benzodiazepin-10-yl)-methanone 2-Chloro-4-(trifluoromethyl)pyrimidine-5-carbonyl chloride (2.57 g) was added gradually to an ice-cooled solution of 10,11-dihydro-5H-pyrrolo[2,1-c][1,4]-benzodiazepine, (1.84 g) and diisopropylethylamine (1.37 g) in dichloromethane (50 ml). After stirring at room temperature for 18 hours, the reaction mixture was washed with water and saturated aqueous sodium bicarbonate. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (3.22 g), m.p. 221–223

EXAMPLE 20

[2-(3-Methyl-pyrazol-1-yl)-4-trifluoromethyl-pyrimidin-5-yl]-(5H,11H-pyrrolo[2,1-c][1,4]benzodiazepin-10-yl)-methanone To 60% sodium hydride in oil (0.15 g, degreased with hexane) in dimethylformamide (25 ml) was added 3-methylpyrazole (0.25 g). When the hydrogen evolution subsided, (2-chloro-4-trifluoromethyl-pyrimidin-5-yl)-(5H,11H-pyrrolo[2,1-c][1,4]benzodiazepin-10-yl)-methanone (0.98 g) was added. The reaction mixture was heated for 18 hours in a sand bath (internal temperature 110° C.). The mixture was then poured onto ice and further diluted with a saturated saline solution. The precipitate was filtered, redissolved in dichloromethane and dried over anhydrous sodium sulfate. Purification was aided by filtration through a short column of hydrous sodium magnesium silicate and further elution with several volumes of dichloromethane. The combined eluate was concentrated on a hot plate with the gradual addition of hexane until crystallization occurred. After cooling, the solid was collected by filtration to yield the title compound (0.54 g) as colorless crystals, m.p. 202–204° C.

EXAMPLE 21

[2-(4-Methyl-pyrazol-1-yl)-4-trifluoromethyl-pyrimidin-5-yl]-(5H,11H-pyrrolo[2,1-c][1,4]benzodiazepin-10-yl)-methanone In the manner of Example 9's Method 1, employing (2-chloro-4-trifluoromethyl-pyrimidin-5-yl)-(5H,11H-pyrrolo[2,1-c][1,4]benzodiazepin-10-yl)-methanone (0.98 g), 60% sodium hydride in oil (0.15 g), 4-methylpyrazole (0.42 g) and dimethylformamide (25 ml), the title compound (0.73 g) was obtained as a crystalline solid, m.p. 214–217° C.

EXAMPLE 22

1-[4-(5H,11H-Pyrrolo[2,1-c][1,4]benzodiazepine-10-carbonyl)-phenyl]-ethanone

4-Acetylbenzoic acid (5.0 g) and thionyl chloride (10 ml) were heated on a steam bath under argon for 0.75 hour, and the volatile material was removed under reduced pressure. Toluene was added and the volatiles were removed again to give the crude acid chloride as a red-orange oil. This compound tended to solidify and was used as such for further transformations.

The acid chloride (4.56 g) in dichloromethane (25 ml) was added portionwise to an ice-cooled solution of 10,11-dihydro-5H-pyrrolo[2,1-c][1,4]-benzodiazepine (3.68 g) and diisopropylethylamine (3.25 g) in dichloromethane (100 ml). After stirring at room temperature for 18 hours, the reaction mixture was washed with water and saturated aqueous sodium bicarbonate. The dichloromethane solution was dried over anhydrous sodium sulfate and filtered through a short column of hydrous sodium magnesium silicate eluting with several volumes of dichloromethane. The combined organic phase was concentrated on a hot plate with the gradual addition of hexane until crystallization occurred. After cooling, the crystals were collected by filtration to yield the title compound (1.75 g), m.p. 135–137° C.

EXAMPLE 23

3-Dimethylamino-1-[4-(5H,11H-pyrrolo[2,1-c][1,4]benzodiazepine-10-carbonyl)-phenyl]-2-propen-1-one A reaction mixture of 1-[4-(5H,11H-pyrrolo[2,1-c][1,4]benzodiazepine-10-carbonyl)-phenyl]-ethanone (1.40 g), t-butoxy-bis-dimethylaminomethane (5.0 ml) and dichloromethane (10 ml) was stirred for 18 hours. The red-orange precipitate was filtered to yield the title compound (1.22 g), m.p. 203–205° C. Additional product (0.18 g) was isolated from the reaction mixture by concentration.

EXAMPLE 24

[4-(1H-Pyrazol-3-yl)-phenyl]-(5H,11H-pyrrolo[2,1-c][1,4]benzodiazepin-10-yl)-methanone A reaction mixture of 3-dimethylamino-1-[4-(5H,11H-pyrrolo[2,1-c][1,4]benzodiazepine-10-carbonyl)-phenyl]-2-prop-1-one (1.0 g), anhydrous hydrazine (0.20 g), and glacial acetic acid (20 ml) was refluxed for 7 hours and evaporated to dryness. The crude residue was dissolved in dichloromethane, washed with a saturated aqueous sodium bicarbonate solution and dried over anhydrous sodium sulfate. The solution was filtered through a short column of hydrous sodium magnesium silicate, eluting with several volumes of dichloromethane. The combined organic phase was concentrated on a hot plate with the gradual addition of hexane until crystallization occurred. After cooling, the crystals were collected by filtration. The column procedure was repeated to yield the title compound (0.65 g), m.p. 219–221° C.

EXAMPLE 25

[4-(1-Methyl-1H-pyrazolyl-3-yl)-phenyl]-(5H,11H-pyrrolo[2, 1-c][1,4]-benzodiazepin-10-yl)-methanone To a mixture of 60% sodium hydride in oil (0.35 g, degreased with hexane) and dimethylformamide (20 ml) was added [4-(1H-pyrazol-3-yl)-phenyl]-(5H,11H-pyrrolo[2,1-c][1,4]benzodiazepin-10-yl)-methanone (0.98 g) followed in a few minutes by iodomethane (0.50 g). The reaction mixture was stirred for 18 hours at room temperature and then poured into water and extracted with dichloromethane. After drying, the organic layer was filtered through a short column of hydrous sodium magnesium silicate, eluting with several volumes of dichloromethane. The combined organic phase was concentrated on a hot plate with the gradual addition of hexane until crystallization occurred. After cooling, the crystals were collected by filtration to yield the title compound (0.70 g), m.p. 194–195° C.

EXAMPLE 26

[4-(1-Ethyl-1H-pyrazol-3-yl)-phenyl]-(5H,11H-pyrrolo[2,1-c][1,4]-benzodiazepin-10-yl)-methanone In the manner of Example 25, employing [4-(1H-pyrazol-3-yl)-phenyl]-(5H,11H-pyrrolo[2,1-c][1,4]benzodiazepin- 10-yl)-methanone (1.0 g), 60% sodium hydride in oil (0.27 g), dimethylformamide (25 ml), and ethyl iodide (0.87 g), the title compound (0.69 g) was obtained as a crystalline solid, m.p. 180–183° C.

EXAMPLE 27

[4-(1-Propyl-1H-pyrazol-3-yl)-phenyl]-(5H,11H-pyrrolo[2,1-c][1,4]-benzodiazepin-10-yl)-methanone In the manner of Example 25, employing [4-(1H-pyrazol-3-yl)-phenyl]-(5H,11H-pyrrolo[2,1-c][1,4]benzodiazepin-10-yl)-methanone (0.98 g), 60% sodium hydride in oil (0.30 g), dimethylformamide (25 ml), and 1-iodopropane (0.60 g), the title compound (0.32 g) was obtained as a crystalline solid, m.p. 159–161° C.

EXAMPLE 28

[4-(1-Butyl-1H-pyrazol-3-yl)-phenyl]-(5H,11H-pyrrolo[2,1-c][1,4]-benzodiazepin-10-yl)-methanone In the manner of Example 25, employing [4-(1H-pyrazol-3-yl)-phenyl]-(5H,11H-pyrrolo[2,1-c][1,4]benzodiazepin-10-yl)-methanone (0.98 g), 60% sodium hydride in oil (0.30 g), dimethylformamide (25 ml), and 1-iodobutane (0.60 g), the title compound (0.32 g) was obtained as a crystalline solid, m.p. 122–123° C.

EXAMPLE 29

[4-(1-methoxymethyl-1H-pyrazol-3-yl)-phenyl]-(5H,11H-pyrrolo[2,1-c][1,4]-benzodiazepin-10-yl)-methanone In the manner of Example 25, employing [4-(1H-pyrazol-3-yl)-phenyl]-(5H,11H-pyrrolo[2,1-c][1,4]benzodiazepin-10-yl)-methanone (1.0 g), 60% sodium hydride in oil (0.15 g), dimethylformamide (25 ml), and iodomethyl methyl ether (0.50 g), the title compound (0.26 g) was obtained as an amorphous solid, MS, m/z: 399.2(M+H)+, 797.2 (2M+H)+.

EXAMPLE 30

1-{3-[4-(5H,11H-Pyrrolo[2,1-c][1,4]benzodiazepine-10-carbonyl)-phenyl]-pyrazol-1-yl}-ethanone To a solution of [4-(1H-pyrazol-3-yl)-phenyl]-(5H,11H-pyrrolo[2,1-c][1,4]-benzodiazepin-10-yl)-methanone (0.50 g) in dry pyridine (10 ml) was added acetic anhydride (0.20 g). After stirring at room temperature for 18 hours the reaction mixture was poured into water and the precipitate was collected by filtration. The crude product was dissolved in dichloromethane and dried over anhydrous sodium sulfate. This solution was filtered through a short column of hydrous sodium magnesium silicate, eluting with several additional volumes of dichloromethane. The eluant was concentrated on a hot plate with the gradual addition of hexane until crystallization occurred. After cooling, the crystals were collected by filtration to yield the title compound (0.46 g), m.p. 192–194° C.

EXAMPLE 31

1-{3-[4-(5H,11H-Pyrrolo[2,1-c][1,4]benzodiazepine-10-carbonyl)-phenyl]-pyrazol-1-yl}-propan-1-one In the manner of Example 30, employing [4-(1H-pyrazol-3-yl)-phenyl]-(5H,11H-pyrrolo[2,1-c][1,4]benzodiazepin-10-yl)-methanone (0.16 g) in dry pyridine (10 ml) and propionic anhydride (0.10 g), the title compound (0.17 g) was obtained as a crystalline solid, m.p. 150–152° C.

EXAMPLE 32

[4-(1-Cyclopropanecarbonyl-1H-pyrazol-3-yl)-phenyl]-(5H,11H-pyrrolo[2,1-c][1,4]benzodiazepin-10-yl)-methanone To a solution of [4-(1H-pyrazol-3-yl)-phenyl]-(5H,11H-pyrrolo[2,1-c][1,4]-benzodiazepin-10-yl)-methanone (1.0 g) in dry pyridine (10 ml) was added cyclopropanecarbonyl chloride (0.44 g). After stirring at room temperature for 18 hours the reaction mixture was poured into water and the precipitate was collected by filtration. The crude product was dissolved in dichloromethane and dried over anhydrous sodium sulfate. This solution was filtered through a short column of hydrous sodium magnesium silicate, eluting with several additional volumes of dichloromethane. The eluant was concentrated on a hot plate with the gradual addition of hexane until crystallization occurred. After cooling, the crystals were collected by filtration to yield the title compound (0.88 g) was obtained as a crystalline solid, m.p. 197–199° C.

EXAMPLE 33

1-{3-[4-(5H,11H-Pyrrolo[2,1-c][1,4]benzodiazepine-10-carbonyl)-phenyl]-pyrazol-1-yl}-butan-1-one In the manner of Example 32, employing [4-(1H-pyrazol-3-yl)-phenyl]-(5H,11H-pyrrolo[2,1-c][1,4]benzodiazepin-10-yl)-methanone (0.71 g) in dry pyridine (10 ml) and butyryl chloride (0.32 g), the title compound (0.54 g) was obtained as a solid, m.p. 105–110° C.; MS, m/z: 424 (M)+.

EXAMPLE 34

(5H,11-Pyrrolo[2,1-c][1,4]benzodiazepin-10-yl)-{4-[1-(thiophene-2-carbonyl)-1H-pyrazoly-3-yl]phenyl}-methanone In the manner of Example 32, employing [4-(1H-pyrazol-3-yl)-phenyl]-(5H,11H-pyrrolo[2,1-c][1,4]benzodiazepin-10-yl)-methanone (0.5 g) in dry pyridine (10 ml) and thiophene-2-carbonyl chloride (0.25 g), the title compound (0.41 g) was obtained as a crystalline solid, m.p. 195–197° C.; MS, m/z: 464 (M)+.

EXAMPLE 35

{4-[1-(5-Fluoro-2-methyl-benzoyl)-1H-pyrazol-3-yl]-phenyl}-(5H,11H-pyrrolo[2,1-c][1,4]benzodiazepin-10-yl)-methanone In the manner of Example 32, employing [4-(1H-pyrazol-3-yl)-phenyl]-(5H,11H-pyrrolo[2,1-c][1,4]benzodiazepin-10-yl)-methanone (0.35 g) in dry pyridine (10 ml) and 2-methyl-5-fluorobenzoyl chloride (0.22 g), the title compound (0.11 g) was obtained as an amorphous pale yellow solid, MS, m/z: 490 (M)+.

EXAMPLE 36

{4-[1-(2-Methyl-benzoyl)-1H-pyrazol-3-yl]-phenyl}-(5H,11H-pyrrolo[2,1-c][1,4]benzodiazepin-10-yl)-methanone In the manner of Example 32, employing [4-(1H-pyrazol-3-yl)-phenyl]-(5H,11H-pyrrolo[2,1-c][1,4]benzodiazepin- 10-yl)-methanone (0.71 g) in dry pyridine (20 ml) and o-toluyl chloride (0.39 g), the title compound (0.59 g) was obtained as a crystalline solid, m.p. 170–173° C.; MS, m/z: 472 (M)+.

EXAMPLE 37

{4-[1-(2-Chloro-4-fluoro-benzoyl)-1H-pyrazol-3-yl]-phenyl}-(5H,11H-pyrrolo[2,1-c][1,4]benzodiazepin-10-yl}methanone Portionwise, 2-chloro-4-fluorobenzoyl chloride (0.82 g) was added to a solution of [4-(1H-pyrazol-3-yl)-phenyl]-(5H,11H-pyrrolo[2,1-c][1,4]benzodiazepin-10-yl)-methanone (1.0 g) and diisopropylamine (0.55g) in dichloromethane (25 ml) which was cooled in an ice bath. The reaction mixture was allowed to stir at room temperature overnight. The reaction mixture was washed with water and saturated sodium bicarbonate and dried over anhydrous sodium sulfate. The dichloromethane solution was passed through a short column of hydrous sodium magnesium silicate, eluting several additional volumes of dichloromethane. The eluent was evaporated to dryness to yield 1.06 g of the product as a solid, m.p. 150–157° C.; MS, m/z: 510 (M)+.

EXAMPLE 38

{4-[1-(2,4-Dichloro-benzoyl)-1H-pyrazol-3-yl]-phenyl}-(5H,11H-pyrrolo[2,1-c][1,4]benzodiazepin-10-yl)-methanone In the manner of Example 32, employing [4-(1H-pyrazol-3-yl)-phenyl]-(5H,11H-pyrrolo[2,1-c][1,4]benzodiazepin-10-yl)-methanone (0.71 g) in dry pyridine (20 ml) and 2,4-dichlorobenzoyl chloride (0.52 g), the title compound (0.66 g) was obtained as a crystalline solid, m.p. 180–182° C.; MS, m/z: 528 (M)+.

EXAMPLE 39

2-(2,4-Dichloro-phenyl)-1-{3-[4-(5H,11H-pyrrolo[2,1-c][1,4]benzodiazepine-10-carbonyl)-phenyl]-pyrazol-1-yl}-ethanone In the manner of Example 32, employing [4-(1H-pyrazol-3-yl)-phenyl]-(5H,11H-pyrrolo[2,1-c][1,4]benzodiazepin-10-yl)-methanone (0.71 g) in dry pyridine (25 ml) and 2,4-dichlorophenylacetyl chloride (0.56 g), the title compound (0.20 g) was obtained as a crystalline solid, m.p. 130–140° C., resolidifies, m.p. 180–182° C.

EXAMPLE 40

{4-[1-(Biphenyl-2-carbonyl)-1H-pyrazol-3-yl]-phenyl}-(5H,11H-pyrrolo[2,1-c][1,4]benzodiazepin-10-yl)-methanone In the manner of Example 32, employing [4-(1H-pyrazol-3-yl)-phenyl]-(5H,11H-pyrrolo[2,1-c][1,4]benzodiazepin-10-yl)-methanone (0.71 g) in dry pyridine (20 ml) and 2-biphenylcarbonyl chloride (0.65 g), the title compound (0.49 g) was obtained as an amorphous solid, MS, m/z: 534 (M)+.

EXAMPLE 41

{4-[1-(4'-Trifluoromethyl-biphenyl-2-carbonyl)-1H-pyrazol-3-yl]-phenyl}-(5H,11H-pyrrolo[2,1-c][1,4]benzodiazepin-10-yl)-methanone In the manner of Example 32, employing [4-(1H-pyrazol-3-yl)-phenyl]-(5H,11H-pyrrolo[2,1-c][1,4]benzodiazepin-10-yl)-methanone (0.71 g) in dry pyridine (20 ml) and 4'-trifluoromethyl-2-biphenylcarbonyl chloride (0.71 g), the title compound (0.59 g) was obtained as an amorphous solid, MS, m/z: 602 (M)+.

EXAMPLE 42

3-Dimethylamino-1-[4-(5H,11H-pyrrolo[2,1-c][1,4]benzodiazepine-10-carbonyl)-phenyl]-2-buten-1-one A mixture of 1-[4-(5H,11H-pyrrolo[2,1-c][1,4]benzodiazepine-10-carbonyl)-phenyl]-ethanone (2.0 g) and dimethylacetamide dimethylacetal (15 ml) was refluxed in an inert atmosphere for 15 hours and the volatiles were removed at reduced pressure. The crude solid was dissolved in dichloromethane and filtered through a short column of hydrous sodium magnesium silicate followed by several volumes of dichloromethane. The combined eluant was concentrated and hexane was gradually added until crystallization occurred. The cooled solution was filtered to recover the title compound (1.03 g) as a crystalline solid, m.p. 183–185° C.

EXAMPLE 43

[4-(5-Methyl-1H-pyrazol-3-yl)-phenyl]-(5H,11H-pyrrolo[2,1-c][1,4]-benzodiazepin-10-yl)-methanone Anhydrous hydrazine (0.10 g) was added to a solution of 3-Dimethylamino-1-[4-(5H,11H-pyrrolo[2,1-c][1,4]benzodiazepine-10-carbonyl)-phenyl]-2-buten-1-one (0.50 g) in glacial acetic acid (25 ml). The reaction mixture was refluxed for 18 hours and then concentrated under vacuum. The solid was extracted with dichloromethane and washed with saturated aqueous sodium bicarbonate solution. The dichloromethane solution was dried over anhydrous sodium sulfate and filtered through a short column of hydrous sodium magnesium silicate and further eluted with several volumes of dichloromethane. The combined organic phase was concentrated on a steam bath with the gradual addition of hexane to give an opaque solution. After cooling the amorphous solid was recovered by filtration to yield the product (0.33 g), MS, m/z: 368 (M)+.

EXAMPLE 44

4-(5H,11H-Pyrrolo[2,1-c][1,4]benzodiazepine-10-carbonyl)-benzonitrile

4-Cyanobenzoic acid (5.0 g) and thionyl chloride (5.0 ml) were heated on a steam bath for one hour, and all of the volatiles were removed at reduced pressure. Hexane was added and the crude crystalline acid chloride (5.30 g) was recovered by filtration, and used without further purification.

To a reaction mixture of 10,11-dihydro-5H-pyrrolo[2,1-c][1,4]-benzodiazepine (3.68 g), dichloromethane (100 ml), and diisopropylethylamine (2.80 g) was added 4-cyanobenzoyl chloride (2.97 g). After remaining at room temperature for 18 hours, the reaction mixture was washed with water and saturated aqueous sodium bicarbonate solution. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (5.05) g, m.p. 184–186° C.

EXAMPLE 45

4-(5H,11H-Pyrrolo[2,1-c][1,4]benzodiazepine-10-carbonyl)-benzamide 4-(5H,11H-Pyrrolo[2,1-c][1,4]benzodiazepine-10-carbonyl)-benzonitrile (0.5 g) from Example 44 was added to concentrated sulfuric acid (5 ml) and the mixture was stirred for 18 hours at room temperature to yield a bright yellow solution. The solution was poured onto ice and made basic with the addition of concentrated ammonium hydroxide. The resultant solid was filtered, dissolved in dichloromethane, and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (5.05 g), m.p. 226–228° C.

EXAMPLE 46

N-(Dimethylaminomethylene)-4-(5H,11H-pyrrolo[2,1-c][1,4]benzodiazepine-10-carbonyl)-benzamide A mixture of 4-(5H,11H-pyrrolo[2,1-c][1,4]benzodiazepine-10-carbonyl)-benzamide (1.25 g) from Example 45 and dimethylformamide dimethylacetal (20 ml) was refluxed for 4 hours and the volatiles removed in vacuo to give a solid. The solid was dissolved in dichloromethane and filtered through a short column of hydrous sodium magnesium silicate and further eluted with several volumes of dichloromethane. The combined organic phase was concentrated on a steam bath with the gradual addition of hexane until crystallization occurred. After cooling, the crystals were collected by filtration to yield the title compound (1.40 g), m.p. 232–234° C.

EXAMPLE 47

N-(1-Dimethylaminoethylene)-4-(5H,11H-pyrrolo[2,1-c][1,4]benzodiazepine-10-carbonyl)-benzamide A mixture of 4-(5H,11H-pyrrolo[2,1-c][1,4]benzodiazepine-10-carbonyl)-benzamide (1.24 g) from Example 45 and dimethylacetamide dimethylacetal (5.0 ml) was heated on a steam bath for 4 hours. On cooling for 18 hours a crystalline solid precipitated which was recovered by filtration. The solid was washed with hexane to yield the product (1.54 g), m.p. 210–212° C.; MS, m/z: 400 (M)+.

EXAMPLE 48

(5H,11H-Pyrrolo[2,1-c][1,4]benzodiazepin-10-yl)-[4-(2H-[1,2,4]triazol-3-yl)-phenyl]-methanone A mixture of N-(dimethylaminomethylene)-4-(5H,1H-pyrrolo[2,1-c][1,4]-benzodiazepine-10-carbonyl)-benzamide (1.0 g) from Example 46, glacial acetic acid (15 ml), and anhydrous hydrazine (0.16 g) was refluxed for 15 hours and the volatiles removed in vacuo. Saturated aqueous sodium bicarbonate solution was added and the resultant solid was recovered by filtration. The solid was refluxed for 4 hours and the volatiles removed in vacuo to give a solid. The solid was dissolved in dichloromethane and filtered through a short column of hydrous sodium magnesium silicate and further eluted with several volumes of dichloromethane. The combined organic phase was concentrated on a steam bath with the gradual addition of hexane until crystallization occurred. After cooling, the crystals were collected by filtration to yield the title compound (0.39 g), m.p. 225–227° C.; MS, m/z: 355 (M)+.

EXAMPLE 49

[4-(2-Methyl-2H-[1,2,4]triazol-3-yl)-phenyl]-(5H,11H-pyrrolo[2,1-c][1,4]-benzodiazepin-10-yl)-methanone In the same manner as Example 48, employing N-(dimethylaminomethylene)-4-(5H,11H-pyrrolo[2,1-c][1,4]benzodiazepine-10-carbonyl)-benzamide (1.56 g) from Example 46 in glacial acetic acid (75 ml) and methylhydrazine (0.32 g), the title compound (0.10 g) was obtained as a solid, m.p. 155–158° C.; MS, m/z: 369 (M)+.

EXAMPLE 50

[4-(5-Methyl-2H-[1,2,4]triazol-3-yl)-phenyl]-(5H,11H-pyrrolo[2,1-c][1,4]-benzodiazepin-10-yl)-methanone In the same manner as Example 48, employing N-(1-dimethylaminoethylene)-4-(5H,11H-pyrrolo[2,1-c][1,4]benzodiazepine-10-carbonyl)-benzamide (1.00 g) from Example 47 in glacial acetic acid (75 ml) and anhydrous hydrazine (0.25 g), the title compound (0.20 g) was obtained as an amorphous solid, MS, m/z: 369 (M)+.

EXAMPLE 51

[4-(2,5-Dimethyl-2H-[1,2,4]triazol-3-yl)-phenyl]-(5H,11H-pyrrolo[2,1-c]-[1,4]benzodiazepin-10-yl)-methanone In the manner of Example 48, employing N-(1-dimethylaminoethylene)-4-(5H,11H-pyrrolo[2,1-c][1,4]benzodiazepine-10-carbonyl)-benzamide (1.18 g) from Example 47 in glacial acetic acid (75 ml) and methylhydrazine (0.30 g), the title compound (0.33 g) was obtained as a solid, m.p. 193–195° C.; MS, m/z: 383 (M)+.

EXAMPLE 52

[4-(3-Methyl[1,2,4]oxadiazol-5-yl)-phenyl]-(5H,11H-pyrrolo-[2,1-c][1,4]-benzodiazepin-10-yl)-methanone A solution of N-(1-dimethylaminoethylene)-4-(5H,11H-pyrrolo[2,1-c][1,4]-benzodiazepine-10-carbonyl)-benzamide (1.15 g) from Example 47 in glacial acetic acid (50 ml) containing hydroxylamine hydrochloride (0.40 g) and potassium acetate (1.0 g) was refluxed for 2 hours. All volatiles were removed under reduced pressure and a saturated aqueous solution of sodium bicarbonate was added. The mixture was extracted with dichloromethane and the extracts were dried over anhydrous sodium sulfate. The solution was filtered through a short column of hydrous sodium magnesium silicate and further eluted with several volumes of dichloromethane. The combined organic phase was concentrated on a steam bath with the gradual addition of hexane until crystallization occurred. After cooling, the crystals were collected by filtration to yield the title compound (0.38 g), m.p. 177–179° C.; MS, m/z: 371.3 (M)+, 741.3 (2M)+.

EXAMPLE 53

1-Methyl-4-(4-methylphenyl)-1H-pyrazole

A mixture of 2-(4-methylphenyl)-malondialdehyde (3.05 g), absolute ethanol (40 ml), and methylhydrazine (1.09 g) was stirred at room temperature for 18 hours and the volatiles removed at room temperature. Water was added and the mixture was extracted with dichloromethane. After drying over anhydrous sodium sulfate, the solution was filtered through a short column of hydrous sodium magnesium silicate and further eluted with several volumes of dichloromethane. The combined organic phase was concentrated on a steam bath with the gradual addition of hexane until crystallization occurred. After cooling, the crystals were collected by filtration to yield the title compound (2.91 g), m.p. 107–108° C.

EXAMPLE 54

4-(1-Methyl-1H-pyrazol-4-yl)-benzoic Acid

A mixture of 1-methyl-4-(4-methylphenyl)-1H-pyrazole (1.70 g), potassium permanganate (9.70 g), and 1 N sodium hydroxide (100 ml) was refluxed for 18 hours. The suspension was filtered through diatomaceous earth and cooled. The aqueous solution was extracted with dichloromethane which was discarded. The aqueous solution was acidified to pH 5.5. The resultant precipitate was difficult to filter and was thus extracted with dichloromethane. After evaporation of the solvent, the resulting solid was recrystallized from acetone to yield the title compound (0.60 g), m.p. 274–275° C.; MS m/z: 202 (M)+.

EXAMPLE 55

[4-(1-Methyl-1H-pyrazol-4-yl)-phenyl]-(5H,11H-pyrrolo[2,1-c][1,4]-benzodiazepin-10-yl)-methanone Oxalyl chloride (0.30 g) was added to a suspension of 4-(1-methyl-1H-pyrazol-4-yl)-benzoic acid (0.46 g) in dichloromethane (25 ml). Two drops of dimethylformamide were added and the mixture was stirred for 18 hours at room temperature. The resultant solution was evaporated to dryness to yield the crude acid chloride (0.57 g), which was utilized without further purification.

The acid chloride was added to a solution of 10,11-dihydro-5H-pyrrolo[2,1-c][1,4]-benzodiazepine (0.37 g) and diisopropylethylamine (0.58 g) in dichloromethane (50 ml). After 18 hours at room temperature, the reaction mixture was washed with water and saturated aqueous sodium bicarbonate. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (0.38 g), m.p. 200–201° C.; MS m/z: 368 (M)+.

EXAMPLE 56

6-(1-Methyl-1H-pyrazol-4-yl)-pyridine-3-carboxylic Acid

A suspension of 6-(1-formyl-2-hydroxyvinyl)pyridine-3-carboxylic acid (1.93 g) Eastman Chemicals) in absolute ethanol (50 ml) and methylhydrazine (0.50 g) was stirred for 18 hours at room temperature. The reaction mixture was filtered to give the product (1.30 g). The filtrate was evaporated to give a solid which was recrystallized from ethyl acetate to give an analytical sample of the title compound (0.55 g), m.p. 262–264° C.

EXAMPLE 57

[6-(1-Methyl-1H-pyrazol-4-yl)-pyridin-3-yl]-(5H, 11H-pyrrolo[2,1-c][1,4]-benzodiazepin-10-yl)-methanone A suspension of 6-(1-methyl-1H-pyrazol-4-yl)pyridine-3-carboxylic acid (0.48 g) in thionyl chloride (5.0 ml) was stirred at room temperature for 2 hours. The volatile material was removed under reduced pressure to afford 6-(1-methyl-1H-pyrazol-4-yl)pyridine-3-carbonyl chloride as a solid, which was utilized without further purification.

A solution of 10,11-dihydro-5H-pyrrolo[2,1-c][1,4] benzodiazepine (0.37 g) and diisopropylethylamine (0.61 g) in dichloromethane (25 ml) was cooled to 0° C. and a solution of 6-(1-methyl-1H-pyrazol-4-yl)pyridine-3-carbonyl chloride in dichloromethane (25 ml) was added portionwise. After 18 hours at room temperature, the reaction mixture was washed with water and a saturated aqueous sodium bicarbonate solution. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (0.31 g), m.p. 173–175° C.; MS, m/z: 370.3 (M+H)+.

EXAMPLE 58

[4-(Pyrazol-1-yl)-phenyl]-(5H,11H-pyrrolo[2,1-c][1,4]benzodiazepin-10-yl)-methanone To a suspension of 4-(pyrazol-1-yl)benzoic acid (1.56 g) in dichloromethane (25 ml) was added oxalyl chloride (1.04 g) and one drop of dimethylformamide. The mixture was stirred at room temperature for 18 hours to yield a clear solution. The volatile material was removed under reduced pressure to afford 4-(pyrazol-1-yl)benzoyl chloride as a pale yellow solid (1.58 g), which was utilized without further purification.

The 4-(pyrazol-1-yl)benzoyl chloride (0.75 g) was added to a solution of 10,11-dihydro-5H-pyrrolo[2,1-c][1,4] benzodiazepine (0.61 g) and diisopropylethylamine (0.47 g) in dichloromethane (25 ml). After 18 hours at room temperature, the reaction mixture was washed with water and a saturated aqueous sodium bicarbonate solution. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (0.90 g), m.p. 179–181° C.

EXAMPLE 59

[4-(3-Methyl-pyrazol-1-yl)-phenyl]-(5H,11H-pyrrolo [2,1-c][1,4]-benzodiazepin-10-yl)-methanone To a suspension of 4-(3-methylpyrazol-1-yl)benzoic acid (1.84 g) in dichloromethane (25 ml) was added oxalyl chloride (1.16 g) and one drop of dimethylformamide. The mixture was stirred at room temperature for 18 hours and the volatile material was removed under reduced pressure. Dichloromethane was added, the solution filtered, and the solvent evaporated under reduced pressure to yield 4-(3-methylpyrazol-1-yl)benzoyl chloride as a yellow oil (1.76 g), which was utilized without further purification.

The 4-(3-methylpyrazol-1-yl)benzoyl chloride was added to an ice-cooled solution of 10,11-dihydro-5H-pyrrolo[2,1-c][1,4]benzodiazepine (0.55 g) and diisopropylethylamine (0.44 g) in dichloromethane (25 ml). After stirring at room temperature for 18 hours, the reaction mixture was washed with water and a saturated aqueous sodium bicarbonate solution. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the title compound (0.90 g) was obtained as an amorphous solid, MS, m/z: 369 (M+H)$^+$.

EXAMPLE 60

[4-(4-Methyl-pyrazol-1-yl)-phenyl]-(5H,11H-pyrrolo [2,1-c][1,4]-benzodiazepin-10-yl)-methanone To a suspension of 4-(4-methylpyrazol-1-yl)benzoic acid (0.75 g) in dichloromethane (15 ml) was added oxalyl chloride (0.50 g) and one drop of dimethylformamide. The mixture was stirred at room temperature for 18 hours and the volatile material was removed under reduced pressure. The residue was dissolved in hexane and filtered through diatomaceous earth. Evaporation of the solvent in vacuo yielded 4-(4-methylpyrazol-1-yl)benzoyl chloride (0.77 g), which was used without further purification.

The 4-(4-methylpyrazol-1-yl)benzoyl chloride (0.72 g) was added to an ice-cooled solution of 10,11-dihydro-5H-pyrrolo[2,1-c][1,4]benzodiazepine (0.60 g) and diisopropylethylamine (0.48 g) in dichloromethane (25 ml). After stirring at room temperature for 18 hours, the reaction mixture was washed with water and saturated aqueous sodium bicarbonate. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (0.75 g), m.p. 179–181° C.; MS m/z: 369 (M+H)$^+$.

EXAMPLE 61

[4-(3,5-Dimethyl-pyrazol-1-yl)-phenyl]-(5H,11H-pyrrolo[2,1-c][1,4]-benzodiazepin-10-yl)-methanone To a suspension of 4-(3,5-dimethylpyrazol-1-yl)benzoic acid (1.34 g) in dichloromethane (25 ml) was added oxalyl chloride (1.0 g) and one drop of dimethylformamide. The mixture was stirred at room temperature for 18 hours and the volatile material was removed under reduced pressure. The residue was dissolved in hexane and filtered through diatomaceous earth. Evaporation of the solvent in vacuo yielded 4-(3,5-dimethylpyrazol-1-yl)benzoyl chloride (0.80 g), which was used without further purification.

The 4-(3,5-dimethylpyrazol-1-yl)benzoyl chloride (0.75 g) was added to an ice-cooled solution of 10,11-dihydro-5H-pyrrolo[2,1-c][1,4]benzodiazepine (0.55 g) and diisopropylethylamine (0.42 g) in dichloromethane (25 ml). After stirring at room temperature for 18 hours, the reaction mixture was washed with water and saturated aqueous sodium bicarbonate. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the title compound (0.79 g) was obtained as an amorphous solid, MS m/z: 383 (M+H)$^+$.

EXAMPLE 62

(5H,11H-Pyrrolo[2,1-c][1,4]benzodiazepin-10-yl)-[4-(3-trifluoromethyl-pyrazol-1-yl)-phenyl]-methanone A suspension of 4-(3-trifluoromethylpyrazolyl-1-yl) benzoic acid (1.45 g) in thionyl chloride (5.0 ml) was heated at reflux for 3 hours. The volatile material was removed under reduced pressure, the residue dissolved in dichloromethane, and filtered through diatomaceous earth. Evaporation of the solvent in vacuo yielded 4-(3-trifluoromethylpyrazol-1-yl)benzoyl chloride (1.45 g), which was used without further purification.

To a solution of 10,11-dihydro-5H-pyrrolo[2,1-c][1,4]-benzodiazepine (0.88 g) and diisopropylethylamine (0.66 g) in dichloromethane (50 ml) was added the 4-(3-trifluoromethylpyrazol-1-yl)benzoyl chloride (1.40 g). After stirring at room temperature for 18 hours, the reaction mixture was washed with water and saturated aqueous sodium bicarbonate. The dichloromethane solution was dried over anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (1.70 g), m.p. 166–167° C.; MS, m/z: 423.3 (M+H)$^+$, 845.4 (2M+H)$^+$.

EXAMPLE 63

[4-(Imidazol-1-yl)-phenyl]-(5H,11H-pyrrolo[2,1-c] [1,4]benzodiazepin-10-yl)-methanone A suspension of 4-(imidazol-1-yl)benzoic acid (0.90 g) in thionyl chloride (2.0 ml) was heated on a steam bath under argon for one hour. Evaporation of the volatile material under reduced pressure afforded a residue which crystallized upon the addition of hexane to yield the 4-(imidazol-1-yl) benzoyl chloride as the hydrochloride salt (1.17 g), m.p. 242–247° C.

To a solution of 10,11-dihydro-5H-pyrrolo[2,1-c][1,4]-benzodiazepine (0.75), diisopropylethylamine (1.20 g), and 4-dimethylaminopyridine (0.1 g) in dichloromethane (50 ml) was added 4-(imidazol-1-yl)benzoyl chloride hydrochloride (1.12 g). After stirring at room temperature for 18 hours, the reaction mixture was washed with water and saturated aqueous sodium bicarbonate. The dichloromethane solution was dried over anhydrous sodium sulfate, filtered through a short column of hydrous sodium magnesium silicate, and further eluted with several volumes of dichloromethane. The combined organic phase was concentrated on a hot plate with the gradual addition of hexane until crystallization occurred. After cooling, the crystals were collected by filtration to yield the title compound (0.57 g), m.p. 171–172° C.; MS, m/z: 354 (M+H)$^+$.

EXAMPLE 64

[4-(4-Methyl-imidazol-1-yl)-phenyl]-(5H,11H-pyrrolo[2,1-c][1,4]-benzodiazepin-10-yl)-methanone To a suspension of 4-(4-methylimidazol-1-yl)benzoic acid (0.80 g) in dichloromethane (25 ml) was added oxalyl chloride (0.50 g) and one drop of dimethylformamide. The mixture was stirred at room temperature for 18 hours and the volatile material was removed under reduced pressure to yield 4-(4-methylimidazol-1-yl)benzoyl chloride (1.02 g), which was utilized without further purification.

The 4-(4-methylimidazol-1-yl)benzoyl chloride (0.99 g) was added to an ice-cooled solution of 10,11-dihydro-5H-pyrrolo[2,1-c][1,4]benzodiazepine (0.64 g) and diisopropylethylamine (0.60 g) in dichloromethane (25 ml). After stirring at room temperature for 18 hours, the reaction mixture was washed with water and saturated aqueous sodium bicarbonate. The dichloromethane solution was dried over anhydrous sodium sulfate, filtered through a short column of hydrous sodium magnesium silicate, and further eluted with several volumes of dichloromethane. The combined organic phase was concentrated on a hot plate with the gradual addition of hexane until crystallization occurred. After cooling, the title compound (0.52 g) was obtained as a solid, m.p. 140–145° C.; MS, m/z: 369 (M+H)$^+$.

EXAMPLE 65

4-Bromo-2-chloro-benzoic Acid, Methyl Ester

Thionyl chloride (1.64 ml) was added dropwise to a suspension of 4-bromo-2-chlorobenzoic acid (6.92 g) in methanol, and heated to 60° C. for 2 hours. The solvent was removed in vacuo, the residue redissolved in ethyl acetate, and washed sequentially with 0.5 N sodium hydroxide (2×), water, and brine. The organic phase was dried over anhydrous sodium sulfate, and the solvent removed in vacuo to afford the title compound (7.8 g). $^1$H NMR (300 MHz), (DMSO-d$_6$) δ: 3.87 (s,3H), 7.68–7.9 (m, 3H).

EXAMPLE 66

2-Chloro-4-(3-dimethylamino-propyn-1-yl)benzoic Acid, Methyl Ester

To a stirred solution of 4-bromo-2-chlorobenzoic acid, methyl ester (18.69 g) in triethylamine (110 ml), was added 1-dimethylamino-2-propyne (12.1 ml), bis(triphenylphosphine)palladium(II) chloride (1.26 g), and copper(I) iodide (0.136 g). The mixture was heated slowly to 60° C., and the temperature maintained for one hour. The reaction was cooled to room temperature, filtered through diatomaceous earth, and the collected solid washed with ethyl acetate. The solvent was removed in vacuo, the resulting residue redissolved in ethyl acetate, and washed with water (3×). The combined organic extract was dried over anhydrous sodium sulfate, and the solvent removed in vacuo to give a crude product. The crude product was purified by column chromatography on silica gel (225 g), eluting with 40% ethyl acetate/hexane. After removing the solvent in vacuo, the title compound was obtained as a viscous oil (17.7 g), MS (+FAB), m/z: 252 (M+H)$^+$.

EXAMPLE 67

2-Chloro-4-(3-dimethylamino-2-propen-1-on-1-yl)-benzoic Acid, Methyl Ester

Gradually, 3-chloroperoxybenzoic acid (10.76 g) was added to a solution of 2-chloro-4-(3-dimethylamino-propyn-1yl)-benzoic acid, methyl -ester (15.07 g in dichloromethane (40 ml), at a rate to maintain the reaction temperature at –20° C. The mixture was stirred for 10–15 minutes. The resulting N-oxide was purified by chromatography on Activity Grade I basic alumina (215 g), eluting with 10% methanol/dichloromethane. The solvent was evaporated in vacuo between 12 to 18° C. The resulting residue was dissolved in methanol (100 ml) and heated at 60–65° C. with stirring for 18 hours. After removing the solvent in vacuo, and the product was purified by column chromatography on silica gel (190 g), eluting with 70% ethyl acetate/hexane. Trituration with diethyl ether containing some hexane afforded the title compound as a solid (5.68 g), m.p. 92–96° C.

EXAMPLE 68

2-Chloro-4-(1H-pyrazol-3-yl)-benzoic Acid, Methyl Ester

To a suspension of 2-chloro-4-(3-dimethylamino-2-propen-1-on-1-yl)-benzoic acid, methyl ester (13.67g) in ethanol (53 ml) was added hydrazine monohydrochloride (7.0 g). The mixture was heated in an oil bath at 75–80° C. for one hour. The solvent was removed in vacuo. The resulting residue was dissolved in ethyl acetate, washed with water and brine, dried over anhydrous sodium sulfate, and the solvent removed in vacuo to yield the title compound as a crude solid (12 g). A purified sample had a melting point of 130–131° C.

EXAMPLE 69

2-Chloro-4-(1-methyl-1H-pyrazol-3-yl)-benzoic Acid, Methyl Ester

To a suspension of hexane washed sodium hydride (3.05 g, 60% dispersion) in dimethylformamide (6 ml) under nitrogen was added a solution of 2-chloro-4-(1H-pyrazol-3yl)-benzoic acid, methyl ester (12.0 g) in dimethylformamide (30 ml) over a period of 15 minutes. The mixture was stirred at room temperature for 30 minutes. Iodomethane (9.5 ml) was added dropwise over 15 minutes. The mixture was allowed to stir at room temperature for 45 minutes. Additional iodomethane (5.16 ml) was added, and the reaction stirred another 75 minutes. The reaction was diluted with a small quantity of water, and concentrated in vacuo. The residue was diluted with water (500 ml) and extracted with a small quantity of ethyl acetate (5×). The combined organic phase was evaporated in vacuo to afford a crude product (13.48 g). The crude product was purified by column chromatography on silica gel (195 g) eluting with 15% ethyl acetate/hexane to afford the pure 1-methyl regioisomer (4.29 g), followed by a mixture of the 1-methyl and 2-methyl regioisomers (4.6 g). The mixture of isomers was triturated with hexane three times to give an additional sample of the pure 1-methyl regioisomer (2.55 g), m.p. 66.5–67° C.; MS (+FAB), m/z: 251 (M+H)$^+$.

EXAMPLE 70

2-Chloro-4-(1-methyl-1H-pyrazol-3-yl)-benzoic Acid

To a solution of 2-chloro-4-(1-methyl-1H-pyrazol-3-yl)-benzoic acid, methyl ester (6.85 g) in methanol (32 ml) was added 2.5 N sodium hydroxide solution (15.3 ml). The reaction was heated to 50° C. for one hour. The solvent was removed in vacuo, and the residue dissolved in water (250 ml), cooled in an ice bath, and acidified with 2N hydrochloric acid (24 ml). The resulting precipitate was filtered and dried to give a colorless solid (6.3 g) m.p. 232–233° C.; MS (+FAB), m/z: 236 (M+H)$^+$.

EXAMPLE 71

[2-Chloro-4-(1-methyl-1H-pyrazol-3-yl)-phenyl]-(5H,11H-pyrrolo[2,1-c]-[1,4]benzodiazepine-10-yl)-methanone Well powdered 2-chloro-4-(1-methyl-1H-pyrazol-3-yl)-benzoic acid (6.3 g) and dimethylformamide (2.16 ml) were suspended under nitrogen in a mixture of tetrahydrofuran (70 ml) and dichlormethane (15 ml). A solution of oxalyl chloride (2.43 ml) in dichloromethane (5 ml) was added dropwise, and the reaction stirred for one hour. The resulting suspension of 2-chloro-4-(1-methyl-1H-pyrazol-3-yl)-benzoyl chloride was utilized without further purification.

To a suspension of 10,11-dihydro-5H-pyrrolo[2,1-c][1,4]benzodiazepine (4.93 g) in dichloromethane (15 ml) was added diisopropylethylamine (7 ml). The suspension of the freshly prepared acid chloride was gradually added over 15 minutes under a positive flow of nitrogen. The slightly warm reaction mixture was stirred under nitrogen for 50 minutes. After stirring one hour, the mixture was concentrated in vacuo. The residue was dissolved in dichloromethane, washed with water, 5% sodium bicarbonate, and water. The organic phase was washed with brine, dried over anhydrous sodium sulfate, and the solvent removed in vacuo to give a crude product (10.95 g). The crude product was purified by column chromatography on silica gel (200 g), loading the column with 25% ethyl acetate/hexane. Less polar impurities were eluted with 25–30% ethyl acetate/hexane. The product was eluted with 30–40% ethyl acetate/hexane to afford a pure sample (7.42 g); which, after seeding with crystals, was triturated with diethyl ether containing some hexane for 24 hours. Filtration afforded the title compound as a crystalline solid (6.88 g), m.p. 148.5–150° C.; MS (EI), m/z: 402 (M)$^+$.

EXAMPLE 72

2-chloro-4-(2-methyl-1H-pyrazol-3-yl)-benzoic acid, methyl ester

The title compound was prepared in the same manner as described in Example 68, employing methyl-2-chloro-4-(3-dimethylamino-2-propene-1-one)-benzoate (0.8 g) and methylhydrazine (0.319 ml). The major 2-methyl regioisomer was isolated by column chromatography on silica gel, $^1$H NMR (300 MHz), (DMSO-d$_6$) δ: 3.87 (s, 3H), 3.89 (s, 3H), 6.58 (d, 1H), 7.5 (d, 1H) 7.62–7.93 (m, 3H).

EXAMPLE 73

2-Chloro-4-(2-methyl-1H-pyrazol-3-yl)-benzoic Acid

The title compound was prepared in the same manner as described in Example 70, employing 2-chloro-4-(2-methyl-1H-pyrazol-3yl)-benzoic acid, methyl ester (0.464 g) and 2.5N sodium hydroxide (1.04 ml). $^1$H NMR (300 MHz), (DMSO-d$_6$) δ: 3.89 (s, 3H), 6.56 (d, 1H), 7.49 (d, 1H), 7.59–7.90 (m, 3H)

EXAMPLE 74

[2-Chloro-4-(2-methyl-1H-pyrazol-3-yl)-pheny]-(5H,11H-pyrrolo[2,1-c][1,4]benzodiazepine-10-yl)-methanone The title compound was prepared in the same manner as described in Example 71, Employing 2-chloro-4-(2-methyl-1H-pyrazol-3yl)-benzoic acid (3.98 g) yielded the corresponding acid chloride, and acylation with 10,11-dihydro-5H-pyrrolo[2,1-c][1,4]benzodiazepine (0.293 g) yielded the title compound as a foam, m.p. 78–79° C.; MS (EI), m/z: 402 (M)$^+$.

EXAMPLE 75

2-Chloro-4-cyanobenzoic Acid, Methyl Ester 2-chloro-4-aminobenzoic acid, methyl ester (13.95 g) was suspended in a mixture of water (65 ml) and concentrated hydrochloric acid (15.7 ml). After stirring at room temperature for 10 minutes, the suspension was cooled to 0° C. A solution of sodium nitrite (5.71 g) in water (37 ml) was gradually added over 20 minutes, maintaining a reaction temperature of 0° C. After stirring at 0° C. for 35 minutes, the reaction mixture was partially neutralized by the addition of solid sodium carbonate (3.16 g) to afford a cold solution of the diazonium salt.

To a pre-cooled solution of copper(I) cyanide (8.4 g) and sodium cyanide (9.19 g) in water (112 ml) was gradually added the above solution of diazonium salt over a 45–50 minute period. The diazonium salt solution was maintained at 0° C. during the addition. The resulting mixture was stirred for 18 hours at room temperature. A precipitate was filtered, air-dried, dissolved in ethyl acetate (250 ml), and filtered to remove insoluble matter. The organic phase was dried over anhydrous magnesium sulfate, and the solvent removed in vacuo to afford a crude product as a brown solid (13.2 g). The crude product was purified by column chromatography on silica gel (250 g), eluting with 5–10% ethyl acetate/hexane to yield the title compound (10.9 g) as a solid, m.p. 90–92° C.; MS (EI), m/z: 195 (M)$^+$.

EXAMPLE 76

2-Chloro-4-cyanobenzoic Acid

To a stirred solution of 2-chloro-4-cyanobenzoic acid, methyl ester (24.3 g) in methanol (150 ml) was added 2.5N sodium hydroxide (54.5 ml). After stirring at room temperature. for 45 minutes, the solvent was removed in vacuo. The residue was dissolved in water, cooled in an ice bath, and made acidic with 2N hydrochloric acid (14 ml). The resulting precipitate was filtered and dried in vacuo to yield the title compound as a solid (22.55 g) m.p. 154–158° C.

EXAMPLE 77

3-Chloro-4-(5H,11H-pyrrolo[2,1-c][1,4]benzodiazepine-10-carbonyl)-benzonitrile

To a cooled suspension of 2-chloro-4-cyanobenzoic acid (9.1 g) in a mixture of dichloromethane (40 ml) and dimethylformamide (3.88 ml) was added dropwise a solution of oxalyl chloride (4.6 ml) in dichloromethane (10 ml) at 0° C. The stirred reaction was allowed to warm to room temperature over a one hour period. A cloudy solution of 2-chloro-4-cyanobenzoyl chloride was utilized without further purification.

To a stirred suspension of 10,11-dihydro-5H-pyrrolo[2,1-c][1,4]benzodiazepine (7.32 g) and diisopropylethylamine (13.6 ml) in dichloromethane (35 ml) was added under nitrogen the cloudy solution of 2-chloro-4-cyanobenzoyl chloride. After one hour at room temperature, the mixture was diluted with dichloromethane and washed sequentially with water, 5% sodium bicarbonate, and 50% saturated brine, After drying over anhydrous sodium sulfate, the solvent was removed in vacuo to afford a crude product (18.0 g). Purification by column chromatography on silica gel (250 g), eluting with 20% ethyl acetate/hexane, followed by 25% ethyl acetate/hexane, yielded the title compound (13.56 g) as a straw yellow foam, MS (EI), m/z: 347 (M)$^+$.

EXAMPLE 78

3-Chloro-4-(5H,11H-Pyrrolo[2,1-c][1,4]benzodiazepine-10-carbonyl)-benzoic Acid

To a suspension of 3-chloro-4-(5H,11H-pyrrolo-[2,1-c][1.4]-benzodiazepine-10-carbonyl)-benzonitrile (90.72 g) in ethanol was added 10 N sodium hydroxide (1.02 ml) and the mixture heated under reflux for two hours. The solvent was removed in vacuo, the residue dissolved in water, and made acidic with 2 N hydrochloric acid (4.7 ml). The resulting precipitate was extracted with ethyl acetate, and the organic phase dried over anhydrous sodium sulfate. After removing the solvent in vacuo, a foam was triturated with diethyl ether for 18 hours and filtered to give a crude product (0.69 g). The crude product was purified by treatment with activated charcoal in methanol. Crystallization from methanol/ether afforded the title compound as a purified solid (0.29 g), m.p. 198–199° C.; MS (EI), m/z: 366 (M)+.

EXAMPLE 79

3-Chloro-4-(5H,11H-pyrrolo[2,1-c][1,4] benzodiazepine-10-carbonyl)-benzamide

Concentrated sulfuric acid (70 ml) was added to 3-chloro-4-(5H,11H-pyrrolo-[2,1-c][1.4]benzodiazepine-10-carbonyl)-benzonitrile (12.85 g). The mixture was stirred at 60° C. for 3 hours, followed by stirring at room temperature for 18 hours. The reaction mixture was poured over ice and neutralized at 0° C., with 30% ammonium hydroxide (184 ml). The resulting suspension was extracted with ethyl acetate. The aqueous mixture was filtered, and reextracted with ethyl acetate. The combined organic phase was dried over anhydrous sodium sulfate, and the solvent removed in vacuo. The residue was triturated with a mixture of diethyl ether (50–60 ml) and a small quantity of ethyl acetate. Filtration of the precipitate afforded the title compound as a crystalline solid (10.44 g), m.p. 211–212° C.; MS (EI), m/z: 365 (M)+.

EXAMPLE 80

N-(1-Dimethylaminoethylene)-3-chloro-4-(5H,11H-pyrrolo[2,1-c][1,4]-benzodiazepine-10-carbonyl)-benzamide A suspension of 3-chloro-4-(5H,11H-pyrrolo[2,1-c][1,4] benzodiazepine-10-carbonyl)-benzamide (5.48 g) and dimethylacetamide dimethyl acetal (10.97 ml) was heated at 90° C. for 20 minutes. The excess reagent was removed under reduced pressure, and the title compound utilized without further purification, MS (EI), m/z: 434 (M)+.

EXAMPLE 81

[2-Choro-4-(5-methyl-2H-[1,2,4]triazol-3-yl) phenyl]-(5H,11H-pyrrolo[2,1-c][1,4]benzodiazepine-10-carbonyl)-methanone To a solution of N-(1-dimethylaminoethylene)-3-chloro-4-(5H,11H-pyrrolo[2,1-c][1,4]-benzodiazepine-10-carbonyl)-benzamide (3.01 g) in acetic acid (4 ml) was added a solution of anhydrous hydrazine (0.435 ml) in acetic acid (4 ml). The reaction mixture was stirred at between 85–90° C. for 45 minutes. After removing the acetic acid in vacuo, the reaction mixture was diluted with water (3540 ml), neutralized to pH 7.0 with aqueous sodium bicarbonate, and extracted with ethyl acetate. The organic extract was washed with brine, dried over anhydrous sodium sulfate, and the solvent removed in vacuo to afford a crude product (2.68 g). Purification of the crude product by column chromatography on silica gel (45 g), eluting with 70% ethyl acetate/hexane, afforded a purified product (2.5 g), which, after trituration with diethyl ether, yielded the title compound as a solid (2 g), m.p. 211–212° C.; MS (EI), m/z: 403 (M)+.

EXAMPLE 82

N-(Dimethylaminomethylene)-3-chloro-4-(5H,11H-pyrrolo[2,1-c][1,4]benzodiazepine-10-carbonyl)-benzamide The title compound was prepared in the same manner as described in Example 80, employing 3-chloro-4-(5H,11H-pyrrolo[2,1-c][1,4]benzodiazepine-10-carbonyl)-benzamide (1.83 g) and dimethylformamide dimethylacetal (5.3 ml), MS (EI), m/z::420 (M)+.

EXAMPLE 83

[2-Chloro-4-(2H-1,2,4-triazol-3-yl)-phenyl]-(5H, 11H-pyrrolo[2,1-c][1,4]-benzodiazepin-10-yl)-methanone The title compound was prepared in the same manner as described in Example 81, employing N-(dimethylaminomethylene)-3-chloro-4-(5H,11H-pyrrolo [2,1-c[1,4]benzo-diazepine-10-carbonyl)-benzamide (2.53 g) and hydrazine (0.38 ml), m.p. 174–177° C.; MS (EI), m/z: 389 (M)+.

EXAMPLE 84

[2-Chloro-4-(2-methyl-2H-[1,2,4]triazol-3-yl)-phenyl]-(5H,11H-pyrrolo [2,1-c][1,4]benzodiazepin-10-carbonyl)-methanone The title compound was prepared in the same manner as described in Example 48, using N-(dimethylaminomethylene)-3-chloro-4-(5H,11H-pyrrolo [2,1-c[1,4]benzodiazepin-10-carbonyl)-benzamide (0.572 g), and methylhydrazine (0.149 ml). m.p. 141–143° C. MS (EI): 403 (M)+.

EXAMPLE 85

4-[(2,5-Dimethyl-2H-[1,2,4]triazol-3-yl)-2-chloro-phenyl]-(5H,11H-pyrrolo[2,1-c][1,4]benzodiazepin-10-carbonyl)-methanone The title compound was prepared in the same manner as described in Example 48, using N-(1-dimethylaminoethylene)-3-chloro-4-(5H,11H-pyrrolo[2,1-c][1,4]-benzodiazepin-10-carbonyl)-benzamide (0.51 g) and methylhydrazine (0.125 ml). m.p. 197–199° C. MS (EI): 417 (M)+.

EXAMPLE 86

[2-Chloro-4-(1H-tetrazol-5-yl)-phenyl]-(5H,11H-pyrrolo[2,1-c][1,4]benzodiazepin-10-yl)-methanone To a solution of 3-chloro-4-(5H,11H-pyrrolo[2,1-c][1,4]-benzodiazepine-10-carbonyl)-benzonitrile (0.348 g) in dimethylformamide (2 ml) was added sodium azide (0.078 g) and ammonium chloride (0.065 g). The mixture was heated to 100° C. for 18 hours.

Most of the dimethylformamide was removed in vacuo. The residue dissolved in water (approximately 8 ml) and basified to pH 9.0 with 2.5N sodium hydroxide (0.6 ml) and extracted with ethyl acetate. The aqueous extract was acidified with 2N hydrochloric acid (1.1 ml), reextracted with ethyl acetate, dried over anhydrous sodium sulfate and the solvent removed in vacuo to give crude product (0.350 g) as an oil. The oily product was triturated with diethyl ether, filtered through acid treated silica gel, and eluted with 40% ethyl acetate/hexane to give purer sample. This was further triturated with diethyl ether, and filtered to give a sample (0.88 g) m.p. 218–220° C. MS (+FAB) 391 (M+H)+.

EXAMPLE 87

[2-Chloro-4-(3-methyl-pyrazol-1-yl)-phenyl]-(3-dimethylaminomethyl-5H,11H-pyrrolo[2,1-c][1,4] benzodiazepin-10-yl)-methanone To a stirred solution of [2-chloro-4-(3-methyl-pyrazol-1-yl)-phenyl]-(5H,11H-pyrrolo-[2,1-c][1,4]benzodiazepin-10- yl)-methanone (1.61 g), N, N, N', N', tetramethyldiamino-methane (0.82 g), and glacial acetic acid (0.48 g) in methanol (25 ml) was added a solution of 37% aqueous formaldehyde (4 ml). The mixture was warmed to 40° C. for 10 minutes. After stirring one hour at room temperature, the reaction was concentrated in vacuo, redissolved in dichloromethane, and extracted sequentially with aqueous sodium bicarbonate and water (4×). The organic phase was dried over anhydrous sodium sulfate, and filtered through a plug of silica gel, eluted with ethyl acetate. Evaporation of the solvent in vacuo afforded an oil, which on trituration with hexane yielded 0.36 g of the title compound as a colorless powder, m.p. 100–102° C.; MS (+FAB), m/z: 482 (M+Na)$^+$, 460 (M+H)$^+$.

EXAMPLE 88

(3-Bromo-5H,11H-pyrrolo[2,1-c][1,4]benzodiazepin-10-yl)-[2-chloro-4-(3-methyl-pyrazol-1-yl)-phenyl]-methanone To a stirred pre-cooled solution of [2-chloro-4-(3-methyl-pyrazol-1-yl)-phenyl]-(5H,11H-pyrrolo[2,1-c][1,4]benzodiazepin-10-yl)-methanone (1.61 g) in dichloromethane (25 ml) was added solid N-bromosuccinimide (0.712 g) over 10 minutes at −78° C. The reaction was allowed to warm to −40° C. over thirty minutes. The mixture was diluted with dichloromethane, and extracted sequentially with saturated aqueous sodium bicarbonate (2×100 ml) and water (100 ml). The organic phase was dried over anhydrous sodium sulfate, filtered through a plug of silica gel, and evaporated in vacuo to a residue. Crystallization from diethyl ether yielded 1.47 g of the title compound as a colorless solid, m.p. 148–149° C. (dec); MS (EI), m/z: 480 (M)$^+$.

EXAMPLE 89

(4-Bromo-2-chlorophenyl)-(5H,11H-pyrrolo[2,1-c][1,4]benzodiazepin-10-yl)-methanone Dimethylformamide (1 drop) was added to a solution of 4-bromo-2-chlorobenzoic acid (2.20 g) in anhydrous tetrahydrofuran (20 ml). Oxalyl chloride (1.46 g) was added and the mixture was warmed to reflux. The resultant solution was cooled to ambient temperature before being evaporated to dryness to give crude 4-bromo-2-chlorobenzoyl chloride as a gold viscous liquid, which was used without further purification.

To a mixture of 10,11-dihydro-5H-pyrrolo[2,1-c][1,4]-benzodiazepine (1.44 g) and triethylamine (0.95 g) in dichloromethane (40 ml), cooled in an ice bath, was added dropwise a solution of 4-bromo-2-chlorobenzoyl chloride (2.42 g) in dichloromethane (20 ml). The cooling bath was removed and after stirring for 22 hours, the reaction mixture was washed sequentially with water, saturated aqueous sodium bicarbonate, 0.5 N hydrochloric acid and water. The dichloromethane solution was dried over anhydrous sodium sulfate, filtered, then evaporated in vacuo to dryness to yield an off-white foam. Purification by flash chromatography on silica gel eluting with hexane-ethyl acetate (2:1) resulted in a white foam (3.02 g), m.p. 77–80° C., MS m/z: 400 (M)$^+$.

EXAMPLE 90

[2-Bromo-4-(3-methyl-pyrazol-1-yl)-phenyl]-(5H,11H)-pyrrolo[2,1-c][1,4]benzodiazepin-10-yl)-methanone Step a) 4-Fluoro-2-bromobenzoyl chloride: Dimethylformamide (2 drops) was added to a solution of 4-fluoro-2-bromobenzoic acid (4.91 g) in anhydrous tetrahydrofuran (55 ml). Oxalyl chloride (3.41 g) was added and the mixture was warmed to reflux. The resultant solution was cooled to room temperature, evaporated in vacuo to give the crude acid chloride as a gold viscous liquid, which was used without further purification.

Step b) (4-Fluoro-2-bromophenyl)-(5H,11H-pyrrolo[2,1-c][1,4]benzo-diazepin-10-yl)-methanone: A solution of 4-fluoro-2-bromobenzoyl chloride (5.32 g) from step a), in dichloromethane (35 ml), was added dropwise to a solution of 10,11-dihydro-5H-pyrrolo[2,1-c][1,4]-benzodiazepine (3.44 g) and triethylamine (2.27 g) in dichloromethane (80 ml) and cooled in an ice bath. The cooling bath was removed and after stirring for 16 hours, the reaction mixture was washed sequentially with water, saturated aqueous sodium bicarbonate and saturated aqueous sodium chloride. The dichloromethane solution was dried over anhydrous magnesium sulfate, filtered and evaporated in vacuo to give a pale purple foam. Purification by flash chromatography on silica gel eluting with hexane-ethyl acetate (1:1) resulted in the intermediate (4-fluoro-2-bromophenyl)-(5H,11H-pyrrolo[2,1-c][1,4]benzodiazepin-10-yl)-methanone as a tan foam (6.91 g), MS m/z: 384 (M)$^+$. This material was used without further purification in the next step.

Step c) [2-Bromo-4-(3-methyl-pyrazol-1-yl)-phenyl]-(5H,11H)-pyrrolo[2,1-c][1,4]benzodiazepin-10-yl)-methanone: A dispersion of 60% sodium hydride in oil (0.20 g) was washed with hexane, and then suspended in dimethylformamide (15 ml). To this suspension was added 3-methylpyrazole (0.41 g). When hydrogen gas evolution subsided, (4-fluoro-2-bromophenyl)-(5H,11H-pyrrolo[2,1-c][1,4]benzo-diazepin-10-yl)-methanone (1.74 g) from step b) was added. The reaction mixture was heated to 130° C. for 6 hours. After the reaction mixture was cooled to room temperature, poured into a 50% saturated aqueous sodium chloride solution and extracted with ethyl acetate. The ethyl acetate solution was dried over anhydrous magnesium sulfate, filtered and evaporated in vacuo to afford a brown oil. Purification by flash chromatography on silica gel eluting with hexane-ethyl acetate (1:1) gave a colorless solid (0.75 g). Recrystallization from methanol gave an off-white crystalline solid (0.53 g), m.p. 141–142.5° C., MS m/z: 446 (M)$^+$.

EXAMPLE 91

(2,4-Difluoro-phenyl)-(5H,11H-pyrrolo[2,1-c][1,4]benzodiazepin-10-yl)-methanone

Step a) 2,4-Difluorobenzoyl chloride: A suspension of 2,4-difluorobenzoic acid (3.6 g) containing a few drops of dimethylformamide in dichloromethane (40 ml) was treated dropwise under nitrogen with oxalyl chloride (2.4 ml). After gas evolution subsided, the reaction mixture was refluxed for an additional 15 minutes. The solution was evaporated to dryness in vacuo and the residue was utilized without further purification.

Step b) (2,4-Difluorophenyl)-(5H,11H-pyrrolo[2,1-c][1,4]benzodiazepin-10-yl)-methanone: To a solution of the crude 2,4-difluorobenzoyl chloride acid chloride of Step a in dichloromethane under nitrogen was added solid 10,11-dihydro-5H-pyrrolo[2,1-c][1,4]benzodiazepine amine (2.0 g) and diisopropylethylamine (3.4 ml). The reaction mixture turned yellow-orange. After stirring at room temperature for 10 the reaction mixture was washed with water, 1 N hydrochloric acid, 1 N sodium hydroxide and brine. The organic phase was dried over anhydrous sodium sulfate and evaporated to dryness to give a brown solid. The crude product was purified by column chromatography on silica gel (Merck-60) with 20% ethyl acetate-hexane to provide 2.9 g of the title compound as a white foam. MS (EI, m/z): 324 (M)$^+$.

EXAMPLE 92

[2-Fluoro-4-(3-methyl-pyrazol-1-yl)-phenyl]-(5H, 11H-pyrrolo[2,1-c][1,4]-benzodiazepin-10-yl)-methanone A suspension of hexane washed 60% sodium hydride (0.31 g) in dry dimethylformamide was treated dropwise with 3-methylpyrazole (0.62 ml) under nitrogen at room temperature. Stirring was continued until the gas evolution subsided (10 minutes). In one portion (2,4-difluorophenyl)-(5H,11H-pyrrolo[2,1-c][1,4]benzodiazepin-10-yl)-methanone (2.5 g) from step b) of Example 91 was added and stirring was continued until a clear solution was attained. The mixture was heated in a preheated oil bath at 130° C. for one hour. After cooling, the mixture was partitioned between water and ethyl acetate. The organic extracts were dried over anhydrous sodium sulfate and evaporated to dryness. The crude product was purified by flash column chromatography on silica gel (Merck-60) eluting with 20% ethyl acetate -hexane to yield 0.82 g of the title product as a foam which was crystallized by sonication from ethanol/hexane, m.p. 192–193° C. MS (EI) m/z: 386 (M)$^+$.

EXAMPLE 93

Methyl 4-(3-Methyl-pyrazol-1-yl)-2-trifluoromethyl-benzoate

Step a) Methyl 4-fluoro-2-trifluoromethylbenzoate: A suspension of 4-fluoro-2-trifluoromethylbenzoic acid (25.6 g) and a few drops of dimethylformamide in dichloromethane (250 ml) was treated dropwise under nitrogen with oxalyl chloride (11.3 ml). After gas evolution subsided, the reaction mixture was refluxed for an additional 15 minutes. The reaction was cooled and methanol (50 ml) was added. After stirring for 2 hours, the reaction was concentrated in vacuo, and the residue was partitioned between dichloromethane and water. The organic phase was washed with saturated sodium bicarbonate, dried over anhydrous sodium sulfate, and evaporated to dryness to give 18.0 g of the title compound as a golden oil. MS, (EI) m/z: 222 (M)$^+$.

The aqueous layer was acidified with 2 N hydrochloric acid to give a colorless solid which was collected by filtration to give 7.5 g of the starting benzoic acid.

Step b) Methyl 4-(3-methyl-pyrazol-1-yl)-2-trifluoromethyl-benzoate: A suspension of hexane washed 60% sodium hydride (3.85 g) in dry dimethylformamide (150 ml) was treated with the dropwise addition of a solution of 3-methylpyrazole (7.75 ml) in dimethylformamide (50 ml) under nitrogen at room temperature. Stirring was continued until the gas evolution subsided (10 minutes). A solution of methyl 4-fluoro-2-trifluoromethylbenzoate (17.8 g) from step a) in dimethylformamide (50 ml) was added dropwise to the clear solution. After stirring for 30 min. at room temperature the reaction was quenched with saturated ammonium chloride and extracted with ethyl acetate. The organic extracts (3×) were dried over anhydrous sodium sulfate and evaporated to dryness. The crude product was purified by flash column chromatography on silica gel (Merck 60) with a dichloromethane-hexane gradient (50%–75%) to give 13.6 g of the title product as a colorless solid. m.p. 59–61° C. MS (EI, m/z): 284 (M)$^+$.

EXAMPLE 94

4-(3-Methyl-pyrazol-1-yl)-2-trifluoromethyl-benzoic Acid

Methyl 4-(3-methyl-pyrazol-1-yl)-2-trifluoromethyl-benzoate (1.19 g) from Example 93, step b) was dissolved in methanol (10 ml) and a solution of 2.5 N sodium hydroxide (3.3 ml) was added. The reaction was heated at reflux for 90 minutes, cooled to room temperature and concentrated in vacuo to dryness. The residue was partitioned between ethyl acetate and 1 N hydrochloric acid. The combined organic extracts were dried over anhydrous sodium sulfate and concentrated in vacuo to give 1.14 g of the title compound as a colorless solid. MS (FAB) m/z: 271 (M+H)$^+$.

EXAMPLE 95

[4-(3-Methylpyrazol-1-yl)-2-trifluoromethylphenyl]-(5H,11H-pyrazolo[5,1-c]-[1,4]benzodiazepin-10-yl)-methanone A solution of 4-(3-methyl-pyrazol-1-yl)-2-trifluoromethylbenzoic (0.26 g) from Example 94 in tetrahydrofuran (5 ml) was treated with dimethylformamide (0.020 ml) followed by oxalyl chloride (0.090 ml). The solution was stirred at room temperature until gas evolution stopped and then the solution was warmed to reflux for 10 minutes. The sample was cooled to room temperature, concentrated to a solid and the solid was dissolved in tetrahydrofuran (25 mL) this solution was added to a solution (5H-10,11-dihydropyrazolo [5,1-c][1,4]benzodiazepine (0.143 g) and triethylamine (0.150 ml) in tetrahydrofuran (20 ml). The solution was stirred overnight at room temperature. A precipitate formed. The sample was diluted with dichloromethane to dissolve the precipitate and then the sample was concentrated in vacuo to about ⅓ of the original volume. The sample was partitioned between dichloromethane and saturated aqueous ammonium chloride. The sample was extracted with dichloromethane and the organic layers were pooled, dried over anhydrous sodium sulfate, filtered and concentrated to an oil. The oil was flash chromatographed on silica gel using a gradient of 40% ethyl acetate/hexanes to 100% ethyl acetate affording the title compound as a foam (0.30 g). A portion of this material was recrystallized from acetone/ hexanes to give heavy plates m.p. 100–102° C., MS m/z: 437 (M)$^+$.

EXAMPLE 96

2-Chloro-4-(3-methyl-1H-pyrazol-1-yl)-benzoic Acid Methyl Ester and 2-chloro-4-(5-methyl-1H-pyrazol-1-yl)-benzoic Acid Methyl Ester A suspension of hexane washed potassium hydride (0.424 g) in dimethylformamide (5 ml) was treated in one portion with 3-methyl pyrazole (0.85 ml) while stirring. After the gas evolution ceased, 2-chloro-4-fluorobenzoic acid methyl ester (2.0 g, 10.6) was added to the clear solution and heated at 130° C. for 15 minutes. The reaction mixture was cooled to room temperature and partitioned between ethyl acetate and brine. The organic phase was washed with water, brine,. and dried over anhydrous sodium sulfate. Removal of solvent in vacuo afforded 2.2 g of a yellow oil. (Note: 20% hydrolysis of the ester was detected by analysis of the NMR spectrum of the crude product). The desired regioisomer 2-chloro-4-(3-methyl-1H-pyrazol-1-yl)-benzoic acid methyl ester was isolated from the other isomer (described below) by flash column chromatography on silica gel (Merck 60)

eluting with dichloromethane-hexane 2:1) to give 1.55 g of the title compound as a colorless solid. MS (EI m/z: 250/252 (M)+.

The 5-regioisomer, namely 2-chloro-4-(5-methyl-1H-pyrazol-1-yl)-benzoic acid methyl ester was isolated from the above flash column chromatography on silica gel (Merck 60) by further eluting with dichloromethane-hexane 2:1 to give 0.20 g of the product as a colorless solid. MS (EI), m/z: 250/252 (M)$^+$.

EXAMPLE 97

2-Chloro-4-(3-methyl-1H-pyrazol-1-yl)-benzoic Acid

A solution of 2-chloro-4-(3-methyl-1H-pyrazol-1-yl)-benzoic acid methyl ester (1.42 g) from Example 96 and 6 ml of 1 M aqueous lithium hydroxide in tetrahydrofuran (20 ml) was stirred for 18 hours at room temperature. The reaction mixture was partitioned between ethyl acetate and 1 N hydrochloric acid. The organic layer was washed with water, brine and was dried over anhydrous sodium sulfate. Evaporation of the solvent in vacuo afforded 1.05 g of the title compound as a colorless solid. m.p. 192–193° C. MS (EI), m/z: 236/238 (M)$^+$.

EXAMPLE 98

(2,6-Dichloropyridin-3-yl)(5H,11H-Pyrrolo[2,1-c][1,4]benzodiazepin-10-yl)-methanone A solution of 2,6-dichloronicotinic acid (3.84 g), oxalyl chloride (2.0 g), and 1 drop of dimethylformamide in dichloromethane (25 ml), was stirred at room temperature for 18 hours. The solution was concentrated in vacuo to give 3.50 g of 2,6-dichloronicotinyl chloride which was added portionwise in dichloromethane (25 ml) to an ice cooled solution of 10,11-dihydro-5H-pyrrolo[2,1-c][1,4]-benzodiazepine (2.15 g) and diisopropylethylamine (2.03 g) in dichloromethane (50 ml). The mixture was stirred at room temperature for 18 hours and washed with saturated aqueous sodium bicarbonate. The organic phase was dried over anhydrous sodium sulfate and filtered through a short column of anhydrous sodium magnesium silicate. The combined organic phase was concentrated on a hot plate with the gradual addition of hexane until crystallization occurred. After cooling, the crystals were collected by filtration to yield 2.65 g of the title as an amorphous solid. m.p. 115–130° C. MS, m/z: 358.1 (M+H)$^+$.

EXAMPLE 99

(2-Chloro-6-pyrazol-1-yl-pyridin-3-yl)-(5H,11H-pyrrolo[2,1-c][1,4]benzodiazepin-10-yl)-methanone To a suspension of 60% sodium hydride in oil (0.1 g) in dimethylformamide (25 ml) was added dropwise pyrazole (0.15 g). After hydrogen gas evolution ceased, (2,6-dichloropyridin-3-yl)(5H,11H-pyrrolo[2, 1-c][1,4]benzodiazepin-10-yl)-methanone (0.67 g) was added and the reaction mixture was heated in a sand bath at 110° C. for 18 hours. The mixture was poured onto ice, diluted with brine, and extracted with dichloromethane. The combined extracts were dried over anhydrous sodium sulfate and filtered through a short column of anhydrous sodium magnesium silicate. The solution was concentrated in vacuo and triturated with diethyl ether to give 0.18 g of the title compound as a colorless solid, m.p. 133–135° C. MS m/z: 390.8 (M+H)$^+$, 779.1 (2M+H)$^+$.

EXAMPLE 100

[2-Chloro-6-(3-methylpyrazol-1-yl)-pyridin-3-yl]-(5H,11H-pyrrolo[2,1-c][1,4]benzodiazepin-10-yl)-methanone To a suspension of 60% sodium hydride in oil (0.1 g) in dimethylformamide (25 ml) was added dropwise 3-methylpyrazole (0.15 g). After hydrogen gas evolution ceased, (2,6-dichloropyridin-3-yl)(5H,11H-pyrrolo[2,1-c][1,4]benzo-diazepin-10-yl)-methanone (0.67 g) was added and the reaction mixture was heated in a sand bath at 110° C.) for 18 hours. The mixture was poured onto ice, diluted with brine, and extracted with dichloromethane. The combined extracts were dried over anhydrous sodium sulfate and filtered through a short column of anhydrous sodium magnesium silicate. The crude product was purified by preparative hplc (Dynamax c60 silica cartridge) eluting with 40% ethyl acetate in hexanes to give 0.21 g of colorless crystals, m.p. 171–172° C. MS, m/z: 404.2 (M+H)$^+$, 807.1 (2M+H)$^{30}$.

EXAMPLE 101

[2-Chloro-6-(4-methylpyrazol-1-yl)-pyridin-3-yl](5H,11H-pyrrolo[2,1-c][1,4]benzodiazepin-10-yl)-methanone To a suspension of 60% sodium hydride in oil (0.1 g) in dimethylformamide (25 ml) was added dropwise 3-methylpyrazole (0.45 g). After hydrogen gas evolution ceased, (2,6-dichloropyridin-3-yl)(5H,11H-pyrrolo[2,1-c][1,4]benzo-diazepin-10-yl)-methanone, (1.79 g) was added and the reaction mixture was heated in a sand bath at 110° C. for 18 hours. The mixture was poured onto ice, diluted with brine, and extracted with dichloromethane. The combined extracts were dried over anhydrous sodium sulfate and filtered through a short column of anhydrous sodium magnesium silicate. The crude product was purified by preparative hplc (Dynamax c60 silica cartridge) eluting with 40% ethyl acetate in hexanes to give 0.26 g of colorless crystals, m.p. 155–156° C., MS, m/z: 404.2 (M+H)$^{30}$, 807.0 (2M+H)$^+$.

EXAMPLE 102

[2-Chloro-4-(3-methyl-1,2,4-triazol-1-yl)-phenyl](5H,11H-pyrrolo[2,1-c]-[1,4]benzodiazepin-10-yl)-methanone To a suspension of 60% sodium hydride in oil (0.3 g) in dimethylformamide (50 ml) was added dropwise 3-methyl-1,2,4-triazole (0.45 g). After hydrogen gas evolution ceased, 2-chloro-4-fluorophenyl-(5H,11H-pyrrolo[2,1-c][1,4]benzo-diazepine-10-yl)-methanone (1.70 g) was added and the reaction mixture was heated in a sand bath at 110° C. for 18 hours. The mixture was poured onto ice, diluted with brine, and extracted with dichloromethane. The combined extracts were dried over anhydrous sodium sulfate and filtered through a short column of anhydrous sodium magnesium silicate. The solution was concentrated in vacuo and the residue was triturated with diethyl ether to give 1.25 g of the title compound as colorless crystals, m.p. 191–193° C., MS m/z: 404.1 (M+H)$^+$.

EXAMPLE 103

[4-(3-Methyl-1,2,4-triazol-1yl)-2-trifluoromethyl-phenyl](5H,11H-pyrrolo[2,1-c][1,4]benzodiazepin-10-yl)-methanone To a suspension of 60% sodium hydride in oil (0.3 g) in dimethylformamide (50 ml) was added dropwise 3-methyl- 1,2,4-triazole (0.45 g). After hydrogen gas evolution ceased, 4-fluoro-2-trifluoromethyl-phenyl-(5H,11H-pyrrolo[2,1-c][1,4]benzodiazepine-10-yl)-methanone (1.76 g) was added and the reaction mixture was heated in a sand bath at 110° C. for 18 hours. The mixture was poured onto ice, diluted with brine, and extracted with dichloromethane. The combined extracts were dried over anhydrous sodium sulfate and filtered through a short column of anhydrous sodium magnesium silicate. The solution was concentrated in vacuo and the residue was triturated with diethyl ether to give 0.81 g of the title compound as colorless crystals, m.p. 148–150° C., MS m/z: 438.2 (M+H)+, 875.8 (2M+H)+.

EXAMPLE 104

4-Hydrazino-2-methoxybenzoic Acid, Methyl Ester, Hydrochloride (1:1), Hydrate (2:1)

A stirred suspension of 4-amino-2-methoxybenzoic acid, methyl ester (21.74 g) in concentrated hydrochloric acid (110 ml), which was cooled to −10° C., was treated with a precooled solution of sodium nitrite (8.5 g) in water (45 ml) at a rate required to maintain a reaction temperature less than 0° C. After the addition was complete, the reaction mixture was stirred at −2° C. for 10 minutes. The cloudy, orange solution was added dropwise to a vigorously stirred precooled solution of tin (II) chloride dihydrate (101 g) in concentrated hydrochloric acid (67 ml) at −10° C. The rate of addition was controlled to maintain a reaction temperature less than −5° C. After the addition was complete, the cream colored suspension was warmed to room temperature and a solid was filtered. The solid was washed with diethyl ether and dried over anhydrous sodium sulfate to yield 52 g of a crude product. The crude product (20 g) was partitioned between aqueous 2.5 N sodium hydroxide and dichloromethane. The organic phase was filtered through diatomaceous earth, washed with brine, and dried over anhydrous magnesium sulfate. Filtration and evaporation of the solvent in vacuo afforded a cream colored solid (7.1 g), which upon treatment with one equivalent of an anhydrous hydrogen chloride solution in diethyl ether afforded the title compound as the monohydrochloride salt, m.p. 76–79° C., MS, m/z: 197 (M+H)+.

EXAMPLE 105

2-Methoxy-4-(3-methyl-pyrazol-1-yl)-benzoic Acid, Methyl Ester

To a stirred solution of 4-hydrazino-2-methoxybenzoic acid, methyl ester hydrochloride (0.88 g) from Example 104 and one drop of concentrated hydrochloric acid in a 1:1 water/methanol (10 ml) mixture was added acetylacetaldehyde dimethylacetal (0.53 g). The reaction was heated to 90° C. for 5 minutes. The reaction was concentrated in vacuo and partitioned between 1 N sodium hydroxide (10 ml) and ethyl acetate (50 ml). The organic phase was removed and washed with brine, dried over anhydrous magnesium sulfate and filtered. Evaporation of the solvent in vacuo afforded a brown oil which was combined with a previous lot (0.54 g) and recrystallized three times from diisopropyl ether to give 2-methoxy-4-(3-methyl-pyrazol-1-yl)-benzoic acid, methyl ester (0.5 g). m.p. 167–169° C., MS, m/z: 246 (M)+.

EXAMPLE 106

2-Methoxy-4-(3-methyl-pyrazol-1-yl)-benzoic Acid

A solution of 2-methoxy-4-(3-methyl-pyrazol-1-yl)-benzoic acid methyl ester (0.5 g) from Example 105 in tetrahydrofuran (2.5 ml) was treated with 1 N lithium hydroxide (2.13 ml) at room temperature. After 14 hours the solvent was removed in vacuo and the title compound precipitated by the addition at 0° C. of 1N hydrochloric acid. After drying under vacuum 0.42 g of the title compound was obtained as a solid. MS, m/z: 232 (M)+.

EXAMPLE 107

[2-Methoxy-4-(3-methyl-pyrazol-1-yl)-phenyl](5H,11H-pyrrolo[2,1-c][1,4]-benzodiazepin-10-yl) Methanone Oxalyl chloride (0.17 ml) was added to a stirred solution of 2-methoxy-4-(3-methyl-pyrazol-1-yl)-benzoic acid (0.41 g) from Example 106 and dimethylformamide (0.004 ml) in anhydrous tetrahydrofuran (10 ml). The reaction was heated at 35° C. for ten minutes. The resulting solution was evaporated in vacuo to yield the crude 2-methoxy-4-(3-methyl-pyrazol-1-yl)-benzoic acid carbonyl chloride. Following coevaporation with dichloromethane the acid chloride was dissolved in dichloromethane (10 ml) and 10,11-dihydro-5H-pyrrolo[2,1-c][1,4]-benzodiazepine (0.31 g) added. Diisopropylethylamine (0.37 ml) was added and the reaction stirred at room temperature for 2 hours. The reaction was diluted with dichloromethane and washed with water followed by 1N hydrochloric acid. The organic phase was washed with brine, dried over anhydrous magnesium sulfate and concentrated to dryness in vacuo. The solid residue was purified by flash column chromatography on silica gel eluting with hexane/ethyl acetate (2/1) to give 0.35 g of the title compound as a colorless solid, m.p. 92–94° C.

EXAMPLE 108

(3-Dimethylaminomethyl-5H,11H-pyrrolo[2,1-c][1,4]benzodiazepin-10-yl)[2-methoxy-4-(3-methyl-pyrazol-1-yl)-phenyl]-methanone To a stirred solution of [2-methoxy-4-(3-methyl-pyrazol-1-yl)-phenyl](5H,11H-pyrrolo[2,1-c][1,4]benzodiazepin-10-yl) methanone from Example 107 (0.57 g) in warm methanol (10 ml) was added N,N,N,N'-tetramethyl-diaminomethane (0.392 ml) and acetic acid (0.164 ml). Following the addition of aqueous 37% formalin solution (2.9 ml) the reaction was stirred for fifteen minutes. The mixture was concentrated in vacuo and partitioned between dichloromethane and sodium hydrogen carbonate. The organic phase was removed, washed with brine and dried over anhydrous magnesium sulfate. The solution was filtered and the solvent removed in vacuo. The residue was purified by flash column chromatography on silica eluting with chloroform/methanol (50/1) to afford a solid. Recrystallisation of the solid from acetone gave the title compound as a colorless solid, m.p. 196–198° C.

EXAMPLE 109

[2-Hydroxy-4-(3-methyl-pyrazol-1-yl](5H,11H-pyrrolo[2,1-c][1,4]-benzodiazepin-10-yl)-methanone

[2-Methoxy-4-(3-methyl-pyrazol-1-yl)-phenyl](5H,11H-pyrrolo[2,1-c][1,4]-benzodiazepin-10-yl) methanone (0.82 g) from Example 107 was dissolved in dichloromethane (20 ml) and cooled to −78° C. Boron tribromide (6.2 ml) was added and the reaction stirred at 0° C. for five minutes. Ammonium hydroxide (15 ml) was added and extracted with dichloromethane. The organic phase was washed with brine and dried over anhydrous magnesium sulfate. The solid was removed by filtration and the solvent removed in vacuo. The residue was purified by flash column chromatography on silica pressure eluting with hexane/ethyl acetate (3/1 then 2/1) to afford 0.19 g of the title compound as a colorless solid, m.p. 134–136° C.

EXAMPLE 110

2-Chloro-4-iodo-benzoic Acid, Methyl Ester

4-Amino-2-methoxy-benzoic acid methyl ester (22.97 g) was cooled to an internal temperature of −10° C. in concentrated hydrochloric acid (110 ml) and stirred as a suspension. A precooled solution of sodium nitrite (98.71 g) in water (45 ml) was added to this mixture, at such a rate so as to maintain a reaction temperature of less than 0° C. After stirring for 25 minutes at 0° C. the reaction was treated with a solution of potassium iodide (24.44 g) and iodine (18.37 g) in water (50 ml) at such a rate so as to maintain a reaction temperature of less than −40° C. Ethyl acetate (100 ml) was added during the addition and the dark mixture was stirred at 0° C. for one hour. The organic layer was diluted with ethyl acetate and washed well with saturated sodium thiosulfate solution. The resulting orange solution was washed with brine and dried over anhydrous magnesium sulfate. The solvent was evaporated in vacuo to yield an oil which was purified by suction filtration through silica gel eluting with hexane/ethyl acetate (50/1). The resulting purified oil solidified on cooling to give 33.71 g of the title compound. MS, m/z: 296 (M)$^+$.

EXAMPLE 111

4-Bromo-1-methyl-1H-pyrazole

To a suspension of prewashed (tetrahydrofuran) 60% sodium hydride in oil (11.67 g) in tetrahydrofuran (200 ml) was added dropwise a solution of 4-bromopyrazole (39.77 g) in tetrahydrofuran (50 ml). The solution was stirred at room temperature for two hours. Excess iodomethane (33 ml) in tetrahydrofuran (50 ml) was added at such a rate as to maintain a slight increase in temperature. The reaction was stirred further for two hours. The solvent was removed in vacuo and the residue stirred in diethyl ether. A precipitate was removed by suction filtration and washed with diethyl ether. The combined organic phase was evaporated in vacuo to give 42.22 g of the title compound as an oil. MS, m/z: 160 (M)$^+$.

EXAMPLE 112

1-Methyl-4-tributylstannyl-1H-pyrazole

To a precooled (<−10° C. internal temperature) solution of 1.6M n-butyl lithium in hexanes (100 ml) in anhydrous diethyl ether (100 ml) under argon was added a solution of 4-bromo-1-methyl-1H-pyrazole (23.42 g) from Example 111 in diethyl ether (50 ml) at a rate to maintain the temperature. The reaction was allowed to stir for a further 20 minutes before tributyltin chloride (43.4 ml) was added in diethyl ether (50 ml). The reaction temperature was allowed to rise to 20° C. The reaction was diluted with diethyl ether and the insoluble material removed by suction filtration. Evaporation of the solvent in vacuo afforded 56 g of the title compound as an oil. MS, m/z: 373 [M+H]$^+$. Residual amounts of tin residues were removed from the oil by distillation using a kugelrohr apparatus under high vacuum at 170° C.

EXAMPLE 113

2-Chloro-4-(1-methyl-1H-pyrazol-4-yl)-benzoic Acid, Methyl Ester

An argon degassed dimethylformamide solution (70 ml) of 2-chloro-4-iodo-benzoic acid methyl ester (25.4 g) pyrazole from Example 110, 1-methyl-4-tributylstannyl-1H-(31.77 g), tetrakis(triphenylphosphine)palladium (0) (1.8 g) and catalytic copper (I) iodide was heated at 80° C. for 7 hours. The solvent was removed in vacuo and the residue adsorbed onto silica gel. Purification by suction filtration through a pad of silica gel eluting sequentially with hexane and followed by hexane/ethyl acetate (2/1) afforded after evaporation of the solvent a solid residue which was recrystallised from diisopropyl ether to give 7.82 g of the title compound MS, m/z 250 (M)$^+$.

EXAMPLE 114

2-Chloro-4-(1-methyl-1H-pyrazol-4-yl)-benzoic Acid

To a solution of 2-chloro-4-(1-methyl-1H-pyrazol-4-yl)-benzoic acid, methyl ester (6.25 ) from Example 113 in methanol (80 ml) was added 1N sodium hydroxide (30 ml). The reaction was heated under reflux for one hour. The volume of solvent was reduced in vacuo by three quarters and the residue treated with 2N hydrochloric acid at 0° C. A precipitate was filtered and dried in vacuo to yield 5.84 g the title compound, MS m/z: 237 [M+H]$^+$.

EXAMPLE 115

[2-Chloro-4-(1-methyl-1H-pyrazol-4-yl)phenyl) (5H,11H-pyrrolo[2,1-c][1,4]-benzodiazepin-10-yl)-methanone Oxalyl chloride (0.49 ml) was added to a solution of 2-chloro-4-(1-methyl-1H-pyrazol-4-yl)-benzoic acid (0.41 g) from Example 114 and dimethylformamide (0.012 ml) in anhydrous tetrahydrofuran (20 ml). The reaction was heated at 35° C. for ten minutes. The resulting solution was evaporated in vacuo to dryness to yield the crude 2-chloro-4-(1-methyl-1H-pyrazol-4-yl)-benzoic acid carbonyl chloride. Following co-evaporation with anhydrous methylene chloride, the acid chloride was dissolved in dichloromethane (20 ml) followed by the addition of 10,11-dihydro-5H-pyrrolo[2,1-c][1,4]-benzodiazepine (0.888 g) and diisopropylethylamine (1.06 ml). The resulting solution was stirred at room temperature for 2 hours. The reaction was diluted with dichloromethane and washed with water followed by 1N hydrochloric acid. The organic phase was washed with brine and dried over anhydrous magnesium sulfate. The dichloromethane was filtered and concentrated in vacuo to dryness. The residue was purified by flash column chromatography on silica pressure eluting with hexane/ethyl acetate (2/1) to afford 1.4 g of the title compound as a colorless solid m.p. 105–109° C.

EXAMPLE 116

[2-Chloro-4-(3-methyl-pyrazol-1-yl)-phenyl]-(4H, 10H-pyrazolo[5,1-c][1,4]-benzodiazepin-5-yl)-methanone To solution of 2-chloro-4-(3-methyl-pyrazol-1-yl)-benzoyl chloride (0.214 g) Example 18 Step e in dichloromethane (10 ml) was added 5H-10,11-dihydropyrazolo[5,1-c][1,4]benzodiazepine (0.153 g) and diisopropylethylamine (0.173 ml). The reaction was stirred at room temperature for 2 hours. The reaction was diluted with dichloromethane and washed with water followed by 1N hydrochloric acid. The organic phase was washed with brine and dried over anhydrous magnesium sulfate. The dichloromethane solution was filtered and concentrated in vacuo to dryness. The residue was purified by flash column chromatography on silica pressure eluting with hexane/ethyl acetate (1/1) to afford 0.3 g of the title compound as a colorless solid, m.p. 187–188° C.

EXAMPLE 117

2-Chloro-4-(3-methyl-pyrazol-1-yl)-phenyl]-(5,10-dihydro-4H-tetrazolo[5,1-c][1,4]benzodiazepin-5-yl)-methanone To a solution of 2-chloro-4-(3-methyl-pyrazol-1-yl)-benzoyl chloride (0.18 g) Example 18 Step e in dichloromethane (10 ml) was added 10,11-dihydro-5H-tetrazole [5,1-c][1,4]benzodiazepine (0.13 g) and diisopropylethylamine (0.145 ml). The reaction was stirred at room temperature for 2 hours. The reaction was diluted with dichloromethane and washed with water followed by 1N hydrochloric acid. The organic phase was washed with brine and dried over anhydrous magnesium sulfate. The dichloromethane solution was filtered and concentrated in vacuo to dryness. The residue was purified by flash column chromatography on silica eluting with hexane/ethyl acetate (1/1) to give 0.14 g of the title compound as a colorless solid. m.p. 110–114° C.

EXAMPLE 118

1-[4-(4H,10H-pyrazolo[5,1-c][1,4]benzodiazepine-5-carbonyl)phenyl]-ethanone

A mixture of 5,10-dihydro-4H-pyrazolo[5,1-c][1,4] benzodiazepine (0.555 g), 4-acetylbenzoyl chloride (0.657 g) and N,N-diisopropylethylamine (0.464 g) in dichloromethane (15 ml) was stirred at room temperature for 4 hours. The mixture is poured into water and extracted with dichloromethane. The dichloromethane extract was washed with saturated sodium hydrogen carbonate, water and brine and dried over anhydrous sodium sulfate. The extract is filtered through a thin pad of hydrous magnesium silicate and the filter pad washed with dichloromethane. The filtrate is concentrated in vacuo to give 1.53 g of yellow solid. Trituration of the solid with ethyl acetate gave 0.747 g of the title compound as a glass, m.p. 201–210° C. The mother liquors from the trituration were evaporated and the residue (0.30 g) was chromatographed on thick layer silica gel plates (200 micron) using hexane-ethyl acetate (1:1) as solvent. The solid is triturated with ethyl acetate and combined with the 0.747 g of initially isolated product. The combined solids were precipitated from a mixture of dichloromethane -hexane to give 0.73 g of product as a glass.

EXAMPLE 119

1-[4-(4H,10H-pyrazolo[5,1-c][1,4]benzodiazepine-5-carbonyl)phenyl]-3-(dimethylamino)-prop-2-en-1-one A mixture of 1-[4-(4H,10H-pyrazolo[5,1-c][1,4] benzodiazepine-5-carbonyl) phenyl]ethanone (0.73 g), tert-butoxybis-[dimethylamino]methane (0.964 g) in dichloromethane (10 ml) was stirred at room temperature for 2 days. The mixture is concentrated in vacuo and the residue crystallized from dichloromethane-hexane to give 0.65 g of the title compound as yellow crystals, m.p. 225–230° C.

EXAMPLE 120

[4-(1-Methyl-1H-pyrazol-3-yl)phenyl](4H,10H-pyrazolo[5,1c][1,4]-benzodiazepin-5-yl)methanone (Isomer A) and [4-(2-Methyl-1H-pyrazol-3-yl) phenyl](4H,1OH-pyrazolo[5,1c][1,4]-benzodiazepin-5-yl)methanone (Isomer B)

A mixture of 1-[4-(4H,10H-pyrazolo[5,1-c][1,4] benzodiazepine-5-carbonyl)phenyl]-3-(dimethylamino)-prop-2-en-1-one (0.83 g), hydrazine (0.198 g)and acetic acid (0.336 g) in 10 ml of ethanol is refluxed for 4 hours. The volatiles were removed in vacuo and the residue dissolved in dichloromethane. The solution is washed with water, 1N sodium hydrogen carbonate, water and brine and dried over anhydrous sodium sulfate. The solution is filtered through a thin pad of hydrous magnesium silicate and the filter pad washed with ethyl acetate. The filtrate is concentrated in vacuo to give 0.56 g of light yellow solid. The solid was chromatographed on thick layer silica gel plates (200 microns) with ethyl acetate as solvent to give 0.35 g of white solid as a mixture of A and B (1:4). Multiple fractional crystallizations from ethyl acetate gives 89 mg of crystals, m.p. 155–156° C. as a mixture of A and B (9:1) and 65 mg of a glass as a mixture of A and B (1:6)

EXAMPLE 121

1-[4-(5H,11H-pyrrolo[2,1-c][1,4]benzodiazepine-10-carbonyl)-3-chlorophenyl]-ethanone Step a) Triethylamine (8.80 ml) was added to a solution of (4-bromo-2-chlorophenyl)-(5H,11H-pyrrolo[2,1-c][1,4] benzodiazepin-10-yl)-methanone (2.37 g) in pyridine (1.80 ml), in a 20 ml Carrius tube. The resultant solution was purged with nitrogen for 25 minutes then (trimethylsilyl) acetylene (1.67 ml), bis(triphenyl-phosphine)palladium(II) chloride (0.08 g) and copper(I) iodide (0.01 g) were added. The tube was filled with nitrogen-purged triethylamine, sealed and heated on an oil bath at 90° C. for 80 hours. The solution was cooled to room temperature, the solvent evaporated in vacuo, and the residue partitioned between dichloromethane and water. The dichloromethane extract was dried over anhydrous sodium sulfate, filtered, and evaporated in vacuo to a brown foam. Purification by flash chromatography on silica gel eluting with hexane-ethyl acetate (1:1) resulted in the intermediate acetylene as an off-white foam (2.11 g), MS m/z: 418 (M)$^+$. This material was used without further purification in the next step.

Step b) A solution of 1% sulfuric acid in tetrahydrofuran was saturated with mercury (II) sulfate. The intermediate acetylene (1.00 g) in tetrahydrofuran (5 ml) was stirred for 50 hours with 30 ml of the aforementioned mercury (II) sulfate-tetrahydrofuran solution. An additional amount of mercury (II) sulfate (0.01 g) and water 0.3 ml was added. After stirring for 120 hours, the reaction mixture was poured into water and extracted with dichloromethane. The dichloromethane solution was washed sequentially with saturated aqueous sodium bicarbonate and water. The dichloromethane solution was dried over anhydrous magnesium sulfate, filtered, and evaporated to dryness to yield a brown solid. Purification by flash chromatography on silica gel eluting with hexane-ethyl acetate (1:1) gave a white solid (0.30 g), mp 98–100° C., MS m/z: 364 (M)$^+$.

EXAMPLE 122

1-[4-(5H,11H-pyrrolo[2,1-c][1,4]benzodiazepine-10-carbonyl)-3-chlorophenyl]-ethanone Tributyl(ethoxyvinyl)tin (1.17 g) was added to a solution of (4-bromo-2-chlorophenyl)-(5H,11H-pyrrolo[2,1-c][1,4] benzodiazepin-10-yl)-methanone (1.24 g) in toluene (10 ml). The resultant solution was purged with nitrogen for 10 minutes, then bis(triphenylphosphine)palladium (II) chloride (0.11 g) was added. The reaction mixture was heated to reflux for 24 hours. The solution was cooled to room temperature and 5% aqueous hydrochloric acid (10 ml) was added. After stirring for one hour, the mixture was filtered through a pad of diatomaceous. Diethyl ether (5 ml) was added to the filtrate, and the resulting mixture was extracted with ethyl acetate. The organic layer was dried over anhydrous magnesium sulfate, filtered, and evaporated in vacuo to yield a brown glass. Purification by flash chromatography on silica gel eluting with hexane-ethyl acetate (1:1) resulted in a white solid (0.30 g), MS, m/z: 364 $(M)^+$.

EXAMPLE 123

[2-Chloro-4-(3-methyl-4-ethynyl-phenyl) (5H,11H-pyrrolo[2,1-c][1,4]-benzodiazepin-10-yl)-methanone Treatment of the intermediate acetylene of Example 121 step A with a 1M solution of tetrabutylammonium fluoride in tetrahydrofuran at room temperature provided upon solvent removal an 84% yield the title compound as an orange-yellow solid, m.p. 84–86° C., MS, m/z: 346 $(M)^+$.

Process for Preparing Pharmaceutical Formulations

This invention also includes methods for producing the formulations disclosed herein. A process of this invention comprises the steps of:

a) combining, preferably with mixing or stirring, the PEG and surfactant components to create a first carrier mixture;

b) raising the temperature of the first carrier mixture to a range of from about 75° C. to about 95° C., preferably from about 80° C. to about 90° C.;

c) adding the active ingredient to create a first pharmaceutical composition mixture;

d) stirring the first pharmaceutical composition mixture, preferably with heating, until the first pharmaceutical composition mixture is clear, preferably at a temperature from about 115° C. to about 170° C., preferably to a temperature from about 130° C. to about 150° C., more preferably at a temperature from about 135° C. to about 145° C.;

e) cooling the first pharmaceutical composition, if necessary, to a temperature of from about 75° C. to about 95° C., preferably from about 80° C. to about 90° C.;

g) adding the amount of sucrose fatty acid ester(s) and/or povidone to create a final pharmaceutical composition mixture, preferably with stirring until the final pharmaceutical composition mixture is clear.

In cases wherein optional antioxidants or preservatives are used, such as BHA, BHT, etc., the following steps may be employed:

a) combining, preferably with mixing or stirring, the PEG component (such as a mixture of PEG 400 and PEG 1000) and the surfactant component (such as Polysorbate 80) to create a first carrier mixture;

b) raising the temperature of the first carrier mixture to a range of from about 75° C. to about 95° C., preferably from about 80° C. to about 90° C.;

c) adding to the first carrier mixture optional antioxidant or preservative components to create a second carrier mixture, which is then stirred or otherwise mixed until the second carrier mixture is a clear solution;

d) adding the active ingredient to create a first pharmaceutical composition mixture;

e) stirring the first pharmaceutical composition mixture, preferably with heating, until the first pharmaceutical composition mixture is clear, preferably at a temperature from about 130° C. to about 150° C., more preferably at a temperature from about 135° C. to about 145° C.;

f) optionally cooling the first pharmaceutical composition to a temperature of from about 75° C. to about 95° C., preferably from about 80° C. to about 90° C.;

g) adding the amount of sucrose fatty acid ester(s) and/or povidone to create a final pharmaceutical composition mixture, preferably with stirring until the final pharmaceutical composition mixture is clear.

One skilled in the art will understand the viscosity and form of the final formulation may be manipulated with components within the scope of this invention and temperature ranges during processing. For instance, a fluid or semi-solid composition may be produced with the more fluid PEG, surfactant and PVP species within the scope of this invention. More gel-like, viscous or semi-solid compositions may be produced with combinations of higher molecular weight PEG components and PVP components having higher K values. Moreover, the components may be cooled below their melting point if milling or other processing of the final composition is desired. To create a more pelletized initial composition, a fluid composition of this invention may be sprayed onto a cooled Teflon®-coated surface to form small solid spheres, which may be individually coated or collected for further processing.

Specific non-limiting examples of formulations within the scope of this invention are provided below.

EXAMPLE 1

50 mg/capsule: Oral Formulation at 10% Drug Loading

In place of the polysorbate 80 in this formulation of Example 1, other polysorbate series such as Tween 20, 40 and 60 can also be used, alone or in combination with each other and/or polysorbate 80.

|  | (% w/w) | per capsule (mg) | 20,000 capsule batch (g) |
|---|---|---|---|
| active ingredient | 10.42 | 50.00 | 1000.00 |
| Inactive Ingredients: |  |  |  |
| PEG 1000, NF | 30.96 | 148.61 | 2,972.16 |
| Povidone USP K-17 | 10.00 | 48.00 | 960.00 |
| Polysorbate 80, NF | 10.00 | 48.00 | 960.00 |
| BHT, NF | 0.09 | 0.42 | 8.32 |
| BHA, NF | 0.87 | 4.16 | 83.2 |
| PEG 400, NF[2] | Q.S. to 100 | Q.S. to 480.00 | Q.S. to 9,600 |

1. Weigh the Polysorbate 80, PEG 400, and PEG 1000 into a suitable mixing vessel, stir using a top mounted mixer, and warm to 85±5° C.
2. Add BHT and BHA to the mixing vessel, very slowly to prevent formation of lumps. Continue stirring at 85±5° C., until a clear solution was formed.
3. Add active ingredient to the vessel at 85±5° C., very slowly to prevent formation of lumps. Slowly raise the temperature to 125±5° C., and stir until the active ingredient dissolves completely.
4. Cool the solution in step 4. to 60±5° C.
5. Add Povidone, USP, K-17 (Plasdone C-15, ISP) slowly to step 5, to prevent the formation of lumps.

Let the solution warm up to 85±5° C. Stir until the solution becomes clear.

6. Encapsulate 480 mg of the finished solution (in step 10) into size 1 capsules at 38±5° C. using Hoflinger and Karg (H&K) 800L encapsulator machine. During encapsulation cool the body of capsule using cool Nitrogen, which was passed through dry ice.
7. Band seal the capsules with gelatin solution.

EXAMPLE 2

50 mg/capsule: Oral Formulation at 10% Drug Loading

In place of surfactant used in this formulation (poloxamer 188), other polymers in the series such as Pluronic L44, Pluronic L101 can also be used.

|  | (% w/w) | per capsule (mg) | 20,000 capsule batch (g) |
|---|---|---|---|
| active ingredient | 10.42 | 50.00 | 1000.00 |
| Inactive Ingredients: |  |  |  |
| Povidone USP K-17 (Plasdone C-15, ISP) | 10.00 | 48.00 | 960.00 |
| Poloxamer 188, NF | 12.00 | 57.60 | 1152.00 |
| BHT NF | 0.09 | 0.42 | 8.32 |
| BHA NF | 0.87 | 4.16 | 83.20 |
| PEG 400 NF | Q.S. to 100 | Q.S. to 480.00 | Q.S. to 9600 g |

This formulation is manufactured the same as that of the formula of Example 1 (50 mg/capsule) with the exception that 12% of poloxamer was used in place of the polysorbate 80 in this formulation. The encapsulation weight is 480 mg.

EXAMPLE 3

50 mg/capsule

Example 4 provides a formulation with a combination of two or more surfactants.

|  | (% w/w) | per capsule (mg) | 20,000 capsule batch (g) |
|---|---|---|---|
| active ingredient | 10.64 | 51.07 | 1,021.44 |
| Inactive Ingredient: |  |  |  |
| PEG 1000, NF | 28.60 | 137.28 | 2,745.60 |
| Povidone USP K-17 (Plasdone C-15, ISP) | 10.00 | 48.00 | 960.00 |
| Polysorbate 40, NF | 5.00 | 24.00 | 480.00 |
| Poloxamer 188, NF | 10.00 | 48.00 |  |
| BHT, NF | 0.09 | 0.43 | 8.64 |
| BHA, NF | 0.87 | 4.18 | 83.52 |
| PEG 400, NF | Q.S. to 100 | Q.S. to 480.00 | Q.S. to 9600.00 |

The formulation of Example 3 is manufactured the same as that of Example 1 (50 mg/capsule) with the exception that two surfactants, polysorbate 40 and poloxamer 188 were added in step 1 along with PEG 400 and PEG 1000. The encapsulation weight is 480 mg.

EXAMPLE 4

25 mg/capsule: Oral Formulation at 5% Drug Loading

|  | (% w/w) | per capsule (mg) | 20,000 capsule batch (g) |
|---|---|---|---|
| active ingredient | 5.49 | 25.00 | 500.00 |
| Inactive Ingredient: |  |  |  |
| PEG 1000, NF | 32.66 | 148.61 | 2,972.16 |
| Povidone, USP K-17 (Plasdone C-15, ISP) | 10.55 | 48.00 | 960.00 |
| Polysorbate 80, NF | 10.55 | 48.00 | 960.00 |
| BHT, NF | 0.09 | 0.42 | 8.32 |
| BHA, NF | 0.91 | 4.16 | 83.2 |
| PEG 400, NF[2] | Q.S. to 100 | Q.S. to 455.00 | Q.S. to 9,100 g |

The formulation of Example 4 is produced in the same manner as that of 50 mg/capsule, above, with the exception that the heating temperature to solubilize the active ingredient in step 3 is 115±5° C., instead of 120±5° C. The encapsulation weight is 455 mg.

EXAMPLE 5

100 mg/capsule: Oral Formulation at 15% Drug Loading

|  | (% w/w) | per capsule (mg) | 20,000 capsule batch (g) |
|---|---|---|---|
| active ingredient | 15.38 | 100.00 | 2,000.00 |
| Inactive Ingredient: |  |  |  |
| PEG 1000, NF | 28.98 | 188.35 | 3,767.05 |
| Povidone USP K-17 (Plasdone C-15, ISP)[3] | 10.00 | 65.00 | 1,300.00 |
| Polysorbate 80, NF | 9.45 | 61.39 | 1,227.91 |
| BHT, NF | 0.08 | 0.53 | 10.64 |
| BHA, NF | 0.82 | 5.32 | 106.42 |
| PEG 400, NF | Q.S. to 100 | Q.S. to 650.00 | Q.S. to 13,000.00 |

This formulation is produced with the same steps as the 50 mg/capsule, above, with the exception that the heating temperature to solubilize the active ingredient in step 3 is 145±5° C., instead of 120±5° C. The encapsulation weight is 650 mg in size 0 hard gelatin capsule.

EXAMPLE 6

150 mg Active Ingredient in Size 00 Capsule

|  | (% w/w) | per capsule (mg) | 20,000 capsule batch (g) |
|---|---|---|---|
| active ingredient | 16.48 | 149.97 | 2,999.36 |
| Inactive Ingredients: |  |  |  |
| PEG 1000, NF | 26.3 | 239.33 | 4,786.60 |
| Povidone USP K-17 (Plasdone C-15, ISP) | 15 | 136.50 | 2,730.00 |

-continued

|  | (% w/w) | per capsule (mg) | 20,000 capsule batch (g) |
|---|---|---|---|
| Polysorbate 80, NF | 9.32 | 84.81 | 1,696.24 |
| BHT, NF | 0.08 | 0.73 | 14.56 |
| BHA, NF | 0.81 | 7.37 | 147.42 |
| PEG 400, NF | Q.S. to 100 | Q.S. to 910.00 | Q.S. to 18,200.00 |

This formulation of Example 6 is produced with the same steps as that of 50 mg/capsule with the exception of the heating temperature to solubilize the active ingredient in step 3 is 150±5° C., instead of 145±5° C. The encapsulation weight is 910 mg in size 00 hard gelatin capsule.

The following specific Examples 7 through 11 shown in Table 1, below, can be formulated as described above to create formulations of 10% active ingredient with varying concentrations of PEG 400, PEG 1000, two PVP components with respective K values of 15 and 90, and a combination of BHA and BHT as an adjuvant component.

TABLE 1

| Example No. | PEG 400 (%) | PEG 1000 (%) | PVP K15 (%) | PVP K90 (%) | BHT (%) | BHA (%) | NATC (%) | Active Ingrednt (%) |
|---|---|---|---|---|---|---|---|---|
| 7 | 55.40 | 20.00 | 10.00 | 0.00 | 0.20 | 2.00 | 2.40 | 10.00 |
| 8 | 40.40 | 35.00 | 10.00 | 0.00 | 0.20 | 2.00 | 2.40 | 10.00 |
| 9 | 75.40 | 0.00 | 5.00 | 5.00 | 0.20 | 2.00 | 2.40 | 10.00 |
| 10 | 65.40 | 10.00 | 0.00 | 10.00 | 0.20 | 2.00 | 2.40 | 10.00 |
| 11 | 40.40 | 35.00 | 5.00 | 5.00 | 0.20 | 2.00 | 2.40 | 10.00 |

Simlarly, the following Examples 12 through 32 may be formulated by the methods herein using PEG 400, PEG 1000, PVP with a K value of 17, active ingredient, BHA and BHT as antioxidants or preservatives and the additional components listed as "other".

TABLE 2

| Ex. No. | PEG 400 | PEG 1000 | PVP K-17 | Active Ingred. | BHA | BHT | Other | Other |
|---|---|---|---|---|---|---|---|---|
| 12 | 40.40 | 35.00 | 10.00 | 10.00 | 2.00 | 0.20 | Sodium Taurocholate 2.40 | — |
| 13 | 75.40 | — | 5.00 | 10.21 | 2.00 | 0.20 | Sodium Taurocholate 2.40 | PVP K-90 5.00 |
| 14 | 42.59 | 35.00 | 10.00 | 10.21 | 2.00 | 0.20 | — | — |
| 15 | 34.35 | 28.23 | 10.00 | 10.21 | 2.00 | 0.20 | Poloxamer 188 15.00 | — |
| 16 | 42.59 | 20.00 | 10.00 | 10.21 | 2.00 | 0.20 | Poloxamer 188 15.00 | — |
| 17 | 37.10 | 30.49 | 10.00 | 10.21 | 2.00 | 0.20 | Poloxamer 188 10.00 | — |
| 18 | 35.72 | 29.36 | 10.00 | 10.21 | 2.00 | 0.20 | Poloxamer 188 12.50 | — |
| 19 | 34.35 | 28.23 | 10.00 | 10.21 | 2.00 | 0.20 | Poloxamer 188 15.00 | — |
| 20 | 37.10 | 30.49 | 10.00 | 10.21 | 2.00 | 0.20 | Poloxamer 188 10.00 | — |
| 21 | 34.35 | 28.23 | 10.00 | 10.21 | 2.00 | 0.20 | Poloxamer 188 15.00 | — |
| 22 | 35.72 | 29.36 | 10.00 | 10.21 | 2.00 | 0.20 | Poloxamer 188 12.50 | — |
| 23 | 36.86 | 30.30 | 10.00 | 10.64 | 2.00 | 0.20 | Pluronic L44 10.00 | — |
| 24 | 36.86 | 30.30 | 10.00 | 10.64 | 2.00 | 0.20 | Pluronic L101 10.00 | — |
| 25 | 39.61 | 32.55 | 10.00 | 10.64 | 2.00 | 0.20 | Tween 40 5.00 | — |
| 26 | 41.25 | 33.91 | 10.00 | 10.64 | 2.00 | 0.20 | Tween 40 2.00 | — |
| 27 | 39.61 | 32.55 | 10.00 | 10.64 | 2.00 | 0.20 | Tween 20 5.00 | — |
| 28 | 41.25 | 33.91 | 10.00 | 10.64 | 2.00 | 0.20 | Tween 20 2.00 | — |
| 29 | 34.12 | 28.04 | 10.00 | 10.64 | 2.00 | 0.20 | Tween 40 5.00 | Poloxamer 188 10.00 |
| 30 | 36.86 | 30.30 | 10.00 | 10.64 | 2.00 | 0.20 | Tween 40 | — |
| 31 | 36.86 | 30.30 | 10.00 | 10.64 | 2.00 | 0.20 | Tween 80 10.00 | — |
| 32 | 34.12 | 28.04 | 10.00 | 10.64 | 2.00 | 0.20 | Tween 80 5.00 | Poloxamer 188 10.00 |

What is claimed:

1. A pharmaceutical composition comprising:

i) from about 1% to about 20% of an active ingredient, or a pharmaceutically acceptable salt thereof, having the structure:

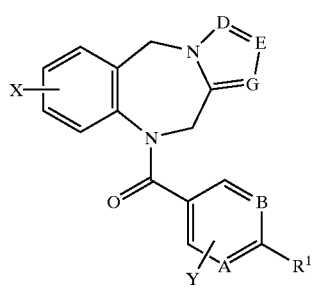 (I)

wherein:
A, B, E, G are, independently, CH or nitrogen;
D is, independently, C—W or nitrogen;
R¹ is alkanoyl of 2 to 7 carbon atoms, a group selected from CN, COOH, CONH₂,

or a moiety selected from the group:

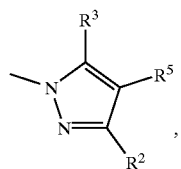 (a)

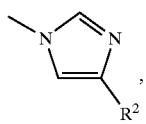 (b)

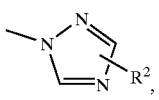 (c)

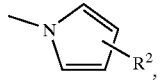 (d)

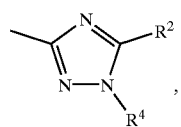 (e)

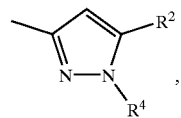 (f)

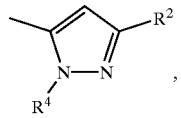 (g)

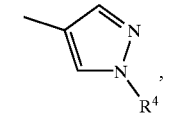 (h)

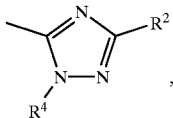 (i)

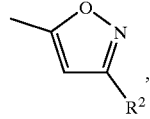 (j)

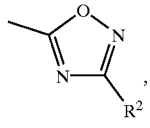 (k)

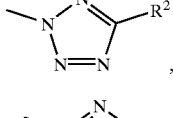 (l)

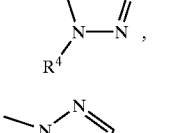 (m)

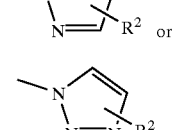 (n)

or (o)

$R^2$, $R^3$ and $R^5$ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

$R^4$ is hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, or an acyl substituent selected from the group consisting of alkanoyl of 2 to 7 carbon atoms, alkenoyl of 3 to 7 carbon atoms, cycloalkanoyl of 3 to 7 carbon atoms, aroyl, or arylalkanoyl;

X and Y are, independently, hydrogen, straight chain alkyl of 1 to 6 carbon atoms, branched chain alkyl of 3 to 7 carbon atoms, cycloalkyl of 3 to 7 carbon atoms, perfluoroalkyl of 1 to 6 carbons, alkoxyalkyl of 2 to 7 carbon atoms, halogen (including chlorine, bromine, fluorine, and iodine), alkoxy of 1 to 6 carbons, hydroxy, $CF_3$, or perfluoroalkyl of 2 to 6 carbons;

W is hydrogen, halogen (preferably chloro, bromo or iodo), alkyl, alkoxyalkyl of 2 to 7 carbons, hydroxyalkyl of 1 to 6 carbons, or $CH_2NR^6R^7$;

$R^6$ and $R^7$ are, independently, hydrogen, straight chain alkyl of 1 to 6 carbon atoms, branched chain alkyl of 3 to 7 carbon atoms; or, taken together with the nitrogen atom of $CH_2NR^6R^7$, $R^6$ and $R^7$ form a five or six membered ring optionally containing one or more additional heteroatoms such as, but not limited to, those of the group:

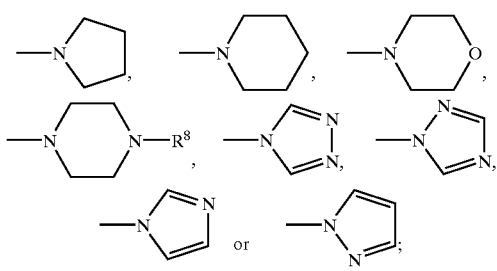

R⁸ is a straight chain alkyl of 1 to 6 carbon atoms
R⁹ is independently hydrogen, trimethylsilyl or a straight chain alkyl of 1 to 6 carbon atoms;

ii) from about 1% to about 18% of a surfactant component;
iii) from about 50% to about 80% of a component of one or more polyethylene glycols; and
iv) from about 1% to about 20% of a component of:
  i) one or more sucrose fatty acid esters; or
  ii) a polyvinylpyrrolidone with a K value between about 15 and 90; or
  iii) a combination of one or more sucrose fatty acid esters and polyvinylpyrrolidone.

2. A pharmaceutical composition of claim 1 wherein the active ingredient has the structure:

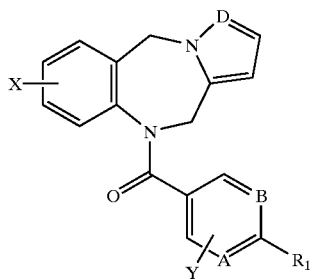

wherein:

A and B are, independently, CH or nitrogen;
D is C—W or nitrogen;
R¹ is alkanoyl of 2 to 7 carbon atoms or a group selected from

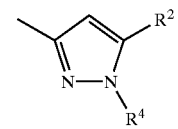 (a)

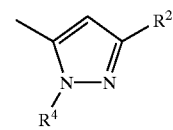 (b)

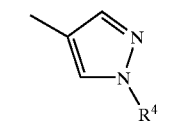 (e)

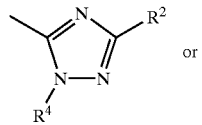

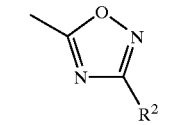

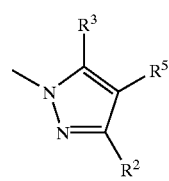 (f)

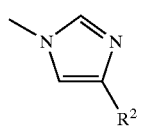 (g)

(h)

(i) or (k)

R², R³ and R⁵ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;
R⁴, X, Y, W, R⁶, R⁷ and R⁸ are as defined in claim 1;
or a pharmaceutically acceptable salt thereof.

3. A pharmaceutical composition of claim 1 wherein the active ingredient is [2-Chloro-4-(3-methyl-pyrazol-1-yl)-phenyl-(5H,11H)-pyrrolo[2,1-c][1,4]benzodiazepin-10-yl)-methanone, or a pharmaceutically acceptable salt thereof.

4. A pharmaceutical composition of claim 1 comprising:
a) from about 5% to about 16% of active ingredient, or a pharmaceutically acceptable salt thereof;
b) from about 5% to about 15% of a surfactant component;
c) from about 55% to about 70% of a component of one or more polyethylene glycols; and
d) from about 1% to about 20% of a component of:
  i) one or more sucrose fatty acid esters; or
  ii) a polyvinylpyrrolidone with a K value between about 15 and 90; or
  iii) a combination of one or more sucrose fatty acid esters and polyvinylpyrrolidone, as defined above.

5. A pharmaceutical composition of claim 1 wherein the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof.

6. A pharmaceutical composition of claim 1 wherein the component of one or more polyethylene glycols comprises one or more polyethylene glycols having an average molecular weight between about 190 to about 3450.

7. A pharmaceutical composition of claim 4 wherein the component of one or more polyethylene glycols comprises one or more polyethylene glycols having an average molecular weight between about 400 and 1540.

8. A pharmaceutical composition of claim 4 wherein the component of one or more polyethylene glycols comprises a mixture of PEG 400 and PEG 1000 in a ratio of between about 2.5:1 to about 1:2.5.

9. A pharmaceutical composition of claim 1 wherein the polyvinylpyrrolidone component has a K value of about 17.

10. A pharmaceutical composition comprising:
   a) from about 1% to about 20% of an active ingredient of claim 1, or a pharmaceutically acceptable salt thereof;
   b) from about 5% to about 18% of a surfactant component;
   c) from about 50% to about 80% of a component of one or more polyethylene glycols;
   d) from about 1% to about 20% of one or more sucrose fatty acid esters or polyvinylpyrrolidone with a K value between about 15 and 90; and
   e) from about 0.1% to about 4% of one or more antioxidants or preservatives.

11. A pharmaceutical composition of claim 10 wherein:
   a) the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof;
   b) the component of one or more polyethylene glycols comprises one or more polyethylene glycols having an average molecular weight between about 400 and 1540; and
   c) the one or more antioxidants or preservatives are selected from ascorbyl palmitate, benzyl alcohol, butylated hydroxyanisole, or butylated hydroxytoluene, or combinations thereof.

12. A pharmaceutical composition of claim 10 comprising:
   a) from about 5% to about 16% of an active ingredient as defined in claim 1, or a pharmaceutically acceptable salt thereof;
   b) from about 5% to about 15% of a surfactant component;
   c) from about 55% to about 70% of a component of one or more polyethylene glycols;
   d) from about 1% to about 20% of one or more sucrose fatty acid esters 10 or polyvinylpyrrolidone with a K value between about 15 and 90;
   e) from about 0.3% to about 2.5% (% w/w) BHA and/or from about 0.005% to about 0.15% (% w/w) BHT.

13. A pharmaceutical composition of claim 10 comprising:
   a) from about 5% to about 16% of active ingredient, or a pharmaceutically acceptable salt thereof;
   b) from about 5% to about 15% of a surfactant component comprising polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof;
   c) a component of from about 55% to about 70% of one or more polyethylene glycols having an average molecular weight between about 400 and 1540;
   d) from about 1% to about 20% of polyvinylpyrrolidone (PVP) with a K value between about 15 and 90; and
   e) from about 0.3% to about 2.5% (% w/w) BHA and from about 0.005% to about 0.15% (% w/w) BHT.

14. A pharmaceutical composition of claim 1 which is contained within a hard or soft gelatin capsule.

15. A process for formulating a pharmaceutical composition comprising from about 1% to about 20% of an active ingredient as defined in claim 1, or a pharmaceutically acceptable salt thereof; from about 5% to about 18% of a surfactant component; from about 50% to about 80% of a component of one or more polyethylene glycols; a component of from about 1% to about 20% of one or more sucrose fatty acid esters or polyvinylpyrrolidone with a K value between about 15 and 90; and from about 0.1% to about 3% of one or more adjuvants; the process comprising the steps of:
   a) combining the component of one or more polyethylene glycols and the surfactant component to create a first carrier mixture;
   b) raising the temperature of the first carrier mixture to a range of from about 75° C. to about 95° C.;
   c) adding to the first carrier mixture the one or more antioxidants or preservatives to create a second carrier mixture;
   d) adding the active ingredient, or a pharmaceutically acceptable salt thereof, to create a first pharmaceutical composition mixture;
   e) raising the first pharmaceutical composition mixture to a temperature from about 130° C. to about 150° C., with stirring or mixing;
   f) cooling the first pharmaceutical composition to a temperature of from about 75° C. to about 95° C.;
   g) adding the component of from about 1% to about 20% of one or more sucrose fatty acid esters or polyvinylpyrrolidone with a K value between about 15 and 90 to create a final pharmaceutical composition mixture.

16. The process of claim 15 wherein:
   a) the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof;
   b) the component of one or more polyethylene glycols comprises one or more polyethylene glycols having an average molecular weight between about 400 and 1540; and
   c) the one or more antioxidants or preservatives are selected from ascorbyl palmitate, benzyl alcohol, butylated hydroxyanisole, or butylated hydroxytoluene, or combinations thereof.

17. A process for formulating a pharmaceutical composition comprising from about 1% to about 20% of an active ingredient as defined in claim 1, or a pharmaceutically acceptable salt thereof; from about 5% to about 18% of a surfactant component; from about 50% to about 80% of a component of one or more polyethylene glycols; a component of from about 1% to about 20% of polyvinylpyrrolidone with a K value between about 15 and 90; and an antioxidant or preservative component of from about 0.3% to about 2.5% butyrated hydroxyanisole and from about 0.005% to about 0.15% butylated hydroxytoluene; the process comprising the steps of:
   a) combining, preferably with mixing or stirring, the component of one or more polyethylene glycols and the surfactant component to create a first carrier mixture;

b) raising the temperature of the first carrier mixture to a range of from about 75° C. to about 95° C.;

c) adding to the first carrier mixture the antioxidant or preservative component to create a second carrier mixture;

d) adding the active ingredient, or a pharmaceutically acceptable salt thereof to create a first pharmaceutical composition mixture;

e) raising the temperature of the first pharmaceutical composition mixture to a temperature from about 130° C. to about 150° C.;

f) stirring or mixing the first pharmaceutical composition mixture until the first pharmaceutical composition mixture is clear;

f) bringing the first pharmaceutical composition to a temperature of from about 75° C. to about 95° C.;

g) adding the component of from about 1% to about 20% of povidone to create a final pharmaceutical composition mixture.

18. The process of claim 15 wherein:

a) the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof; and b) the component of one or more polyethylene glycols comprises one or more polyethylene glycols having an average molecular weight between about 400 and 1540.

19. A process for formulating a pharmaceutical composition comprising from about 5% to about 16% of an active ingredient as defined in claim 1, or a pharmaceutically acceptable salt thereof; from about 5% to about 15% of a surfactant component; from about 55% to about 70% of a component of one or more polyethylene glycols; a component of from about 5% to about 15% of polyvinylpyrrolidone with a K value between about 15 and 90; and an antioxidant or preservative component of from about 0.3% to about 2.5% butylated hydroxyanisole and from about 0.005% to about 0.15% butylated hydroxytoluene; the process comprising the steps of:

a) combining, preferably with mixing or stirring, the component of one or more polyethylene glycols and the surfactant component to create a first carrier mixture;

b) raising the temperature of the first carrier mixture to a range of from about 80° C. to about 90° C.;

c) adding to the first carrier mixture the antioxidant or preservative component to create a second carrier mixture;

d) adding the active ingredient, or a pharmaceutically acceptable salt thereof to create a first pharmaceutical composition mixture;

e) raising the temperature of the first pharmaceutical composition mixture to a temperature from about 135° C. to about 145° C.;

f) stirring or mixing the first pharmaceutical composition mixture until the first pharmaceutical composition mixture is clear;

f) bringing the first pharmaceutical composition to a temperature of from about 80° C. to about 90° C.;

g) adding the component of from about 5% to about 15% of povidone to create a final pharmaceutical composition mixture.

* * * * *

UNITED STATES PATENT AND TRADEMARK OFFICE
CERTIFICATE OF CORRECTION

PATENT NO. : 6,831,079 B1 Page 1 of 1
DATED : December 14, 2004
INVENTOR(S) : Yoon et al.

It is certified that error appears in the above-identified patent and that said Letters Patent is hereby corrected as shown below:

Title page,
Item [*] Notice, delete the phrase "by 401" and insert -- by 521 days --

Signed and Sealed this

Seventh Day of June, 2005

JON W. DUDAS
*Director of the United States Patent and Trademark Office*